United States Patent
Or et al.

(10) Patent No.: US 7,402,568 B2
(45) Date of Patent: Jul. 22, 2008

(54) BICYCLIC 9A-AZALIDE DERIVATIVES

(75) Inventors: Yat Sun Or, Watertown, MA (US);
Yao-Ling Qiu, Andover, MA (US);
Guoqiang Wang, Belmont, MA (US);
Deqiang Niu, Lexington, MA (US); Ly Tam Phan, Quincy, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 255 days.

(21) Appl. No.: 11/236,043

(22) Filed: Sep. 27, 2005

(65) Prior Publication Data

US 2006/0069048 A1  Mar. 30, 2006

Related U.S. Application Data

(60) Provisional application No. 60/614,171, filed on Sep. 29, 2004.

(51) Int. Cl.
*A61K 31/70*  (2006.01)
*C07H 17/08*  (2006.01)

(52) U.S. Cl. .......................................... 514/29; 536/7.4
(58) Field of Classification Search ........................ None
See application file for complete search history.

(56) References Cited

U.S. PATENT DOCUMENTS

| 6,369,035 B1 | 4/2002 | Kobrehel et al. |
| 6,645,941 B1 | 11/2003 | Wang et al. |
| 6,764,996 B1 | 7/2004 | Or et al. |
| 6,764,998 B1 | 7/2004 | Wang et al. |
| 6,852,702 B2 | 2/2005 | Kujundzic et al. |
| 2005/0014707 A1 | 1/2005 | Wang et al. |
| 2005/0090460 A1 | 4/2005 | Wang et al. |

FOREIGN PATENT DOCUMENTS

| EP | 0 283 055 A2 | 9/1988 |
| WO | WO 93/13116 | 7/1993 |
| WO | WO 98/56802 | 12/1998 |
| WO | WO 99/00124 | 1/1999 |
| WO | WO 99/00125 | 1/1999 |
| WO | WO 99/20639 | 4/1999 |
| WO | WO 02/12260 A1 | 2/2002 |
| WO | WO 02/055531 A1 | 7/2002 |
| WO | WO 02/068438 | 9/2002 |
| WO | WO 2004087728 | 10/2004 |
| WO | WO 2005000863 | 1/2005 |

OTHER PUBLICATIONS

U.S. Appl. No. 11/008,581, filed Dec. 7, 2004, Or et al.
U.S. Appl. No. 11/324,502, filed Jan. 2, 2006, Or et al.
Bright, G. Michael, et al., "Synthesis, In Vitro and In Vivo Activity of Novel 9-Deoxo-9a-Aza-9a-Homoerythromycin A Derivatives; A New Class of Macrolide Antibiotics, the Azalides," *J. of Antibiotics*, vol. XLI(8): 1029-1047 (1988).

*Primary Examiner*—Elli Peselev
(74) *Attorney, Agent, or Firm*—Carolyn S. Elmore; Darlene A. Vanstone; Elmore Patent Law Group

(57) ABSTRACT

The present invention discloses compounds of formulae I and II, or pharmaceutically acceptable salts, esters, or prodrugs thereof:

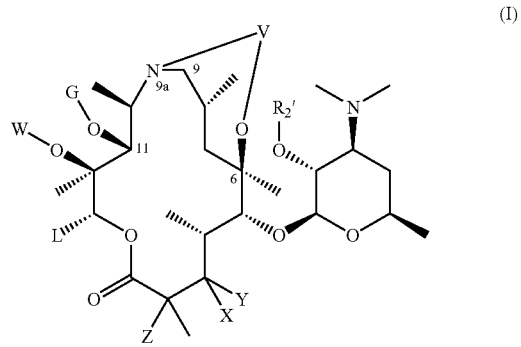

(I)

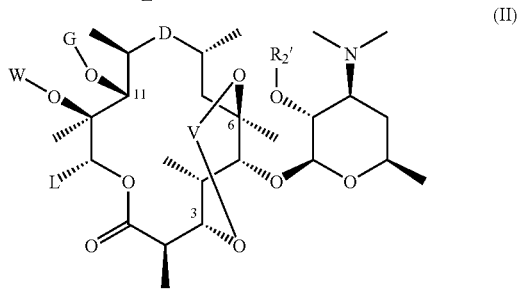

(II)

which exhibit antibacterial properties. The present invention further relates to pharmaceutical compositions comprising the aforementioned compounds for administration to a subject in need of antibiotic treatment. The invention also relates to methods of treating a bacterial infection in a subject by administering a pharmaceutical composition comprising the compounds of the present invention. The invention further includes process by which to make the compounds of the present invention.

22 Claims, No Drawings

BICYCLIC 9A-AZALIDE DERIVATIVES

RELATED APPLICATION

This application claims the benefit of U.S. Provisional Application No. 60/614,171, filed on Sep. 29, 2004. The entire teachings of the above application are incorporated herein by reference.

TECHNICAL FIELD

The present invention relates to novel semisynthetic macrolides having antibacterial activity and useful in the treatment and prevention of bacterial infections. More particularly, the invention relates to bicyclic 9a-azalide derivatives, compositions comprising such compounds, methods for using the same, and processes by which to make such compounds.

BACKGROUND OF THE INVENTION

Macrolide antibacterial agents are widely used to treat and prevent bacterial infections. However, the discovery of bacterial strains which have resistance or insufficient susceptibility to macrolide antibacterial agents has promoted the development of compounds with modified or improved profiles of antibiotic activity. One such class of compounds is azalides, which includes azithromycin, described in U.S. Pat. Nos. 4,474,768 and 4,517,359. Azalides are macrolide antibacterial agents with a ring structure similar to the erythronolide A or B, however azalides possess a substituted or unsubstituted nitrogen moiety at the 9a position as illustrated in the following structure:

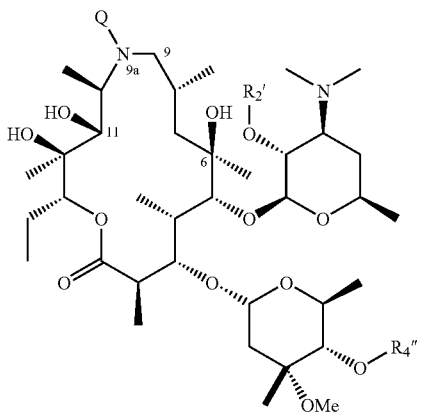

The potential for azalides to display modified or improved profiles for antibiotic activity has spawned extensive research to identify additional azalide derivatives with enhanced clinical properties. The following are examples of current efforts in azalide research:

PCT Application WO98/56801, published Dec. 17, 1998 discloses a series of 9a-(N-(alkyl))-azalide erythromycin A derivatives and a series of 9a-(N-(alkyl))-azalide 6-O-methylerythomycin A derivatives;

PCT Application WO98/56802, published Dec. 17, 1998 discloses a series of 9a-(N—(H))-azalide erythromycin A derivatives and a series of 9a-(N—(H))-azalide 6-O-methyl erythromycin A derivatives;

PCT Application WO99/00124, published Jan. 7, 1999 and PCT Application WO99/00125, published Jan. 7, 1999 disclose a series of 9a-(N—($R_n$))-azalide 3-thioxo erythromycin A derivatives and a series of 9a-(N—($R_n$))-azalide 6-O-methyl 3-oxo erythromycin A derivatives, wherein $R_n$ is an optionally substituted alkyl or heteroalkyl; and U.S. Pat. No. 5,686,587 discloses a synthesis of azithromycin comprising introducing a 9a-(N(H))-moiety to erythromycin A by oxime formation, Beckmann rearrangement, reduction, and methylation.

Additional disclosures delineating 15-membered azalide derivatives include, but are not limited to: PCT Application No. WO001/14397 (2001); PCT Application No. WO03/042228 (2003); PCT Application No. WO02/12260 (2002); U.S. Pat. No. 6,110,965 (2000); European Application No. 0 283 05 5 (1990); PCT Application No. WO99/20639 (1999); PCT Application No. WO02/055531 (2002); PCT Application No. WO93/13116 (1993); and commonly-assigned U.S. application Ser. No. 10/397,923 (filed Mar. 26, 2003) and Ser. No. 10/464,188 (filed Jun. 18, 2003).

PCT Application WO 03/095466 A1, published Nov. 20, 2003 and PCT Application WO 03/097659 A1, published Nov. 27, 2003 disclose a series of bicyclic erythromycin derivatives.

SUMMARY OF THE INVENTION

The present invention provides a novel class of bicyclic 9a-azalide compounds, or pharmaceutically-acceptable salts, esters, or prodrugs thereof. The present invention further relates to pharmaceutical compositions, comprising the compounds of the present invention, for administration to a subject in need of antibiotic treatment. The invention also relates to methods of treating a bacterial infection in a subject by administering a pharmaceutical composition comprising the compounds of the present invention. The invention further includes process by which to make the compounds of the present invention.

The present invention disclosed compounds of formulae I and II:

(I)

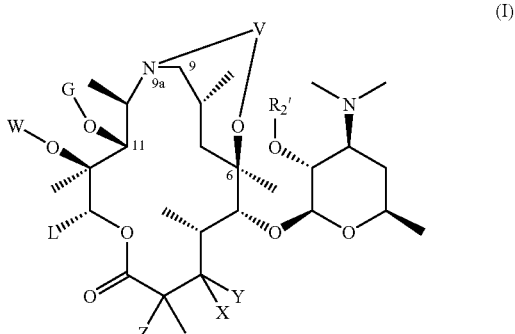

(II)

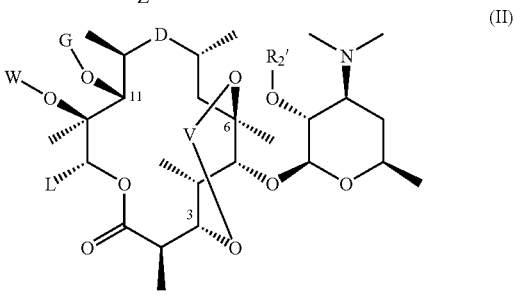

as well as the pharmaceutically acceptable salts, esters and prodrugs thereof, wherein V is selected from the group consisting of:

(a) —CH$_2$—C(A)=C(B)—CH$_2$—;
wherein,
A and B are independently selected from the group consisting of:
(i) hydrogen;
(ii) deuterium;
(iii) halogen;
(iv) R$_1$, wherein R$_1$ is dependently selected from C$_1$-C$_6$ alkyl, C$_2$-C$_6$ alkenyl, or C$_2$-C$_6$ alkynyl, containing 0, 1, 2 or 3 heteroatoms selected from O, S or N, optionally substituted with one or more substituents selected from the group consisting of: halogen, aryl, substituted aryl, heteroaryl, and substituted heteroaryl;
(v) R$_2$, wherein R$_2$ is independently selected from the group consisting of:
a. aryl;
b. heteroaryl;
c. substituted aryl; and
d. substituted heteroaryl;
(vi) —C$_1$-C$_3$-alkyl)-M-(C$_1$-C$_3$-alkyl)-R$_2$, wherein M=-O—, —NH—, —N(CH$_3$)—, —NHC(O)— or —S(O)$_n$—, wherein n=0, 1 or 2, and R$_2$ is as previously defined;
(vii) —C$_1$-C$_3$-alkyl)-M-R$_2$, wherein M and R$_2$ are as previously defined;
(viii) —C(O)-J-R$_3$, wherein J is absent, O or S, and R$_3$ is H, R$_1$ or R$_2$; where R$_1$ and R$_2$ are as previously defined, and
(ix) —C(O)—NR$_4$R$_5$, wherein R$_4$ and R$_5$ are each independently selected from the group consisting of:
a. hydrogen;
b. R$_1$, wherein R$_1$ is as previously defined;
c. R$_2$, wherein R$_2$ is as previously defined; and
d. R$_4$ and R$_5$ taken together with the nitrogen atom to which they are connected form a 3- to 7-membered ring which may optionally contain one or more heterofunctions selected from the group consisting of: —O—, —NH—, —N(R1)—, —N(R$_2$)—, —S(O)$_n$—, wherein n, R$_1$ and R$_2$ are as previously defined;
(b) —CH$_2$—CH(A)-C(B)=CH—, wherein A and B are as previously defined;
(c) —CH=C(A)-CH(B)-CH$_2$—, wherein A and B are as previously defined;
(d) —CH$_2$—CH(A')-CH(B')-CH$_2$—;
wherein A' and B' are independently selected from the group consisting of:
(i) A, wherein A is as previously defined;
(ii) —OH;
(iii) —OR$_p$, wherein R$_p$ is a hydroxy protecting group;
(iv) —O—R$_9$, wherein R$_9$ is R$_1$ or R$_2$, and wherein R$_1$ and R$_2$ are as previously defined;
(v) —S(O)$_n$R$_9$, wherein n and R$_9$ are as previously defined;
(vi) —NHC(O)R$_3$, wherein R$_3$ is as previously defined;
(vii) —NHC(O)NR$_4$R$_5$, wherein R$_4$ and R$_5$ are as previously defined;
(viii) —NHS(O)$_2$R$_9$, wherein R$_9$ is as previously defined;
(ix) —NHR$_{13}$, wherein R$_{13}$ is an amino protecting group; and
(x) —NR$_4$R$_5$, wherein R$_4$ and R$_5$ are as previously defined;

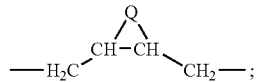

(e)

wherein:
(i) -Q- is selected from the group consisting of: —O—; —O—C(O)—CH(R$_7$)—; —N(R$_7$)—; —O—C(O)—N(R$_7$)—; —O—C(O)—O—; —N(R$_7$)—N=N—; —C(R$_7$)=N—O—; and —CH(R$_7$)—N(R$_8$)—O—; wherein R$_7$ and R$_8$ are independently selected from R$_3$, wherein R$_3$ is as previously defined; or
(ii) -Q- taken together with the two carbon atoms it is attached to is selected from the group consisting of:
a. cycloalkylene;
b. cycloalkenylene; and
c. heterocycloalkylene; and (f) —CH$_2$—C(R$_{11}$)(R$_{12}$)—CH$_2$—CH$_2$—;
wherein R$_{11}$ and R$_{12}$ taken together with the carbon atom to which they are attached are selected from the group consisting of:
(i) C=O;
(ii) C(OR$_{1a}$)(OR$_{2a}$), where R$_{1a}$ and R$_{2a}$ are independently R$_1$ or taken together are —(CH$_2$)$_m$—, and where m is 2 or 3;
(iii) C(SR$_{1a}$)(SR$_{2a}$), where R$_{1a}$ and R$_{2a}$ are previously defined;
(iv) C=CHR$_3$, where R$_3$ is as previously defined;
(v) C=N—O—R$_3$, where R$_3$ is as previously defined;
(vi) C=NNHR$_3$, where R$_3$ is as previously defined;
(vii) C=NNHC(O)R$_3$, where R$_3$ is as previously defined;
(viii) C=NNHC(O)NR$_4$R$_5$, where R$_4$ and R$_5$ are as previously defined;
(ix) C=NNHS(O)$_2$R$_9$, where R$_9$ is as previously defined;
(x) C=NNHR$_{13}$, where R$_{13}$ is as previously defined; and
(xi) C=NR$_9$, where R$_9$ is as previously defined;

(g) —C(R$_{14}$)(R$_{15}$)—CH$_2$—;
wherein R$_{14}$ is:
(i) —OR$_p$, where R$_p$ is previously defined;
(ii) —R$_1$, where R$_1$ is as previously described;
(iii) —R$_2$, where R$_2$ is as previously described;
(iv) —OR$_1$, where R$_1$ is as previously defined;
(v) —OR$_2$, where R$_2$ is previously defined;
(vi) —S(O)$_n$R$_9$, where n and R$_9$ are as previously defined;
(vii) —NHC(O)R$_9$, where R$_9$ is as previously defined;
(viii) —NHC(O)NHR$_9$, where R$_9$ is as previously defined;
(ix) —NHS(O)$_2$R$_9$, where R$_9$ is as previously defined;
(x) —NR$_4$R$_5$, where R$_4$ and R$_5$ are as previously defined;
(xi) —NHR$_{13}$, where R$_{13}$ is previously defined;
and R$_{15}$ is:
(i) deuterium;
(ii) halogen;

(iii) —OH;
(iv) —$R_1$, where $R_1$ is as previously defined;
(v) —$R_2$, where $R_2$ is as previously defined; or
(vi) —$OR_p$, where $R_p$ is as previously defined, provided that when $R_{15}$ is halogen, —OH or $OR_p$, $R_{14}$ is $R_1$ or $R_2$, where $R_1$ and $R_2$ are previously defined;

or, alternatively, $R_{14}$ and $R_{15}$ taken together with the carbon atom to which they are attached are
   (i) C=O;
   (ii) $C(OR_{1a})(OR_{2a})$, where $R_{1a}$ and $R_{2a}$ are independently $R_1$ or taken together are —$(CH_2)_m$—, and where m is 2 or 3;
   (iii) $C(SR_{1a})(SR_{2a})$, where $R_{1a}$ and $R_{2a}$ are as previously defined;
   (iv) C=$CHR_9$, where $R_9$ is as previously defined;
   (v) C=N—O—$R_9$, where $R_9$ is as previously defined;
   (vi) C=$NNHR_9$, where $R_9$ is as previously defined;
   (vii) C=$NNHC(O)R_9$, where $R_9$ is as previously defined;
   (viii) C=$NNHC(O)NHR_9$, where $R_9$ is as previously defined;
   (ix) C=$NNHS(O)_2R_9$, where $R_9$ is as previously defined;
   (x) C=$NNHR_9$, where $R_9$ is as previously defined; or
   (xi) C=$NR_9$, where $R_9$ is as previously defined;
   (h) —$CH_2$—$C(R_{14})(R_{15})$—$CH_2$—; wherein $R_{14}$ and $R_{15}$ as previously defined;

G and W are independently selected from:
   (a) hydrogen;
   (b) $R_{10}$, where $R_{10}$ is $C_1$-$C_6$-alkyl, $C_2$-$C_6$-alkenyl or $C_2$-$C_6$-alkynyl, containing 0, 1, 2, or 3 heteroatoms, optionally substituted with one or more substituents selected from:
      (1) halogen;
      (2) aryl;
      (3) substituted-aryl;
      (4) heteroaryl;
      (5) substituted-heteroaryl;
      (6) —O—$C_1$-$C_6$-alkyl-$R_9$, where $R_9$ is as previously defined; and
      (7) —$N(R_4R_5)$, where $R_4$ and $R_5$ are as previously defined;
   (c) —$C(O)R_9$, where $R_9$ is as previously defined;
   (d) —$C(O)O$—$R_9$, where $R_9$ is as previously defined; and
   (e) —$C(O)N(R_4R_5)$, where $R_4$ and $R_5$ are as previously defined;

Or, alternatively, G and W are taken together to form either a carbonyl or a methylene group.

L is
   (a) —$CH_2CH_3$;
   (b) —$CH(OH)CH_3$;
   (c) —$R_1$, where $R_1$ is as previously defined.

D is —$N(R_{19})CH_2$—, —$N(R_{20})C(O)$—, or —N=C$(OR_{20})$—, wherein $R_{20}$ is $R_9$ where $R_9$ is as previously defined;

$R_{19}$ is
   (a) hydrogen;
   (b) —$C_1$-$C_{12}$-alkyl, $C_2$-$C_{12}$-alkenyl, or $C_2$-$C_{12}$-alkynyl, containing 0, 1, 2, or 3 heteroatoms, all optionally substituted with one or more substituents independently selected from:
      i) halogen;
      ii) —$OR_1$, wherein $R_1$ is as previously defined;
      iii) —$OR_2$, wherein $R_2$ is as previously defined;
      iv) —$NR_4R_5$, where $R_4$ and $R_5$ as previously defined or alternatively $R_4$ and $R_5$, together with the atom to which they are attached, form a heterocycloalkyl or substituted heterocycloalkyl moiety;
   v) =N—O—$R_9$, where $R_9$ is as previously defined;
   vi) —$R_1$, where $R_1$ is as previously defined;
   vii) —$C_3$-$C_8$-cycloalkyl;
   viii) substituted —$C_3$-$C_8$-cycloalkyl;
   ix) heterocycloalkyl;
   x) substituted heterocycloalkyl;
   xi) —$NHC(O)R_9$, where $R_9$ is as previously defined;
   xii) —$NHC(O)OR_9$, where $R_9$ is as previously defined;
   xiii) —$NHC(O)NR_4R_5$, where $R_4$ and $R_5$ are as previously defined;
   xiv) —$OC(O)NR_4R_5$, where $R_4$ and $R_5$ are as previously defined;
   xv) —$OC(O)R_9$, where $R_9$ is as previously defined;
   xvi) —$OC(O)OR_9$, where $R_9$ is as previously defined;
   xvii) —$OC(O)NR_4R_5$, where $R_4$ and $R_5$ are as previously defined,
   xviii) —$C(O)R_9$, where $R_9$ is as previously defined,
   xix) —$CO_2R_9$, where $R_9$ is as previously defined, or
   xx) —$C(O)NR_4R_5$, where $R_4$ and $R_5$ are as previously defined;

Alternatively, D when taken together with G to form a moiety of the following structure:

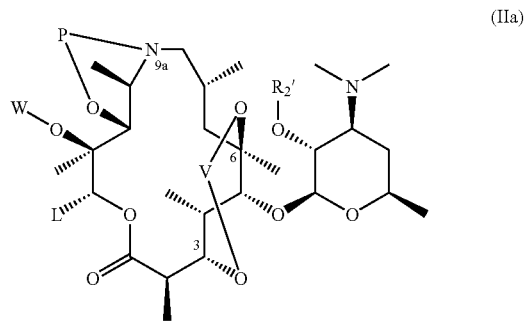

(IIa)

wherein L, V, W and $R_2$' are as previously defined and P is C1-C6 alkyl optionally substituted with one or more substituents selected from the group consisting of:
   (a) $R_1$, where $R_1$ is as previously defined;
   (b) $R_2$, where $R_2$ is as previously defined;
   (c) heterocycloalkyl,
   (d) hydroxyl,
   (e) C1-C6-alkoxy,
   (f) Halogen, and
   (g) $NR_4R_5$ where $R_4$ and $R_5$ are as previously defined.

X is hydrogen;

Y is
   (a) hydrogen;
   (b) —OH;
   (c) —$OR_p$, where $R_p$ is as previously defined;
   (d) —$OR_9$, where $R_9$ is as previously defined;
   (e) —$OC(O)R_9$, where $R_9$ is as previously defined;
   (f) —$OC(O)NHR_9$, where $R_9$ is as previously defined;
   (g) —$S(O)_nR_9$, where n and $R_9$ are as previously defined;

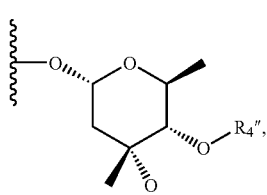

(h)

where $R_3''$ is selected from hydrogen or methyl and $R_4''$ is selected from:
(1) hydrogen;
(2) $R_p$, where $R_p$ is as previously defined; or
(3) —C(O)(CH$_2$)$_r$-E-R$_9$, wherein $R_9$ is as previously defined, r=1-6 and E is absent or —U(CH$_2$)$_q$U'—, where q=an integer from 2 to 8, and U and U' are independently selected from:
   i) —N(R$_9$)—, where $R_9$ is as previously defined;
   ii) —O—;
   iii) —S(O)$_n$—, where n=0, 1, or 2;
   iv) —N(R$_9$)C(O)—, where $R_9$ is as previously defined;
   v) —C(O)N(R$_9$)—, where $R_9$ is as previously defined; or
   vi) —N[C(O)R$_9$]—, where $R_9$ is as previously defined; and Alternatively, X and Y taken together are oxo;

Z is
   (a) hydrogen;
   (b) methyl; or
   (c) halogen; and $R_2'$ is hydrogen or $R_p$, where $R_p$, is as previously defined.

In another embodiment of the present invention there are disclosed pharmaceutical compositions comprising a therapeutically effective amount of a compound of the invention in combination with a pharmaceutically acceptable carrier or excipient. In yet another embodiment of the invention are methods of treating antibacterial infections in a subject in need of such treatment with said pharmaceutical compositions. Suitable carriers and formulations of the compounds of the present invention are disclosed.

DETAILED DESCRIPTION OF THE INVENTION

A first embodiment of the present invention is a compound of formulae (I) and (II) as illustrated above, or a pharmaceutically acceptable salt, ester or prodrug thereof.

Preferred subgenera of the present invention are:

A compound of formula III:

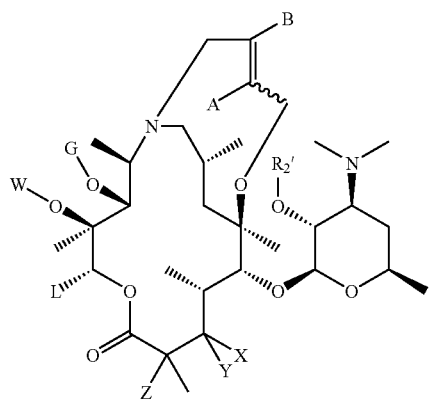

(III)

where A, B, G, L, W, X, Y, Z and $R_2'$ are as previously defined.

A compound of formulae IVa and IVb:

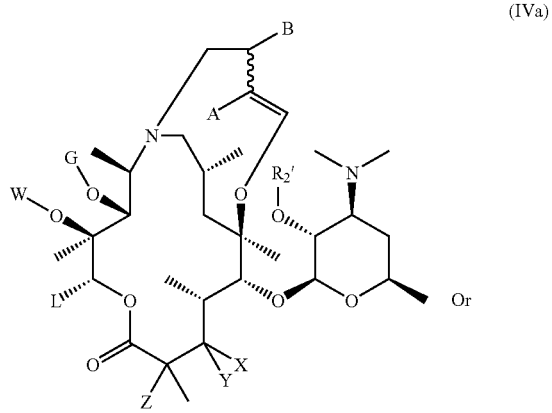

(IVa)

Or (IVb)

where A, B, G, L, W, X, Y, Z and $R_2'$ are as previously defined;

A compound of formula V:

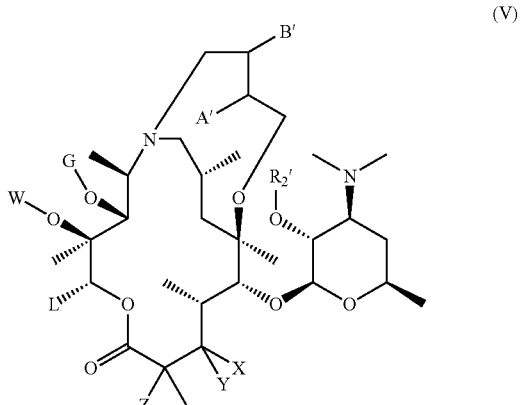

(V)

where A', B', G, L, W, X, Y, Z, and $R_2'$ are as previously defined;

A compound of formula VI:

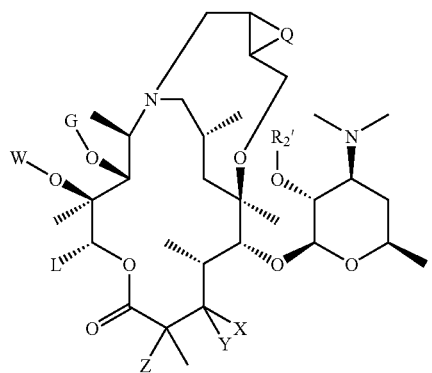
(VI)

where G, L, Q, W, X, Y, Z, and $R_2'$ are as previously defined;

A compound of formulae VIIa and VIIb:

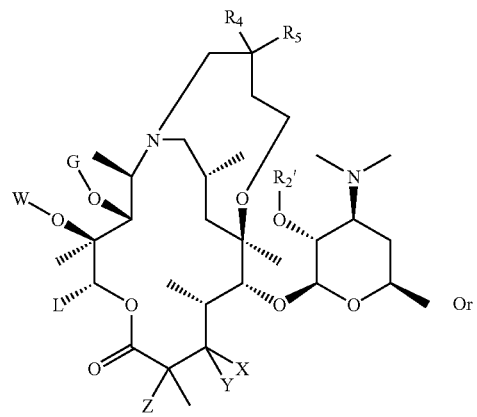
(VIIa)

Or

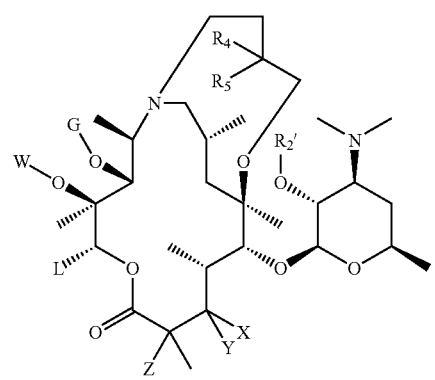
(VIIb)

where G, L, W, X, Y, Z, $R_2'$, and $R_4$ and $R_5$ are as previously defined; and A compound of formula VIII:

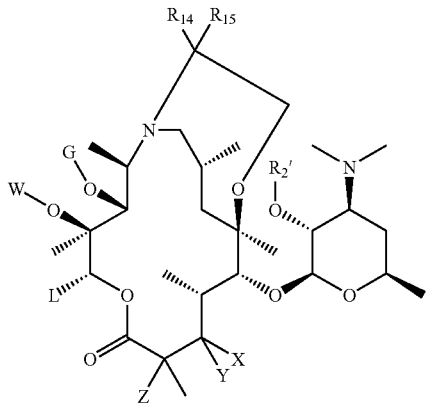
(VIII)

where G, L, W, X, Y, Z, $R_{14}$, $R_{15}$ and $R_2'$ are as previously defined.

A compound of formula IX:

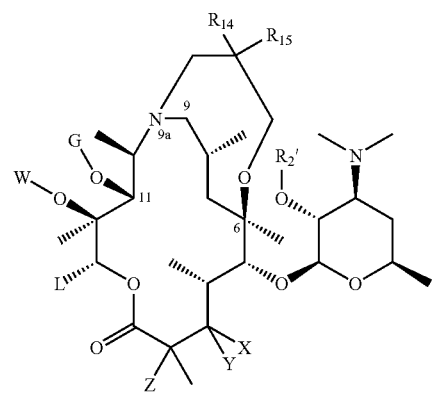
(IX)

where G, L, W, X, Y, Z, $R_{14}$, $R_{15}$ and $R_2'$ are as previously defined.

A compound of formula X:

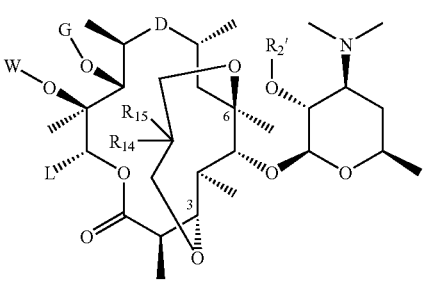
(X)

where D, G, L, W, $R_{14}$, $R_{15}$ and $R_2'$ are as previously defined.

A compound of formula XI:

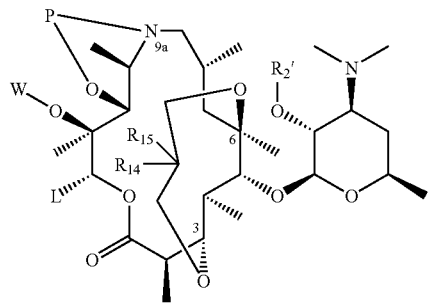

where L, P, W, $R_{14}$, $R_{15}$ and $R_2'$ are as previously defined.

A compound of formula XII:

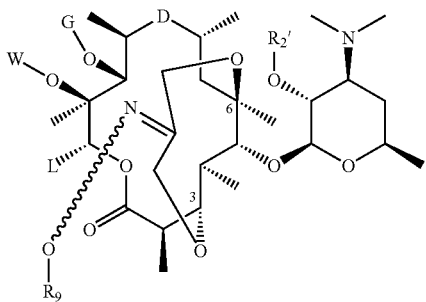

where D, L, P, W, $R_9$ and $R_2'$ are as previously defined.

A compound of formula XIII:

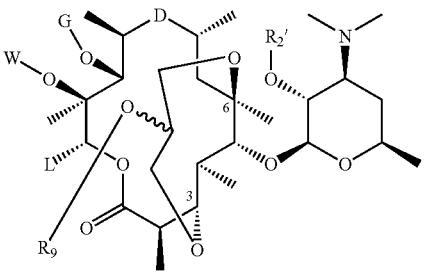

where D, L, P, W, $R_9$ and $R_2'$ are as previously defined.

Representative compounds according to the invention are those selected from:

(a) Compound of formula III, wherein A=B=G=W=Y=Z=hydrogen, L is —CH$_2$CH$_3$, $R_2'$=Ac,

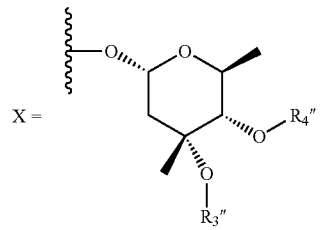

where $R_3''$ is —CH$_3$ and $R_4''$=Ac;

(b) Compound of formula III, wherein A=B=G=W=Y=Z=$R_2'$=hydrogen, L is —CH$_2$CH$_3$,

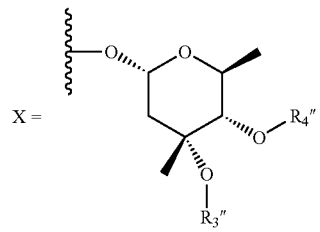

where $R_3''$ is —CH$_3$ and $R_4''$=Ac;

(c) Compound of formula III, wherein A=B=G=W=Y=Z=$R_2'$=hydrogen, L is —CH$_2$CH$_3$,

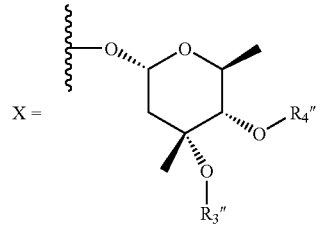

where $R_3''$ is —CH$_3$ and $R_4''$=H;

(d) Compound of formula III, wherein A=B=G=W=X=Y=Z=$R_2'$=hydrogen, L is —CH$_2$CH$_3$;

(e) Compound of formula VIII, wherein $R_{14}$ and $R_{15}$ taken together with the carbon atom to which they are attached are CHCH=CH$_2$, G=W=Y=Z=hydrogen, L is —CH$_2$CH$_3$, $R_2'$=Ac,

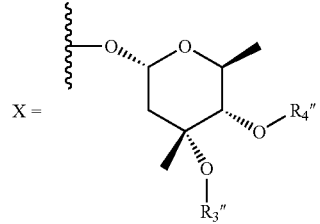

where $R_3''$ is —CH$_3$ and $R_4''$=Ac;

(f) Compound of formula VIII, wherein $R_{14}$ and $R_{15}$ taken together with the carbon atom to which they are attached are CHCH=$CH_2$, G=W=Y=Z=$R_2$'=hydrogen, L is $CH_2CH_3$,

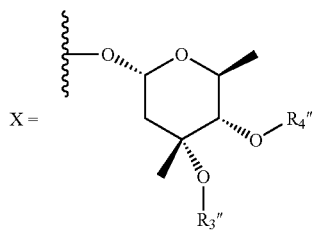

where $R_3$" is —$CH_3$ and $R_4$"=Ac;

(g) Compound of formula VIII, wherein $R_{14}$ and $R_{15}$ taken together with the carbon atom to which they are attached are CHCH=$CH_2$, $R_{15}$=G=W=Y=Z=$R_2$'=hydrogen, L is —$CH_2CH_3$,

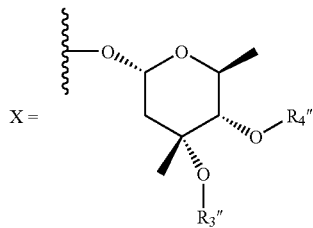

where $R_3$" is —$CH_3$ and $R_4$"=H;

(h) Compound of formula IX, wherein $R_{14}$ and $R_{15}$ taken together with the carbon atom to which they are attached are C=$CH_2$, G=W=Y=Z=hydrogen, L is —$CH_2CH_3$, $R_2$'=Ac,

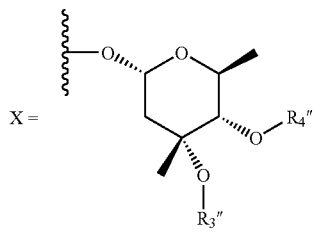

where $R_3$" is —$CH_3$ and $R_4$"=Ac;

(i) Compound of formula IX, wherein $R_{14}$ and $R_{15}$ taken together with the carbon atom to which they are attached are C=$CH_2$, G=W=Y=Z=$R_2$'=hydrogen, L is —$CH_2CH_3$,

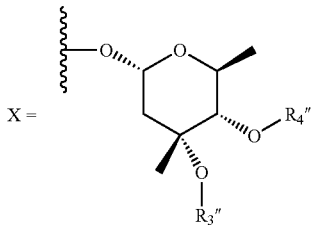

where $R_3$" is —$CH_3$ and $R_4$"=Ac;

(j) Compound of formula X, wherein $R_{14}$ and $R_{15}$ taken together with the carbon atom to which they are attached are C=$CH_2$, G=W=hydrogen, $R_2$'=Ac, L is —$CH_2CH_3$, D=-$NHCH_2$—;

(k) Compound of formula X, wherein $R_{14}$ and $R_{15}$ taken together with the carbon atom to which they are attached are C=$CH_2$, G=W=hydrogen, $R_2$'=Ac, L is —$CH_2CH_3$, D=-N($CH_3$)$CH_2$—;

(l) Compound of formula X, wherein $R_{14}$ and $R_{15}$ taken together with the carbon atom to which they are attached are C=$CH_2$, G=W=$R_2$'=hydrogen, L is —$CH_2CH_3$, D=-N($CH_3$)$CH_2$—;

(m) Compound of formula X, wherein $R_{14}$ and $R_{15}$ taken together with the carbon atom to which they are attached are C=CH-[5-(2-(2-pyridyl)thiophene)], G=W=$R_2$'=hydrogen, L is —$CH_2CH_3$, D=-N($CH_3$)$CH_2$—;

(n) Compound of formula X, wherein $R_{14}$ and $R_{15}$ taken together with the carbon atom to which they are attached are C=O, G=W=$R_2$'=hydrogen, L is —$CH_2CH_3$, D=-N($CH_3$)$CH_2$—;

(o) Compound of formula X, wherein $R_{14}$ and $R_{15}$ taken together with the carbon atom to which they are attached are C=N—O—$CH_2$-[5-(2-(1-pyrazolyl)pyridine)], G=W=$R_2$'=hydrogen, L is —$CH_2CH_3$, D=-N($CH_3$)$CH_2$—;

(p) Compound of formula X, wherein $R_{14}$ and $R_{15}$ taken together with the carbon atom to which they are attached are CH—OH, G=W=$R_2$'=hydrogen, L is —$CH_2CH_3$, D=-N($CH_3$)$CH_2$—;

(q) Compound of formula X, wherein $R_{14}$ and $R_{15}$ taken together with the carbon atom to which they are attached are CH—O—$CH_2$C≡CH, G=W=$R_2$'=hydrogen, L is —$CH_2CH_3$, D=-N($CH_3$)$CH_2$—;

(r) Compound of formula X, wherein $R_{14}$ and $R_{15}$ taken together with the carbon atom to which they are attached are CH—O—$CH_2$C≡C-[5-(2-(2-pyridyl)thiophene)], G=W=$R_2$'=hydrogen, L is —$CH_2CH_3$, D=-N($CH_3$)$CH_2$—;

(s) Compound of formula X, wherein $R_{14}$ and $R_{15}$ taken together with the carbon atom to which they are attached are CH—O—$CH_2$CH=CH-[5-(2-(2-pyridyl)thiophene)], G=W=$R_2$'=hydrogen, L is —$CH_2CH_3$, D=-N($CH_3$)$CH_2$—;

(t) Compound of formula XI, wherein $R_{14}$ and $R_{15}$ taken together with the carbon atom to which they are attached are C=CH$_2$, G=W=hydrogen, $R_2$'=Ac, L is —CH$_2$CH$_3$, P=CH$_2$;

(u) Compound of formula XI, wherein $R_{14}$ and $R_{15}$ taken together with the carbon atom to which they are attached are C=O, G=W=$R_2$'=hydrogen, L is —CH$_2$CH$_3$, P=CH$_2$;

(v) Compound of formula XI, wherein $R_{14}$ and $R_{15}$ taken together with the carbon atom to which they are attached are C=CH-[5-(2-(2-pyridyl)thiophene)], G=W=$R_2$'=hydrogen, L is —CH$_2$CH$_3$, P=CH$_2$;

(w) Compound of formula XI, wherein $R_{14}$ and $R_{15}$ taken together with the carbon atom to which they are attached are C=N—O—CH$_2$-[5-(2-(1-pyrazolyl)pyridine)], G=W=$R_2$'=hydrogen, L is —CH$_2$CH$_3$, P=CH$_2$;

(x) Compound of formula XI, wherein $R_{14}$ and $R_{15}$ taken together with the carbon atom to which they are attached are CH—O—CH$_2$CCH, G=W=$R_2$'=hydrogen, L is —CH$_2$CH$_3$, P=CH$_2$;

(y) Compound of formula XI, wherein $R_{14}$ and $R_{15}$ taken together with the carbon atom to which they are attached are CH—O—CH$_2$C≡C-[5-(2-(2-pyridyl)thiophene)], G=W=$R_2$'=hydrogen, L is —CH$_2$CH$_3$, P=CH$_2$;

(z) Compound of formula XI, wherein $R_{14}$ and $R_{15}$ taken together with the carbon atom to which they are attached are CH—O—CH$_2$CH=CH-[5-(2-(2-pyridyl)thiophene)], G=W=$R_2$'=hydrogen, L is —CH$_2$CH$_3$, P=CH$_2$;

(aa) Compound of formula X, wherein $R_{14}$ and $R_{15}$ taken together with the carbon atom to which they are attached are CH—O—CH$_2$CH=CH-(3-quinoline), G=W=$R_2$'=hydrogen, L is —CH$_2$CH$_3$, D=-N(CH$_3$)CH$_2$—;

(bb) Compound of formula XI, wherein $R_{14}$ and $R_{15}$ taken together with the carbon atom to which they are attached are CH—OH, W=$R_2$'=hydrogen, L is —CH$_2$CH$_3$, P=CH$_2$C(=CH$_2$)CH$_2$;

(cc) Compound of formula XI, wherein $R_{14}$ and $R_{15}$ taken together with the carbon atom to which they are attached are CH—OH, W=$R_2$'=hydrogen, L is —CH$_2$CH$_3$, P=CH(CH=CH$_2$)CH$_2$.

A further embodiment of the present invention includes pharmaceutical compositions comprising any single compound delineated herein, or a pharmaceutically acceptable salt, ester, or prodrug thereof, with a pharmaceutically acceptable carrier or excipient.

Yet another embodiment of the present invention is a pharmaceutical composition comprising a combination of two or more compounds delineated herein, or a pharmaceutically acceptable salt, ester, or prodrug thereof, with a pharmaceutically acceptable carrier or excipient.

Yet a further embodiment of the present invention is a pharmaceutical composition comprising any single compound delineated herein in combination with one or more antibiotics known in the art, or a pharmaceutically acceptable salt, ester, or prodrug thereof, with a pharmaceutically acceptable carrier or excipient.

In addition, the present invention contemplates processes of making any compound delineated herein via any synthetic method delineated herein.

Definitions

Listed below are definitions of various terms used to describe this invention. These definitions apply to the terms as they are used throughout this specification and claims, unless otherwise limited in specific instances, either individually or as part of a larger group.

An "aliphatic group" is non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may be used in place of the alkyl groups described herein.

The terms "$C_1$-$C_3$ alkyl," "$C_1$-$C_6$ alkyl," or "$C_1$-$C_{12}$ alkyl," as used herein, refer to saturated, straight- or branched-chain hydrocarbon radicals containing between one and three, one and twelve, or one and six carbon atoms, respectively. Examples of $C_1$-$C_3$ alkyl radicals include methyl, ethyl, propyl and isopropyl radicals; examples of $C_1$-$C_6$ alkyl radicals include, but are not limited to, methyl, ethyl, propyl, propyl, butyl, pentyl, and hexyl radicals; and examples of $C_1$-$C_{12}$ alkyl radicals include, but are not limited to, ethyl, propyl, propyl, hexyl, heptyl, octyl, nonyl, decyl, undecyl, dodecyl radicals and the like.

The term "substituted alkyl," as used herein, refers to an alkyl, such as a $C_1$-$C_{12}$ alkyl or $C_1$-$C_6$ alkyl group, substituted by one, two, three or more aliphatic or aromatic substituents.

Suitable aliphatic or aromatic substituents include, but are not limited to, —F, —Cl, —Br, —I, —OH, protected hydroxy, aliphatic ethers, aromatic ethers, oxo, —NO$_2$, —CN, —$C_1$-$C_{12}$-alkyl optionally substituted with halogen (such as perhaloalkyls), $C_2$-$C_{12}$-alkenyl optionally substituted with halogen, —$C_2$-$C_{12}$-alkynyl optionally substituted with halogen, —NH$_2$, protected amino, —NH—$C_1$-$C_{12}$-alkyl, —NH—$C_2$-$C_{12}$-alkenyl, —NH—$C_2$-$C_{12}$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkynyl, —C(O)—$C_3$-$C_{12}$-cycloalkyl, —C(O)-aryl, —C(O)-heteroaryl, —C(O)-heterocycloalkyl, —CONH$_2$, —CONH—$C_1$-$C_{12}$-alkyl, —CONH—$C_2$-$C_{12}$-alkenyl, —CONH—$C_2$-$C_{12}$-alkynyl, —CONH—$C_3$-$C_{12}$-cycloalkyl, —CONH-aryl, —CONH-heteroaryl, —CONH-heterocycloalkyl, —CO$_2$—$C_1$-$C_{12}$-alkyl, —CO$_2$—$C_2$-$C_{12}$-alkenyl, —CO$_2$—$C_2$-$C_{12}$-alkynyl, —CO$_2$—$C_3$-$C_{12}$-cycloalkyl, —CO$_2$-aryl, —CO$_2$-heteroaryl, —CO$_2$-heterocycloalkyl, —OCO$_2$—$C_1$-$C_{12}$-alkyl, —OCO$_2$—$C_2$-$C_{12}$-alkenyl, —OCO$_2$—$C_2$-$C_{12}$-alkynyl, —OCO$_2$—$C_3$-$C_{12}$-cycloalkyl, —OCO$_2$-aryl, —OCO$_2$-heteroaryl, —OCO$_2$-heterocycloalkyl, —OCONH$_2$, —OCONH—$C_1$-$C_{12}$-alkyl, —OCONH—$C_2$-$C_{12}$-alkenyl, —OCONH—$C_2$-$C_{12}$-alkynyl, —OCONH—$C_3$-$C_{12}$-cycloalkyl, —OCONH-aryl, —OCONH-heteroaryl, —OCONH-heterocycloalkyl, —NHC(O)—$C_1$-$C_{12}$-alkyl, —NHC(O)—$C_2$-$C_{12}$-alkenyl, —NHC(O)—$C_2$-$C_{12}$-alkynyl, —NHC(O)—$C_3$-$C_{12}$-cycloalkyl, —NHC(O)-aryl, —NHC(O)-heteroaryl, —NHC(O)-heterocycloalkyl, —NHCO$_2$—C$_1$-C$_{12}$-alkyl, —NHCO$_2$—C$_2$-C$_{12}$-alkenyl, —NHCO$_2$—C$_2$-C$_{12}$-alkynyl, —NHCO$_2$—C$_3$-C$_{12}$-cycloalkyl, —NHCO$_2$-aryl, —NHCO$_2$-heteroaryl, —NHCO$_2$-heterocycloalkyl, —NHC(O)NH$_2$, NHC(O)NH—C$_1$-C$_{12}$-alkyl, —NHC(O)NH—C$_2$-C$_{12}$-alkenyl, —NHC(O)NH—C$_2$-C$_{12}$-alkynyl, —NHC(O)NH—C$_3$-C$_{12}$-cycloalkyl, —NHC(O)NH-aryl, —NHC(O)NH-heteroaryl, —NHC(O)NH-heterocycloalkyl, NHC(S)NH$_2$, NHC(S)NH—C$_1$-C$_{12}$-alkyl, —NHC(S)NH—C$_2$-C$_{12}$-alkenyl, —NHC(S)NH—C$_2$-C$_{12}$-alkynyl, —NHC(S)NH—C$_3$-C$_{12}$-cycloalkyl, —NHC(S)NH-aryl, —NHC(S)NH-heteroaryl, —NHC(S)NH-heterocycloalkyl, —NHC(NH)NH$_2$, NHC(NH)NH—C$_1$-C$_{12}$-alkyl, —NHC(NH)NH—C$_2$-C$_{12}$-alkenyl, —NHC(NH)NH—C$_2$-C$_{12}$-alkynyl, —NHC(NH)NH—C$_3$-C$_{12}$-cycloalkyl, —NHC(NH)NH-aryl, —NHC(NH)NH-heteroaryl, —NHC(NH)NH-heterocycloalkyl, NHC(NH)—C$_1$-C$_{12}$-alkyl, —NHC(NH)—C$_2$-C$_{12}$-alkenyl, —NHC(NH)—C$_2$-C$_{12}$-alkynyl, —NHC(NH)—C$_3$-C$_{12}$-cycloalkyl, —NHC(NH)-aryl, —NHC(NH)-heteroaryl, —NHC(NH)-heterocycloalkyl, —C(NH)NH—C$_1$-C$_{12}$-alkyl, —C(NH)NH—C$_2$-C$_{12}$-alkenyl, —C(NH)NH—C$_2$-C$_{12}$-alkynyl, —C(NH)NH—C$_3$-C$_{12}$-cycloalkyl, —C(NH)NH-aryl, —C(NH)NH-heteroaryl, —C(NH)NH-heterocycloalkyl, —S(O)—C$_1$-C$_{12}$-alkyl, —S(O)—C$_2$-C$_{12}$-alkenyl, —S(O)—C$_2$-C$_{12}$-alkynyl, —S(O)—C$_3$-C$_{12}$-cycloalkyl, —S(O)-aryl, —S(O)-heteroaryl, —S(O)-heterocycloalkyl —SO$_2$NH$_2$, —SO$_2$NH—C$_1$-C$_{12}$-alkyl, —SO$_2$NH—C$_2$-C$_{12}$-alkenyl, —SO$_2$NH—C$_2$-C$_{12}$-alkynyl, —SO$_2$NH—C$_3$-C$_{12}$-cycloalkyl, —SO$_2$NH-aryl, —SO$_2$NH-heteroaryl, —SO$_2$NH-heterocycloalkyl, —NHSO$_2$—C$_1$-C$_{12}$-alkyl, —NHSO$_2$—C$_2$-C$_{12}$-alkenyl, —NHSO$_2$—C$_2$-C$_{12}$-alkynyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_{12}$-alkenyl, —S—C$_2$-C$_{12}$-alkynyl, —S—C$_3$-C$_{12}$-cycloalkyl, —S-aryl, —S-heteroaryl, —S-heterocycloalkyl, or methylthiomethyl. It is understood that the aryls, heteroaryls, alkyls and the like can be further substituted.

The terms "C$_2$-C$_{12}$ alkenyl" or "C$_2$-C$_6$ alkenyl," as used herein, denote a monovalent group derived from a hydrocarbon moiety containing from two to twelve or two to six carbon atoms having at least one carbon-carbon double bond by the removal of a single hydrogen atom. Alkenyl groups include, but are not limited to, for example, ethenyl, propenyl, butenyl, 1-methyl-2-buten-1-yl, alkadienes and the like.

The term "substituted alkenyl," as used herein, refers to a "C$_2$-C$_{12}$ alkenyl" or "C$_2$-C$_6$ alkenyl" group as previously defined, substituted by one, two, three or more aliphatic substituents.

The terms "C$_2$-C$_{12}$ alkynyl" or "C$_2$-C$_6$ alkynyl," as used herein, denote a monovalent group derived from a hydrocarbon moiety containing from two to twelve or two to six carbon atoms having at least one carbon-carbon triple bond by the removal of a single hydrogen atom. Representative alkynyl groups include, but are not limited to, for example, ethynyl, 1-propynyl, 1-butynyl, and the like.

The term "substituted alkynyl," as used herein, refers to a "C$_2$-C$_{12}$ alkynyl" or "C$_2$-C$_6$ alkynyl" group as previously defined, substituted by one, two, three or more aliphatic substituents.

The term "C$_1$-C$_6$ alkoxy," as used herein, refers to a C$_1$-C$_6$ alkyl group, as previously defined, attached to the parent molecular moiety through an oxygen atom. Examples of C$_1$-C$_6$-alkoxy include, but are not limited to, methoxy, ethoxy, propoxy, isopropoxy, n-butoxy, sec-butoxy, tert-butoxy, n-pentoxy, neopentoxy and n-hexoxy.

The terms "halo" and "halogen," as used herein, refer to an atom selected from fluorine, chlorine, bromine and iodine.

The terms "aryl," or "aromatic" as used herein, refers to a mono- or polycyclic carbocyclic ring system having one, two or more aromatic rings including, but not limited to, phenyl, naphthyl, tetrahydronaphthyl, indanyl, idenyl and the like.

The terms "substituted aryl" or "substituted aromatic," as used herein, refer to an aryl group, as previously defined, substituted by one, two, three or more aromatic substituents.

The term "arylalkyl," as used herein, refers to an aryl group attached to the parent compound via a C$_1$~C$_3$ alkyl or C$_1$~C$_6$ alkyl residue. Examples include, but are not limited to, benzyl, phenethyl and the like.

The term "substituted arylalkyl," as used herein, refers to an arylalkyl group, as previously defined, substituted by one, two, three or more aromatic substituents.

The terms "heteroaryl" or "heteroaromatic" as used herein, refers to a mono- or polycyclic (e.g. bi-, or tri-cyclic or more) aromatic radical or ring having from five to ten ring atoms of which one or more ring atom is selected from, for example, S, O and N; zero, one or two ring atoms are additional heteroatoms independently selected from, for example, S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The terms "substituted heteroaryl" or "substituted heteroaromatic," as used herein, refer to a heteroaryl group as previously defined, substituted by one, two, three or more aromatic substituents.

In accordance with the invention, any of the aryls, substituted aryls, heteroaryls and substituted heteroaryls described herein, can be any aromatic group. Aromatic groups can be substituted or unsubstituted.

The term "alicyclic," as used herein, denotes a monovalent group derived from a monocyclic or bicyclic saturated carbocyclic ring compound by the removal of a single hydrogen atom. Examples include, but are not limited to, cyclopropyl, cyclobutyl, cyclopentyl, cyclohexyl, bicyclo [2.2.1] heptyl, and bicyclo [2.2.2] octyl.

The term "substituted alicyclic" group as previously defined, substituted by one, two, three or more aliphatic substituents.

The term "heterocyclic" as used herein, refers to a non-aromatic 5-, 6- or 7-membered ring or a bi- or tri-cyclic group fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, (iv) any of the above rings may be fused to a benzene ring, and (v) the remaining ring atoms are carbon atoms which may be optionally oxo-substituted. Representative heterocycloalkyl groups include, but are not limited to, [1,3] dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl. Such heterocyclic groups may be further substituted to give substituted heterocyclic.

The term "substituted heterocyclic," as used herein, refers to a heterocyclic group, as previously defined, substituted by one, two, three or more aliphatic substituents.

The term "heteroarylalkyl," as used herein, refers to a heteroaryl group attached to the parent compound via a $C_1$-$C_3$ alkyl or $C_1$-$C_6$ alkyl residue. Examples include, but are not limited to, pyridinylmethyl, pyrimidinylethyl and the like.

The term "substituted heteroarylalkyl," as used herein, refers to a heteroarylalkyl group, as previously defined, substituted by independent replacement of one, two, or three or more aromatic substituents.

The term "$C_1$-$C_3$-alkylamino," as used herein, refers to one or two $C_1$-$C_3$-alkyl groups, as previously defined, attached to the parent molecular moiety through a nitrogen atom. Examples of $C_1$-$C_3$-alkylamino include, but are not limited to, methylamino, dimethylamino, ethylamino, diethylamino, and propylamino.

The term "alkylamino" refers to a group having the structure —NH($C_1$-$C_{12}$ alkyl) where $C_1$-$C_{12}$ alkyl is as previously defined.

The term "dialkylamino" refers to a group having the structure —N($C_1$-$C_{12}$ alkyl) ($C_1$-$C_{12}$ alkyl), where $C_1$-$C_{12}$ alkyl is as previously defined. Examples of dialkylamino are, but not limited to, dimethylamino, diethylamino, methylethylamino, piperidino, and the like.

The term "alkoxycarbonyl" represents an ester group, i.e., an alkoxy group, attached to the parent molecular moiety through a carbonyl group such as methoxycarbonyl, ethoxycarbonyl, and the like.

The term "carboxaldehyde," as used herein, refers to a group of formula —CHO.

The term "carboxy," as used herein, refers to a group of formula —COOH.

The term "carboxamide," as used herein, refers to a group of formula —C(O)NH($C_1$-$C_{12}$ alkyl) or —C(O)N($C_1$-$C_{12}$ alkyl) ($C_1$-$C_{12}$ alkyl), —C(O)NH$_2$, —NHC(O)($C_1$-$C_{12}$ alkyl), —N($C_1$-$C_{12}$ alkyl)C(O)($C_1$-$C_{12}$ alkyl) and the like.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, *Protective Groups in Organic Synthesis,* 3rd edition, John Wiley & Sons, New York (1999). Examples of hydroxyl protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl (trityl), tetrahydrofuryl, methoxymethyl, methylthiomethyl, benzyloxymethyl, 2,2,2-triehloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxyl protecting groups for the present invention are acetyl (Ac or —C(O)CH$_3$), benzoyl (Bz or —C(O)C$_6$H$_5$), and trimethylsilyl (TMS or —Si(CH$_3$)$_3$).

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group", as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery*, (Drugs and the Pharmaceutical Sciences; Volume 53), Marcel Dekker, Inc., New York (1992).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the are described generally in T. H. Greene and P. G. M. Wuts, *Protective Groups in Organic Synthesis,* 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

The term "protected amino," as used herein, refers to an amino group protected with an amino protecting group as defined above.

The term "acyl" includes residues derived from acids, including but not limited to carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic phosphates and aliphatic phosphates. Examples of aliphatic carbonyls include, but are not limited to, acetyl, propionyl, 2-fluoroacetyl, butyryl, 2-hydroxyl acetyl, and the like.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series,* John Wiley & Sons, NY, 1986.

The term "protogenic organic solvent" or "protic solvent," as used herein, refers to a solvent that tends to provide protons, such as an alcohol, for example, methanol, ethanol, propanol, isopropanol, butanol, t-butanol, water and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series,* John Wiley & Sons, NY, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations,* VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis,* John Wiley and Sons (1994); and L. Paquette, ed., *Encyclopedia of Reagents for Organic Synthesis,* John Wiley and Sons (1995), and subsequent editions thereof.

The term "subject" as used herein refers to an animal. Preferably the animal is a mammal. More preferably the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

The compounds described herein contain one or more asymmetric centers and thus give rise to enantiomers, diastereomers, and other stereoisomeric forms that may be defined, in terms of absolute stereochemistry, as (R)— or (S)—, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid or inorganic acid. Examples of pharmaceutically acceptable nontoxic acid addition salts include, but are not limited to, salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid lactobionic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to a compound of Formula I. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38(1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

This invention also encompasses pharmaceutical compositions containing, and methods of treating bacterial infections through administering, pharmaceutically acceptable prodrugs of compounds of the formula I. For example, compounds of formula I having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of formula I. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities.

As used herein, unless otherwise indicated, the term "bacterial infection(s)" or "protozoa infections"; includes, but is not limited to, bacterial infections and protozoa infections that occur in mammals, fish and birds as well as disorders related to bacterial infections and protozoa infections that may be treated or prevented by administering antibiotics such as the compounds of the present invention. Such bacterial infections and protozoa infections and disorders related to such infections include, but are not limited to, the following: pneumonia, otitis media, meningitis, sinusitus, bronchitis, tonsillitis, cystic fibrosis (CF) and mastoiditis related to infection by *Streptococcus pneumoniae, Haemophilus influenzae, Moraxella catarrhalis, Staphylococcus aureus, Peptostreptococcus* spp. or *Pseudomonas* spp.; pharyngitis, rheumatic fever, and glomerulonephritis related to infection by *Streptococcus pyogenes*, Groups C and G *streptococci, Clostridium diptheriae*, or *Actinobacillus haemolyticum*; respiratory tract infections related to infection by *Mycoplasma pneumoniae, Legionella pneumophila, Streptococcus pneumoniae, Haemophilus influenzae*, or *Chlamydia pneumoniae*; uncomplicated skin and soft tissue infections, abscesses and osteomyelitis, and puerperal fever related to infection by *Staphylococcus aureus*, coagulase-positive *staphylococci* (i.e., *S. epidermidis, S. hemolyticus*, etc.), *S. pyogenes, S. agalactiae, Streptococcal* groups C-F (minute-colony *streptococci*), *viridans streptococci, Corynebacterium* spp., *Clostridium* spp., or *Bartonella henselae*; uncomplicated acute urinary tract infections related to infection by *S. saprophyticus* or *Enterococcus* spp.; urethritis and cervicitis; and sexually transmitted diseases related to infection by *Chlamydia trachomatis, Haemophilus ducreyi, Treponema pallidum, Ureaplasma urealyticum,* or *Nesseria gonorrheae*; toxin diseases related to infection by *S. aureus* (food poisoning and Toxic shock syndrome), or Groups A, S. and C *streptococci*; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *C. trachomatis, N. gonorrhoeae, S. aureus, S. pneumoniae, S. pyogenes, H. influenzae,* or *Listeria* spp.; disseminated *Mycobacterium avium* complex (MAC) disease related to infection by *Mycobacterium avium*, or *Mycobacterium intracellulare*; tuberculosis disease related to infection by *Mycobacterium tuberculosis*; gastroenteritis related to infection by *Campylobacter jejuni*; intestinal protozoa related to infection by *Cryptosporidium* spp. odontogenic infection related to infection by viridans streptococci; persistent cough related to infection by *Bordetella pertussis*; gas gangrene related to infection by *Clostridium perfringens* or *Bacteroides* spp.; Skin infection by *S. aureus, Propionibacterium* acne; atherosclerosis related to infection by *Helicobacter pylori* or *Chlamydia pneumoniae*; or the like.

Bacterial infections and protozoa infections and disorders related to such infections that may be treated or prevented in animals include, but are not limited to, the following: bovine respiratory disease related to infection by *P. haemolytica., P. multocida, Mycoplasma bovis,* or *Bordetella* spp.; cow enteric disease related to infection by *E. coli* or protozoa (i.e., coccidia, cryptosporidia, etc.), dairy cow mastitis related to infection by *S. aureus, S. uberis, S. agalactiae, S. dysgalactiae, Klebsiella* spp., *Corynebacterium,* or *Enterococcus* spp.; swine respiratory disease related to infection by *A. pleuropneumoniae., P. multocida,* or *Mycoplasma* spp.; swine enteric disease related to infection by *E. coli, Lawsonia intracellularis, Salmonella* spp., or *Serpulina hyodyisinteriae*; cow footrot related to infection by *Fusobacterium* spp.; cow metritis related to infection by *E. coli*; cow hairy warts related to Infection by *Fusobacterium necrophorum* or *Bacteroides nodosus*; cow pink-eye related to infection by *Moraxella bovis*, cow premature abortion related to infection by protozoa (i.e. neosporium); urinary tract infection in dogs and cats related to infection by *E. coli*; skin and soft tissue infections in dogs and cats related to infection by *S. epidermidis, S. intermedius*, coagulase neg. *Staphylococcus* or *P. multocida*; and dental or mouth infections in dogs and oats related to infection by *Alcaligenes* spp., *Bacteroides* spp., *Clostridium* spp., *Enterobacter* spp., *Eubacterium* spp., *Peptostreptococcus* spp., *Porphfyromonas* spp., *Campylobacter* spp., *Actinomyces* spp., *Erysipelothrix* spp., *Rhodococcus* spp., *Trypanosoma* spp., *Plasmodium* spp., *Babesia* spp., *Toxoplasma* spp., *Pneumocystis* spp., *Leishmania* spp., and *Trichomonas* spp. or *Prevotella* spp. Other bacterial infections and protozoa infections and disorders related to such infections that may be treated or prevented in accord with the method of the present invention are referred to in J. P. Sanford at al., "The Sanford Guide to Antimicrobial Therapy," 26th Edition, (Antimicrobial Therapy, Inc., 1996).

Antibacterial activity studies may be carried out using suitable assays as are known in the art. Susceptibility tests can be used to quantitatively measure the in vitro activity of an antimicrobial agent against a given bacterial isolate. Compounds are tested for in vitro antibacterial activity by a microdilution method. Minimal Inhibitory Concentration (MIC) is determined in 96 well microtiter plates utilizing the appropriate Mueller Hinton Broth medium (CAMHB) for the observed bacterial isolates. Antimicrobial agents are serially diluted (2-fold) in DMSO to produce a concentration range from about 64 µg/ml to about 0.03 µg/ml. The diluted compounds (2 µl/well) are then transferred into sterile, uninoculated CAMHB (0.2 mL) by use of a 96 fixed tip-pipeting station. The inoculum for each bacterial strain is standardized to $5 \times 10^5$ CFU/mL by optical comparison to a 0.5 McFarland turbidity standard. The plates are inoculated with 10 µl/well of adjusted bacterial inoculum. The 96 well plates are covered and incubated at 35±2° C. for 24 hours in ambient air environment. Following incubation, plate wells are visually examined by Optical Density measurement for the presence of growth (turbidity). The lowest concentration of an antimicrobial agent at which no visible growth occurs is defined as the MIC. The compounds of the invention generally demonstrated an MIC in the range from about 64 µg/ml to about 0.03 µg/ml.

All in vitro testing follows the guidelines described in the Approved Standards M7-A4 protocol, published by the National Committee for Clinical Laboratory Standards (NC-CLS).

The invention further provides compositions and methods of treating subjects suffering from an inflammatory condition comprising administering to a subject in need thereof, a therapeutically effective amount of at least one compound of the invention. Specific examples of inflammatory conditions treatable according to the invention include, but are not limited to, scleritis; epi-scleritis; allergic conjunctivitis; pulmonary inflammatory diseases, particularly CF, asthma, chronic obstructive pulmonary disease (COPD), allergic bronchopulmonary aspergillosis (ABPA), and sarcoidosis; procto-sigmoiditis; allergic rhinitis; arthritis; tendonitis; apthous stomatitis; and inflammatory bowel disease.

The invention further provides compositions and methods for i) prophylactic treatment of those subjects susceptible to the symptoms CF including pulmonary infection and inflammation associated with CF, ii) treatment at the initial onset of symptoms of pulmonary infection and inflammation associated with CF, and iii) treatment of ongoing or relapsing symptoms of infection and inflammation associated with CF. In accordance with the invention a compound of the invention, is administered to a subject in need of treatment for CF, in amount sufficient to prevent, diminish or eradicate symptoms of CF including chronic pulmonary inflammation and infection.

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminun hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the subject in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to VanDevanter et al., U.S. Pat. No. 5,508,269 to Smith et al., and WO 98/43,650 by Montgomery, all of which are incorporated herein by reference). A discussion of pulmonary delivery of antibiotics is also found in U.S. Pat. No. 6,014,969, incorporated herein by reference. According to the methods of treatment of the present invention, bacterial infections, cystic fibrosis and inflammatory conditions are treated or prevented in a subject such as a human or another animal by administering to the subject a therapeutically effective amount of a compound of the invention, in such amounts and for such time as is necessary to achieve the desired result.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular subject will depend upon a variety of factors including the disorder being treated and the severity of the disorder; the activity of the specific compound employed; the specific composition employed; the age, body weight, general health, sex and diet of the subject; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a subject in need of such treatment from about 10 mg to about 1000 mg of the compound(s) of this invention per day in single or multiple doses. The compounds of the formulae described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically excipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular subject will depend upon a variety of factors, including the activity of the specific compound employed, the age, body weight, general health status, sex, diet, time of administration, rate of excretion, drug combination, the severity and course of the disease, condition or symptoms, the subject's disposition to the disease, condition or symptoms, and the judgment of the treating physician.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Subjects may, however, require intermittent treatment on a long-term basis upon any recurrence of disease symptoms. When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The pharmaceutical compositions of this invention can be administered orally to fish by blending said pharmaceutical compositions into fish feed or said pharmaceutical compositions may be dissolved in water in which infected fish are placed, a method commonly referred to as a medicated bath. The dosage for the treatment of fish differs depending upon the purpose of administration (prevention or cure of disease) and type of administration, size and extent of infection of the fish to be treated. Generally, a dosage of 5-1000 mg, preferably 20-100 mg, per kg of body weight of fish may be administered per day, either at one time or divided into several times. It will be recognized that the above-specified dosage is only a general range which may be reduced or increased depending upon the age, body weight, condition of disease, etc. of the fish.

Unless otherwise defined, all technical and scientific terms used herein are accorded the meaning commonly known to one of ordinary skill in the art. All publications, patents, published patent applications, and other references mentioned herein are hereby incorporated by reference in their entirety.

Abbreviations

Abbreviations which may appear in the following synthetic schemes and examples are:
Ac for acetyl;
AIBN for azobisisobutyronitrile;
9-BBN for 9-borabicyclo[3.3.1]nonane;
Boc for tert-butoxycarbonyl;
Bu$_3$SnH for tributyltin hydride;
Bz for benzyl;
CDI for carbonyldiimidazole;
dba for dibenzylidene acetone;
DBU for 1,8-diazabicyclo[5.4.0]undec-7-ene;
DEAD for diethylazodicarboxylate;
Dess-Martin periodinane for 1,1,1-tris(acetyloxy)-1,1-dihydro-1,2-benziodoxol-3-(1H)-one;
DIBAL for diisobutylaluminum hydride;
DMAP for dimethylaminopyridine;
DMF for dimethyl formamide;
DMSO for dimethyl sulfoxide;
DPPA for diphenylphosphoryl azide;
dppb for diphenylphosphino butane;
EtOAc for ethyl acetate;
iPrOH for isopropanol;
NaHMDS for sodium bis(trimethylsilyl)amide;
NMO for N-methylmorpholine N-oxide;
MeOH for methanol;
MOM for methoxymethyl;
PDC for pyridinium dichromate;
Ph for phenyl;
POPd for dihydrogen dichlorobis(di-tert-butylphosphino) palladium(II);
TBAHS for tetrabutyl ammonium hydrogen sulfate;
TBS for tert-butyl dimethylsilyl;
TEA for triethylamine;
TES for triethyl silyl;
THF for tetrahydrofuran;
TMS for trimethyl silyl;
TPAP for tetra-n-propyl ammonium perruthenate;
TPP for triphenylphosphine; and
Tris for Tris(hydroxymethyl)aminomethane.

Synthetic Methods

The compounds and processes of the present invention will be better understood in connection with the following synthetic schemes that illustrate the methods by which the compounds of the invention may be prepared.

A preferred intermediate for the preparation of compounds represented by formulae I and II is a compound represented by the formula Ia:

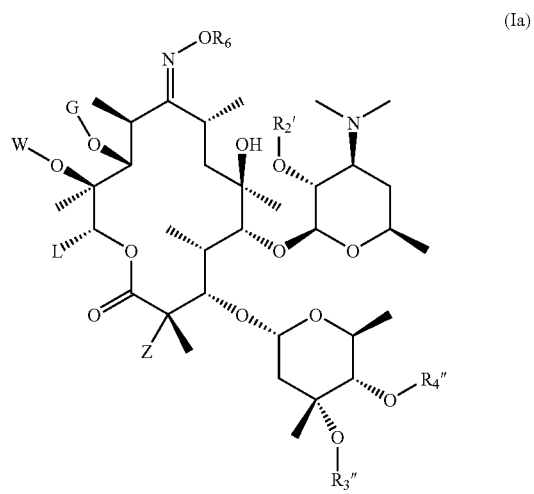

(Ia)

wherein:
1) $R_3''$ and $R_4''$ are as previously defined; and
2) $R_6$ is selected from a group consisting of:
  a. hydrogen;
  b. —$CH_2O(CH_2)_2OCH_3$;
  c. —$CH_2O(CH_2O)_nCH_3$, wherein n is as previously defined;
  d. $C_1$-$C_{12}$ alkyl, optionally substituted with one or more substituents selected from the group consisting of halogen, aryl, substituted aryl, heteroaryl and substituted heteroaryl;
  e. $C_3$-$C_{12}$ cycloalkyl;
  f. C(O)—$C_1$-$C_{12}$ alkyl;
  g. C(O)—($C_3$-$C_{12}$ cycloalkyl);

h. C(O)—$R_2$, wherein $R_2$ is as previously defined; and i. —Si($R_a$)($R_b$)($R_c$), wherein $R_a$, $R_b$ and $R_c$ are each independently selected from the group consisting of $C_1$-$C_{12}$ alkyl, aryl and substituted aryl;

3) G, L, W, Z and $R_2$' are as previously defined.

A second preferred intermediate for the preparation of compounds represented by formulae I and II is a compound represented by the formula Ib

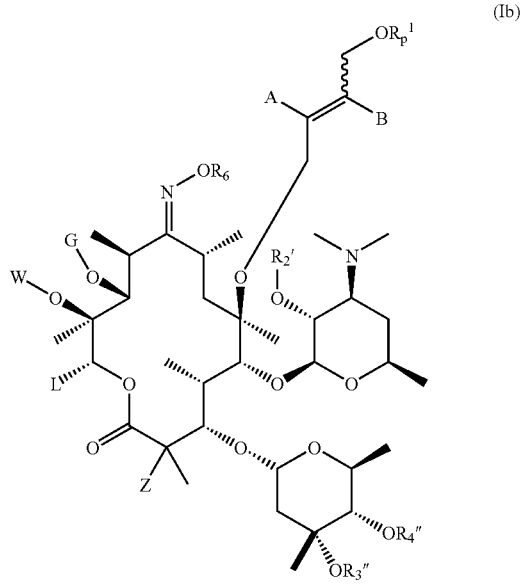

(Ib)

where A, B, G, L, W, Z, $R_2$', $R_3$", $R_4$" and $R_6$ are as previously defined and $R_p^1$ is H or $R_p$ is as previously defined.

A third preferred intermediate for the preparation of compounds represented by formula I is a compound represented by the formula Ic

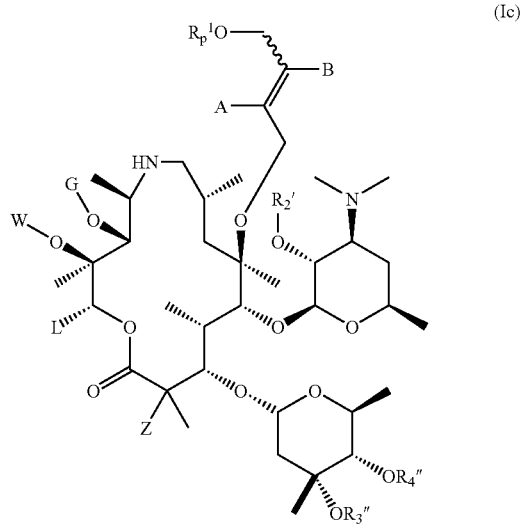

(Ic)

where A, B, G, L, W, Z, $R_2$', $R_3$" and $R_4$" are as previously defined.

A fourth preferred intermediate for the preparation of compounds represented by formula I is a compound represented by the formula Id

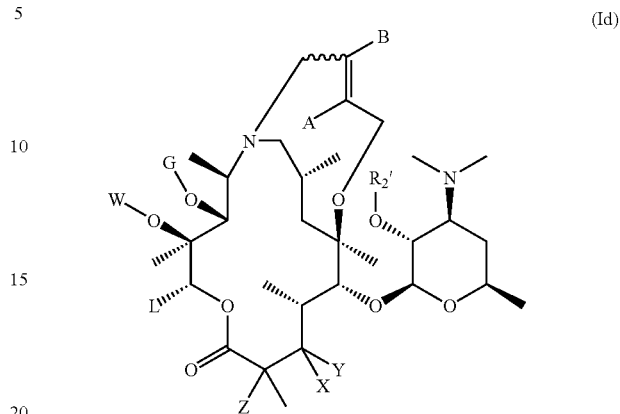

(Id)

where A, B, G, L, W, X, Y, Z, $R_2$', $R_3$" and $R_4$" are as previously defined.

A fifth preferred intermediate for the preparation of compounds represented by formula I is a compound represented by the formula Ie

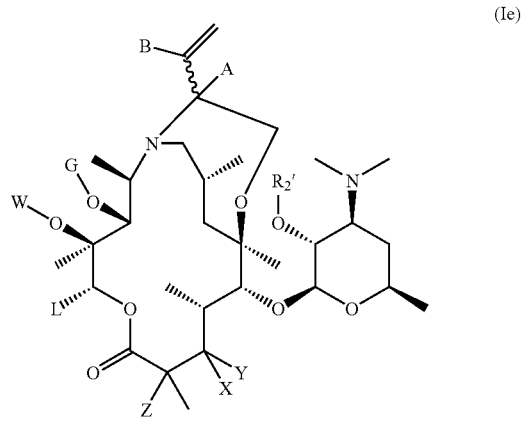

(Ie)

where A, B, G, L, W, X, Y, Z, $R_2$', $R_3$" and $R_4$" are as previously defined.

A sixth preferred intermediate for the preparation of compounds represented by formula I is a compound represented by the formula If

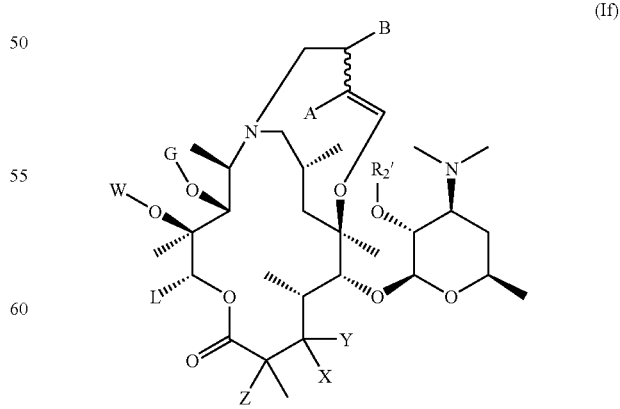

(If)

where A, B, G, L, W, X, Y, Z, $R_2$', $R_3$" and $R_4$" are as previously defined.

A seventh preferred intermediate for the preparation of compounds represented by formula I is a compound represented by the formula Ig

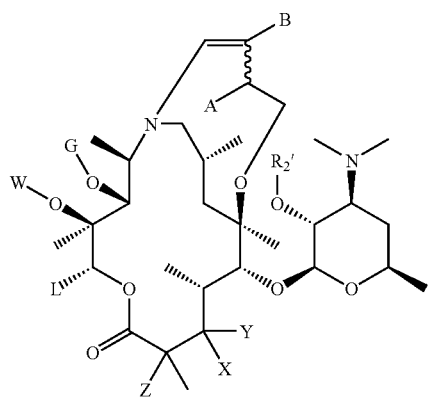

(Ig)

where A, B, G, L, W, X, Y, Z, $R_2'$, $R_3''$ and $R_4''$ are as previously defined.

An eighth preferred intermediate for the preparation of compounds represented by formula I is a compound represented by the formula Ih

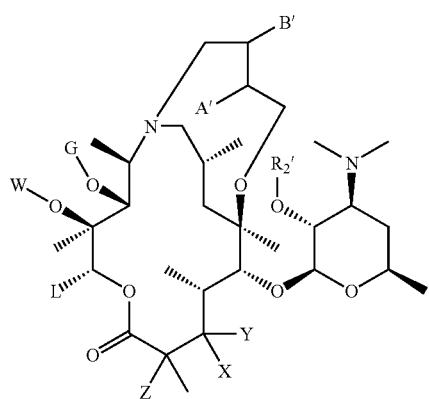

(Ih)

where A', B', G, L, W, X, Y, Z, $R_2'$, $R_3''$ and $R_4''$ are as previously defined.

A ninth preferred intermediate for the preparation of compounds represented by formula I is a compound represented by the formula Ii

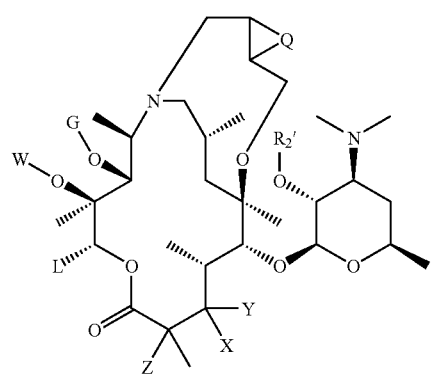

(Ii)

where G, L, Q, W, X, Y, Z, $R_2'$, $R_3''$ and $R_4''$ are previously defined.

A tenth preferred intermediate for the preparation of compounds represented by formula I is a compound represented by the formula Ij

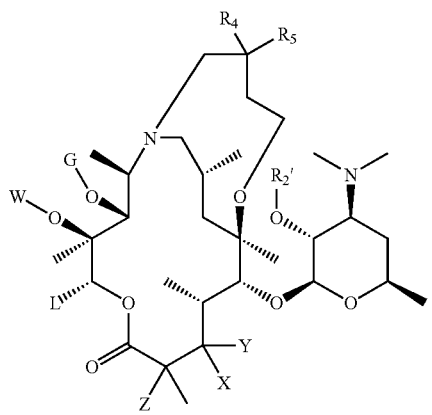

(Ij)

where G, L, W, X, Y, Z, $R_2'$, $R_4$, $R_5$, $R_3''$ and $R_4''$ are as previously defined.

An eleventh preferred intermediate for the preparation of compounds represented by formula I is a compound represented by the formula (Ik)

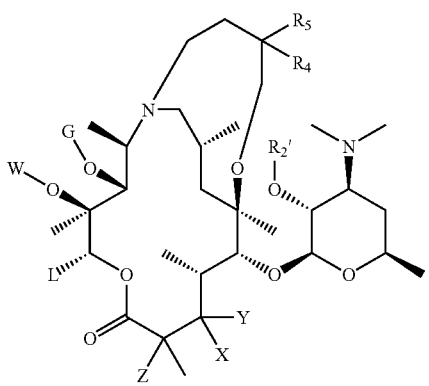

(Ik)

where G, L, W, X, Y, Z, $R_2'$, $R_4$, $R_5$, $R_3''$ and $R_4''$ are as previously defined.

A twelfth preferred intermediate for the preparation of compounds represented by formulae I and II is a compound represented by the formula Im

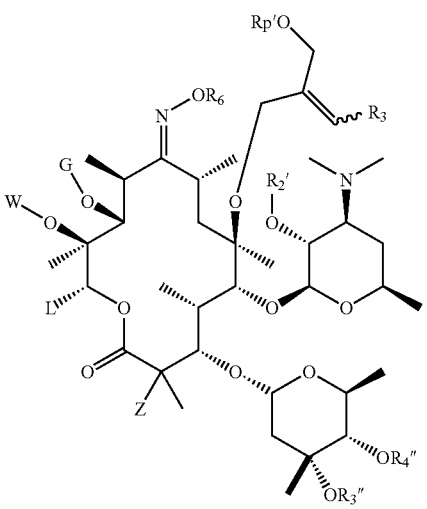

(Im)

where G, L, W, Z, $R_3$, $R_6$, $R_2'$, $R_3''$ and $R_4''$ are as previously defined.

A thirteenth preferred intermediate for the preparation of compounds represented by formula I is a compound represented by the formula In

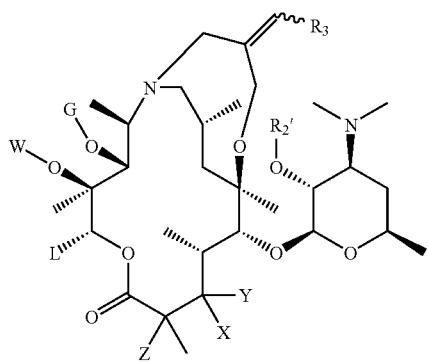

(In)

where G L, W, X, Y, Z, R₃, R₂', R₃" and R₄" are as previously defined.

A fourteenth preferred intermediate for the preparation of compounds represented by formula II is a compound represented by the formula Io:

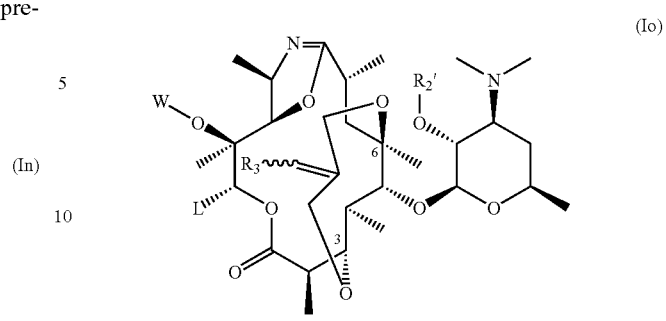

(Io)

where L, W, R₃ and R₂' are as previously defined.

A fifteenth preferred intermediate for the preparation of compounds represented by formula II is a compound represented by the formula Ip:

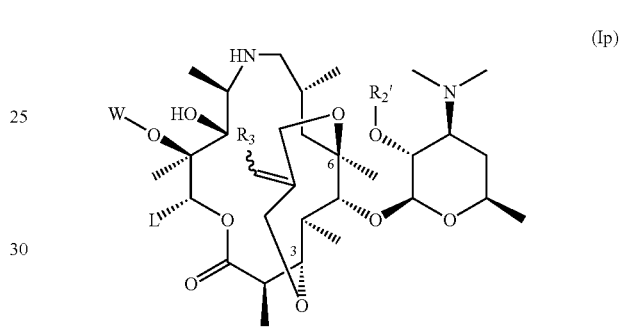

(Ip)

where L, W, R₃ and R₂' are as previously defined.

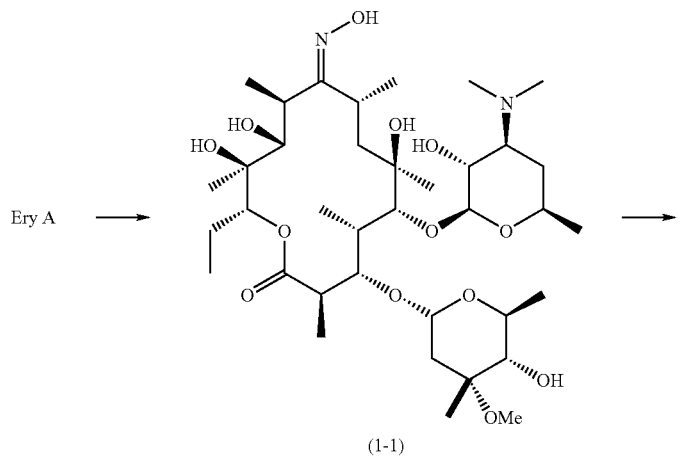

Scheme 1

Ery A ⟶ (1-1) ⟶

-continued

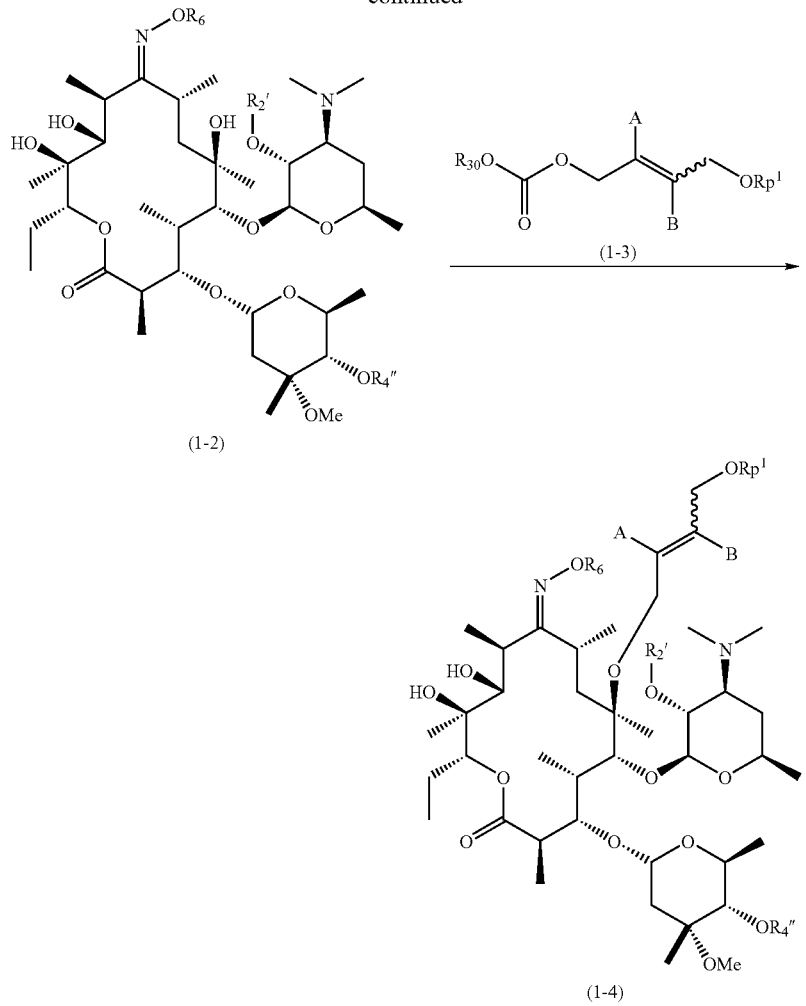

A process of the invention, as illustrated in Scheme 1, involves preparing a compound of formula (1-4) by reacting a compound of formula (1-2) with a suitable alkylating agent.

In accordance with Scheme 1, the 9-keto group of erythromycins can be initially converted into an oxime by methods described in U.S. Pat. No. 4,990,602, followed by the protection of the 2'- and 4"-hydroxyl and, if desired, the oxime groups of the erythromycin derivatives to obtain the compounds of formula (1-2).

The preparation of protected erythromycins is also described in U.S. Pat. Nos. 4,990,602; 4,331,803; 4,680,386; 4,670,549, European Patent Application No. EP 260,938.

The 2'- and 4"-hydroxyl groups are protected by reaction with suitable hydroxyl protecting reagents in an aprotic solvent. Typical hydroxyl protecting reagents include, but are not limited to, acetylating agents, silylating agents, acid anhydrides, and the like.

Examples of hydroxyl protecting reagents are, for example, acetyl chloride, acetic anhydride, benzoyl chloride, benzoic anhydride, benzyl chloroformate, hexamethyldisilazane, and trialkylsilyl chlorides.

Examples of aprotic solvents are dichloromethane, chloroform, tetrahydrofuran, N-methylpyrrolidinone, dimethylsulfoxide, N,N-dimethylformamide, N,N-dimethylacetamide, hexamethylphosphoric triamide, a mixture thereof or a mixture of one of these solvents with ether, tetrahydrofuran, 1,2-dimethoxyethane, 1,2-dichloroethane, acetonitrile, ethyl acetate, acetone and the like. Aprotic solvents do not adversely affect the reaction. Preferably, the solvent is selected from dichloromethane, chloroform, N,N-dimethylformamide, tetrahydrofuran, N-methylpyrrolidinone or mixtures thereof. A more thorough discussion of solvents and conditions for protecting the hydroxyl group can be found in T. W. Greene and P. G. M. Wuts, *Protective Groups in Organic Synthesis*, 3$^{rd}$ ed., John Wiley & Son, Inc, 1999.

Protection of 2'- and 4"-hydroxyl groups may be accomplished sequentially or simultaneously to provide compound (1-2) where $R_2'$ and/or $R_4''$ can be, for example, acetyl, benzoyl, trimethylsilyl, and the like. Preferred protecting groups include acetyl, benzoyl, and trimethylsilyl. A particularly preferred group for protecting the hydroxyl and oxime groups is the acetyl protecting group, wherein $R_2'=R_4''=R_6=Ac$.

Acetylation of the hydroxyl group is typically accomplished by treating the compound (1-1) with an acetylating reagent, for example, acetic anhydride or acetyl chloride.

The erythromycin derivative of formula (1-2) is then reacted with an alkylating agent of the formula:

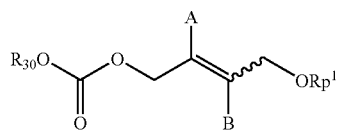

(1-3)

wherein $R_{30}$ is $C_1$-$C_{12}$-alkyl and A, B, $R_p^1$ are as previously defined.

Most palladium(0) catalysts are expected to work in this process. Some palladium(II) catalysts, such as palladium(II) acetate, which is converted into a palladium (0) species in-situ by the actions of a phosphine, will work as well. See, for example, Beller et al. *Angew. Chem. Int. Ed. Engl.*, 1995, 34 (17), 1848. The palladium catalyst can be selected from, but not limited to, palladium(II) acetate, tetrakis(triphenylphosphine)palladium(0), tris(dibenzylideneacetone)dipalladium, tetra(dibenzylideneacetone)dipalladium and the like. Palladium on carbon and palladium(II) halide catalysts are less preferred than other palladium catalysts for this process.

Suitable phosphines include, but are not limited to, triphenylphosphine, bis(diphenylphosphino)methane, 1,2-bis(diphenylphosphino)ethane, 1,3-bis(diphenylphosphino)propane, 1,4-bis(diphenylphosphino)butane, 1,5-bis(diphenylphosphino)pentane, and tri-o-tolyl-phosphine, and the like. The reaction is carried out in an aprotic solvent, preferably at elevated temperature, preferably at or above 50° C. Suitable aprotic solvents include, but are not limited to, tetrahydrofuran, N,N-dimethylformamide, dimethyl sulfoxide, N-methyl-2-pyrrolidone, hexamethylphosphoric triamide, 1,2-dimethoxyethane, methyl-tert-butyl ether, heptane, acetonitrile, isopropyl acetate and ethyl acetate. The most preferred solvents are tetrahydrofuran or toluene.

Generally, the alkylating agents have the formula (1-3) as previously described. The preferred alkylating agents are those wherein $R_{30}$ is tert-butyl, isopropyl or isobutyl. The alkylating reagents are prepared by mono-protection of a diol with a hydroxyl-protection group such as trialkylsilyl chloride, acetic anhydride, di-tert-butyl dicarbonate or the like, in the presence of a base in an aprotic solvent such as DMF, THF, or the like, followed by incorporating the other hydroxyl group into a carbonate by a wide variety of compounds which include, but are not limited to, tert-butyl chloroformate, di-tert-butyl dicarbonate, and 1-(tert-butoxycarbonyl)imidazole and the reaction is carried out in the presence of an organic or an inorganic base. The temperature of the reaction varies from about −30° C. to approximately 30° C. Preferably the alkylating reagent is di-tert-butyl dicarbonate.

An alternative method of converting the alcohol into the carbonate involves treating the alcohol with phosgene or triphosgene to prepare the chloroformate derivative of the diol. The chloroformate derivative is then converted into the carbonate by the methods described in Cotarca, L., Delogu, P., Nardelli, A., Sunijic, V, *Synthesis*, 1996, 553. The reaction can be carried out in a variety of organic solvents such as dichloromethane, toluene, diethyl ether, ethyl acetate and chloroform in the presence of a base. Examples of suitable bases include, but are not limited to, sodium hydroxide, potassium hydroxide, ammonium hydroxide, sodium carbonate, potassium carbonate, ammonium carbonate, DMAP, pyridine, triethylamine and the like. The temperature can vary from 0° C. to approximately 60° C. The reaction runs to completion in 3 to 5 hours.

Scheme 2

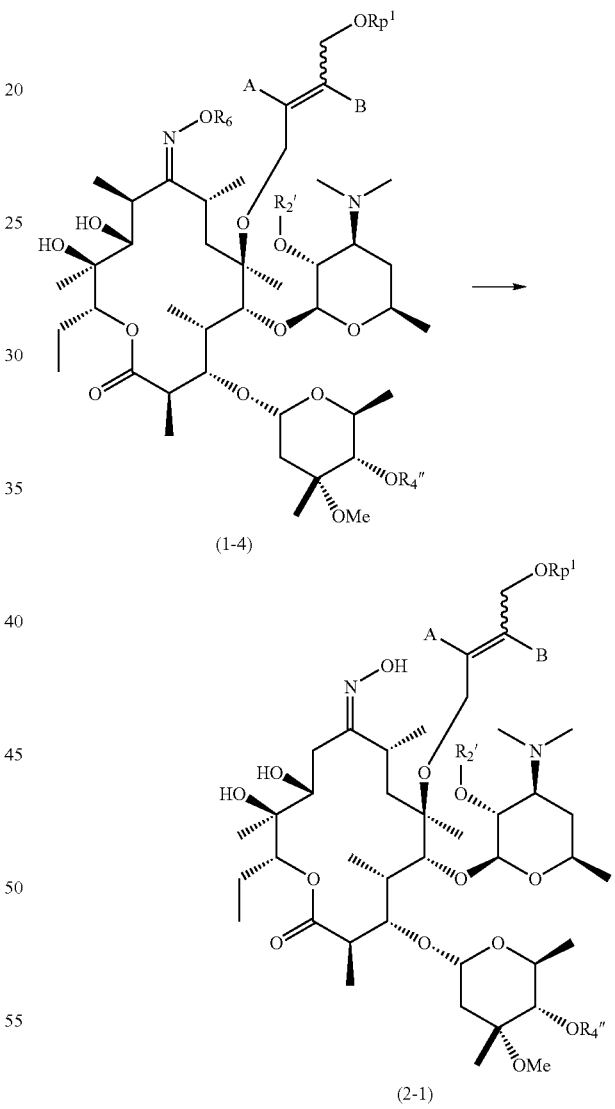

Manipulation of protection groups in compounds (1-4, wherein $R_2'$=$R_4''$=$R_6$=Ac and $R_p^1$=TBS, scheme 2) to get compounds (2-1) can be done in three steps: a) selective removal of $R_p^1$ by a fluoride such as pyridine-HF, triethylamine-HP, tetrabutylamonium fluoride, or the like, in THF, acetonitrile, methylene chloride, or the like, optionally in the presence of a base such as pyridine, triethylamine, or the like; b) acylation with an acylating reagent such as acetic anhydride, benzoic chloride, methyl chloroformate, or the like, in the presence of a base such as pyridine, triethylamine, DMAP, or the like; and c) selective deprotection of the oxime acetate via alkaline hydrolysis in protic solvents. Representative alkali compounds include ammonium hydroxide, lithium hydroxide, sodium hydroxide, potassium hydroxide, and the like. Suitable solvents include, but are not limited to, tetrahydrofuran, 1,4-dioxane, 1,2-dimethoxyethane, isopropanol, ethanol, butanol, water and mixtures thereof. The reaction temperature is preferably from about 0° C. to about 35° C., and reaction time is preferably from about 0.5 hours to about 8 hours. Alternatively, acid hydrolysis using an acid such as, but not limited to, hydrochloric acid, trifluoroacetic acid and the like, can be used to deprotect the oxime (1-4).

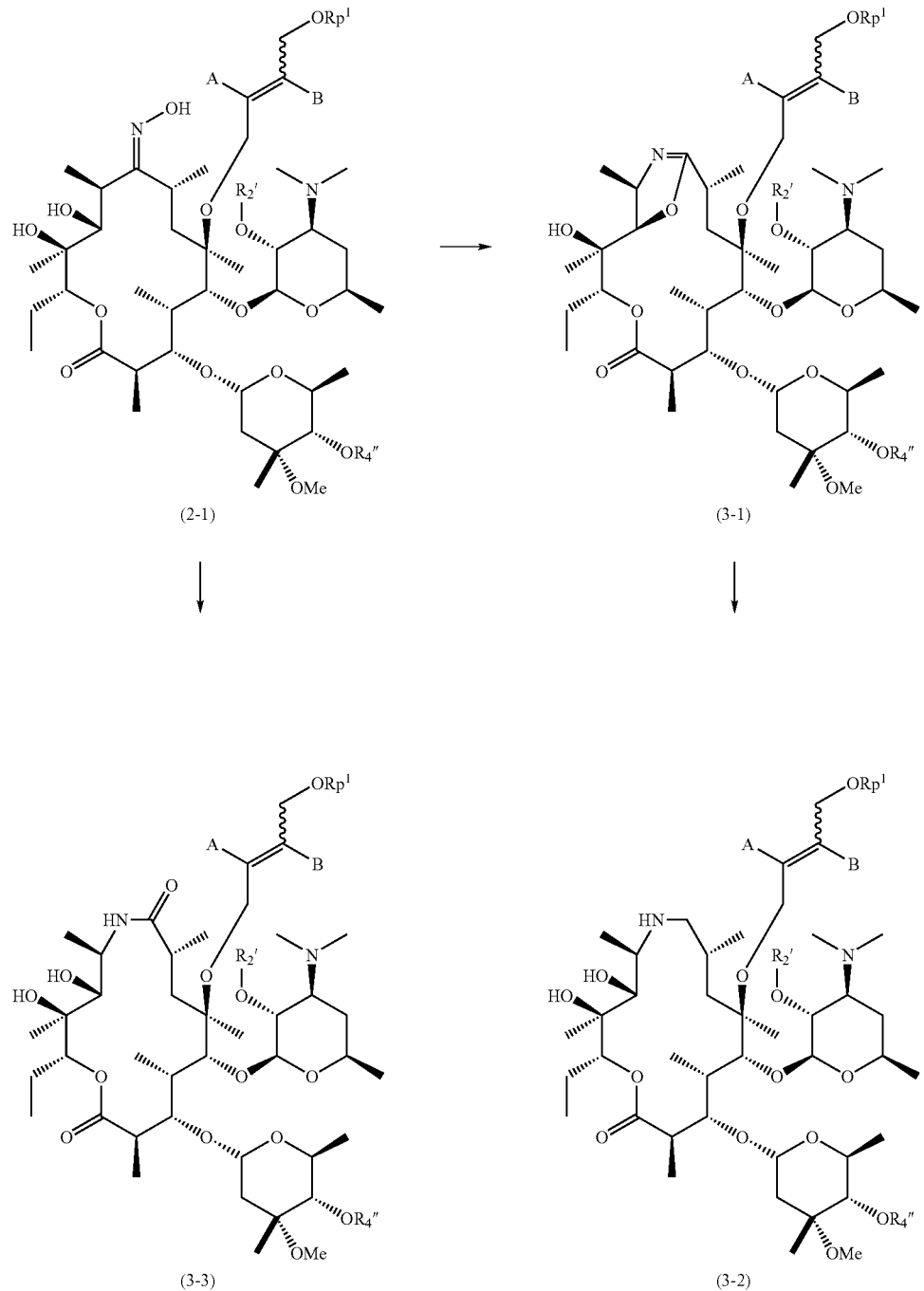

The compound of formula (2-1) can be converted into the compound of formula (3-1) and (3-3) by Beckmann rearrangement. Thus, the compound of formula (2-1) is treated with oxime activating agents and subsequently cylized intramolecularly with the C-11 hydroxyl moiety to provide the compounds of formula (3-1). Representative oxime activating agents include, but are not limited to, sulfonic anhydrides and sulfonyl halides such as p-toluenesulfonic anhydride, methanesulfonic anhydride, p-toluenesulfonyl chloride, methanesulfonyl chloride, p-bromosulfonyl chloride, optionally in the presence of a base such as, but not limited to, pyridine, triethylamine, diisopropylethyl amine, $NaHCO_3$, $Na_2CO_3$, $KHCO_3$ and $K_2CO_3$. For further details concerning the Beckmann rearrangement see L. G. Donaruma, W. Z. Heldt, *Org. React.* 11, 1-156 (1960); R. E. Gawley, ibid. 35, 1-420 (1988); C. G. McCarty in *The Chemistry of the Carbon-Nitrogen Double Bond*, S. Patai, Ed. (Interscience, New York, 1970) pp 408-439; J. R. Hauske, *Comp. Org. Syn.* 1, 98-100 (1991); K. Maruoka, H. Yamamoto, ibid. 6, 763-775; D. Craig, ibid. 7, 689-702.

Reduction of compounds of formula (3-1) to compounds of formula (3-2) can be achieved by treatment of the former with reducing agents including, but not limited to, borane in THF, borane dimethylsulfide, sodium cyanoborohydride, sodium borohydride, DIBAL, or the like, optionally in the presence of an acid such as $TiCl_4$, $CoCl_2$, $AlCl_3$, methanesulfonic acid, acetic acid, or the like. Solvents which are applicable include, but are not limited to, tetrahydrofuran, 1,4-dioxane, 1,2-dimethoxyethane, isopropanol, ethanol, butanol, acetonitrile, diethyl ether, dichloromethane, ethylene glycol, water and mixtures thereof. The reaction temperature is −78° C. to 30° C. In a particularly preferred embodiment, compounds of formula (2-1) are treated with p-toluenesulfonic anhydride and triethylamine in methylene chloride to provide compounds of formula (3-1). Compounds of formula (3-1) are then treated with $NaBH_3CN$ and acetic acid in acetonitrile to provide the compounds of formula (3-2). The compounds of formula (3-3) were synthesized via treatment of compounds of formula (2-1) with p-toluenesulfonyl chloride and $NaHCO_3$ in acetone and water.

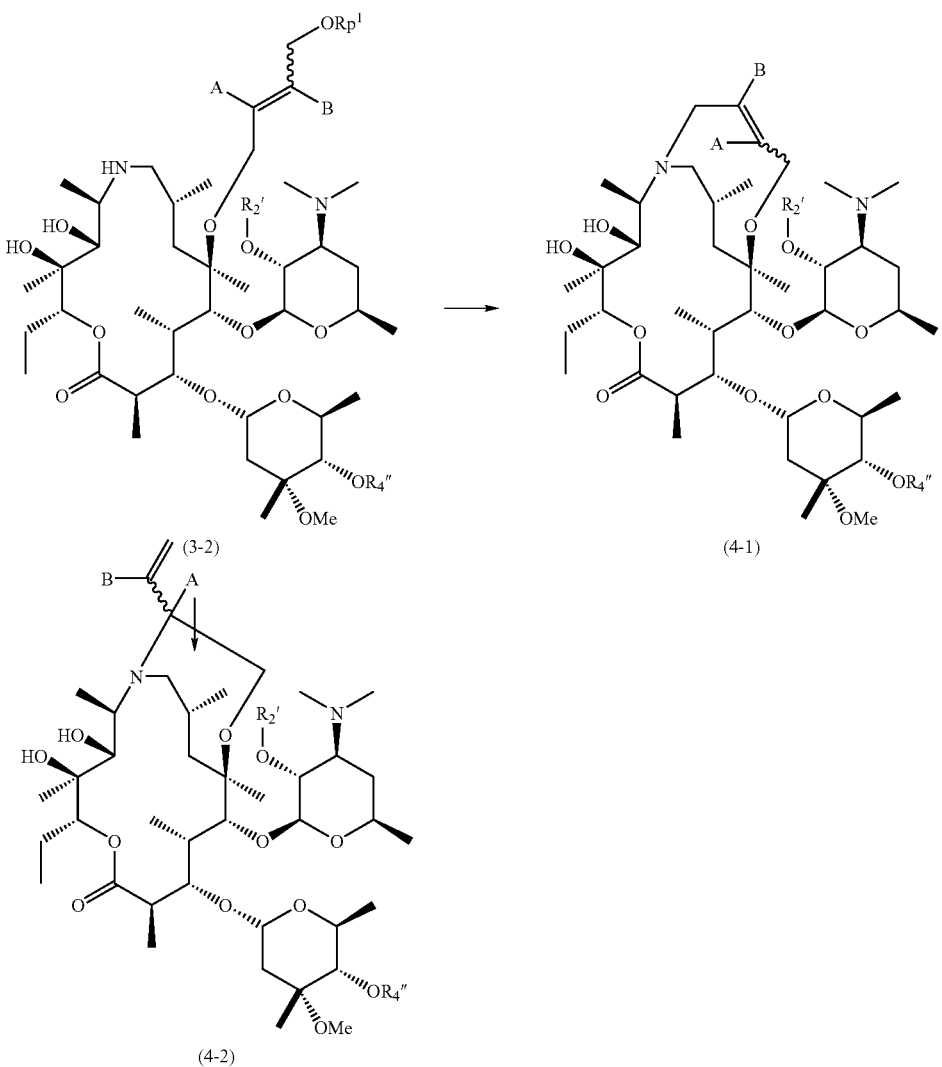

Scheme 4

Azithromycin derivative of formula (3-2), where $R_2'$, $R_p^1$, and $R_4''$ are as previously defined, can be intramolecularly cyclized to give a compounds of formula (4-1) and/or (4-2) as shown in scheme 4.

Most palladium(0) catalysts are expected to produce compounds of formula (1-3). Some palladium(II) catalysts, such as palladium(II) acetate, which are converted into a palladium (0) species in-situ by the actions of a phosphine, will work as well. See, for example, Beller et al. *Angew. Chem. Int. Ed. Engl.*, 1995, 34 (17), 1848. The palladium catalyst can be selected from, but not limited to, palladium(II) acetate, tetrakis(triphenylphospine)palladium(0), tris(dibenzylideneacetone)dipalladium, tetradibenzylideneacetone)dipalladium and the like. Palladium on carbon and palladium (II) halide catalysts are less preferred than other palladium catalysts for this process.

Suitable phosphines include, but are not limited to, triphenylphosphine, bis(diphenylphosphino)methane, 1,2-bis(diphenylphosphino)ethane, 1,3-bis(diphenylphosphino)propane, 1,4-bis(diphenylphosphino)butane, 1,5-bis(diphenylphosphino)pentane, and tri-o-tolyl-phosphine, and the like.

The reaction is carried out in an aprotic solvent, at a temperature range of 25° C.-100° C., preferably at elevated temperature, more preferably at or above 50° C. to 80° C. Suitable aprotic solvents include, but are not limited to, tetrahydrofuran, N,N-dimethylformamide, dimethyl sulfoxide, N-methyl-2-pyrrolidone, hexamethylphosphoric triamide, 1,2-dimethoxyethane, methyl-tert-butyl ether, heptane, acetonitrile, isopropyl acetate and ethyl acetate. The most preferred solvents are tetrahydrofuran or toluene. The reaction can also be carried out optionally in the presence of an organic acid including, but not limited to, acetic acid, propionic acid, and the like.

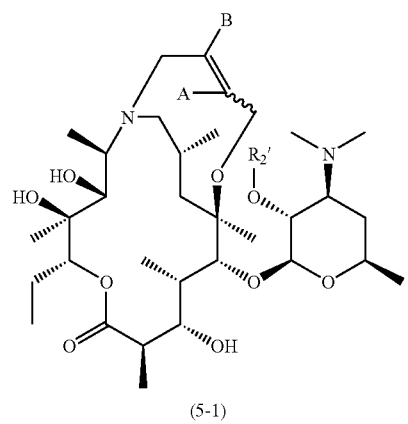

(5-1)

Another process of the invention is outlined in scheme 5 that involves the removal of the cladinose moiety of the compounds of formula (4-1), wherein A, B, $R_2'$ and $R_4''$ are as previously defined. The cladinose moiety of the macrolide compound (4-1) is removed either by mild acid hydrolysis or by enzymatic hydrolysis to afford compounds of formula (5-1). Representative acids include, but are not limited to, dilute hydrochloric acid, sulfuric acid, perchloric acid, chloroacetic acid, dichloroacetic acid or trifluoroacetic acid. Suitable solvents for the reaction include, but are not limited to, methanol, ethanol, isopropanol, butanol, water and mixtures there of. Reaction times are typically 0.5 to 24 hours. The reaction temperature is preferably 0 to 80° C.

Scheme 5

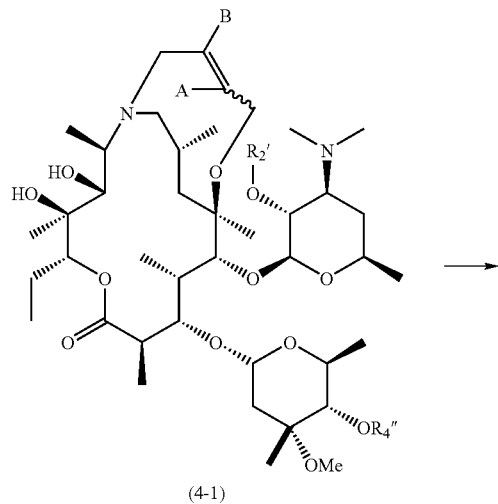

(4-1)

Scheme 6

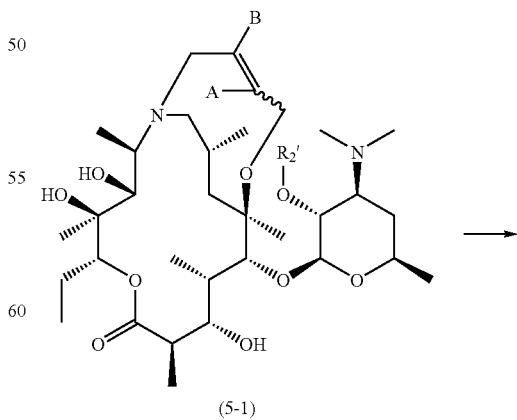

(5-1)

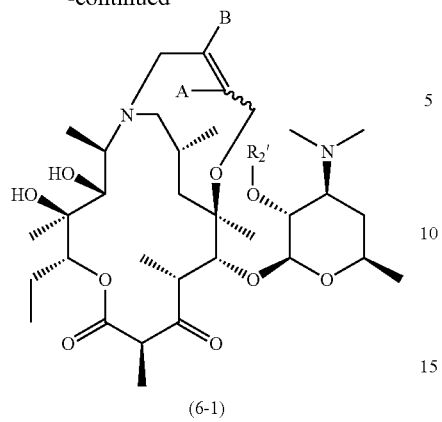

(6-1)

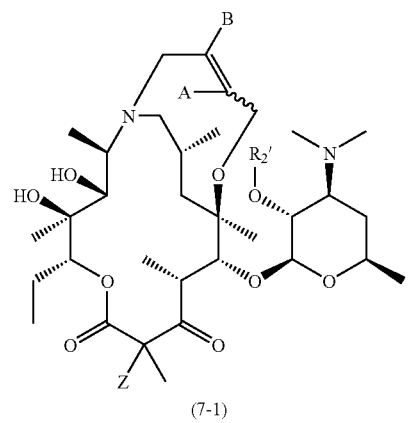

(7-1)

Conversion of compounds of formula (5-1) to compounds of formula (6-1) can be accomplished by oxidation of the 3-hydroxy group to a 3-oxo group using Dess-Martin periodinane (for further details concerning the Dess-Martin oxidation see D. B. Dess, J. C. Martin, *J. Org. Chem.* 48, 4155 (1983)), a Corey-Kim reaction with N-chlorosuccinimide-dimethylsulfide (for further details concerning the Corey-Kim oxidation reaction see E. J. Corey, C. U. Kim, *J. Am. Chem. Soc.* 94, 7586 (1972)), or a Moffat oxidation with a carbodiimide-DMSO complex in the presence of pyridinium trifluoroacetate, TPAP, PDC, and the like (for further details concerning the Moffat oxidation see J. G. Moffatt, "Sulfoxide-Carbodiimide and Related Oxidations" in *Oxidation* vol. 2, R. L. Augustine, D. J. Trecker, Eds. (Dekker, New York, 1971) pp 1-64; T. T. Tidwell, *Org. React.* 39, 297-572 *passim* (1990); and T. V. Lee, *Comp. Org. Syn.* 7, 291-303 *passim* (1991)). In a preferred embodiment, compounds of formula (5-1) are treated with Dess-Martin periodinane in dichloromethane at about 0° C. to about 25° C. for approximately 0.5 to 4 hours to produce compounds of formula (6-1).

Scheme 7

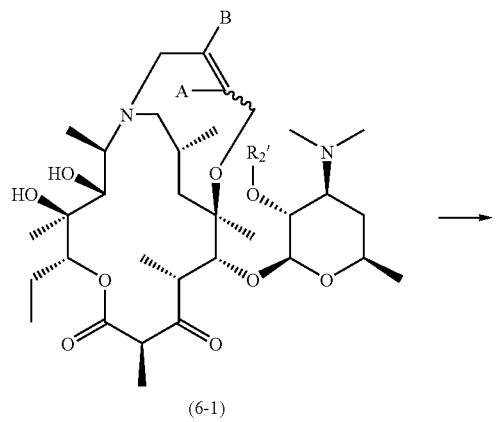

(6-1)

Scheme 7 illustrates the procedure by which compounds of formula (6-1), wherein A, B, and $R_2'$ are as previously defined, may be converted to compounds of formula (7-1), wherein A, B, Z, and $R_2'$ are as previously defined, by treatment with a halogenating reagent. This reagent acts to replace a hydrogen atom with a halogen atom at the C-2 position of the ketolide. Various halogenating reagents may be suitable for this procedure.

Fluorinating reagents include, but are not limited to, N-fluorobenzenesulfonimide in the presence of base, 10% $F_2$ in formic acid, 3, 5-dichloro-1-fluoropyridinium tetrafluoroborate, 3,5-dichloro-1-fluoropyridinium triflate, $(CF_3SO_2)_2$ NF, N-fluoro-N-methyl-p-toluenesulfonamide in the presence of base, N-fluoropyridinium triflate, N-fluoroperfluoropiperidine in the presence of base.

Chlorinating reagents include, but are not limited to, hexachloroethane in the presence of base, $CF_3CF_2CH_2ICl_2$, $SO_2Cl_2$, $SOCl_2$, $CF_3SO_2Cl$ in the presence $Cl_2$, NaOCl in the presence of acetic acid.

Brominating reagents include, but are not limited to, $Br_2$•pyridine•HBr, $Br_2$/acetic acid, N-bromosuccinimide in the presence of base, LDA/$BrCH_2CH_2Br$, or LDA/$CBr_4$.

A suitable iodinating reagent is N-Iodosuccinimide in the presence of base, or $I_2$, for example.

Suitable bases for the halogenating reactions requiring them are compounds such as alkali metal hydrides, such as NaH and KH, or amine bases, such as LDA or triethylamine, for example. Different reagents may require different type of base, but this is well known within the art.

A preferred halogenating reagent is N-fluorobenzenesulfonimide in the presence of sodium hydride.

Suitable solvents are dimethylformamide, dimethyl sulfoxide, pyrrolidinone and the like.

It will be appreciated by one skilled in the art that all ketolide compounds delineated herein may be halogenated at the C2-position if so desired.

Scheme 8
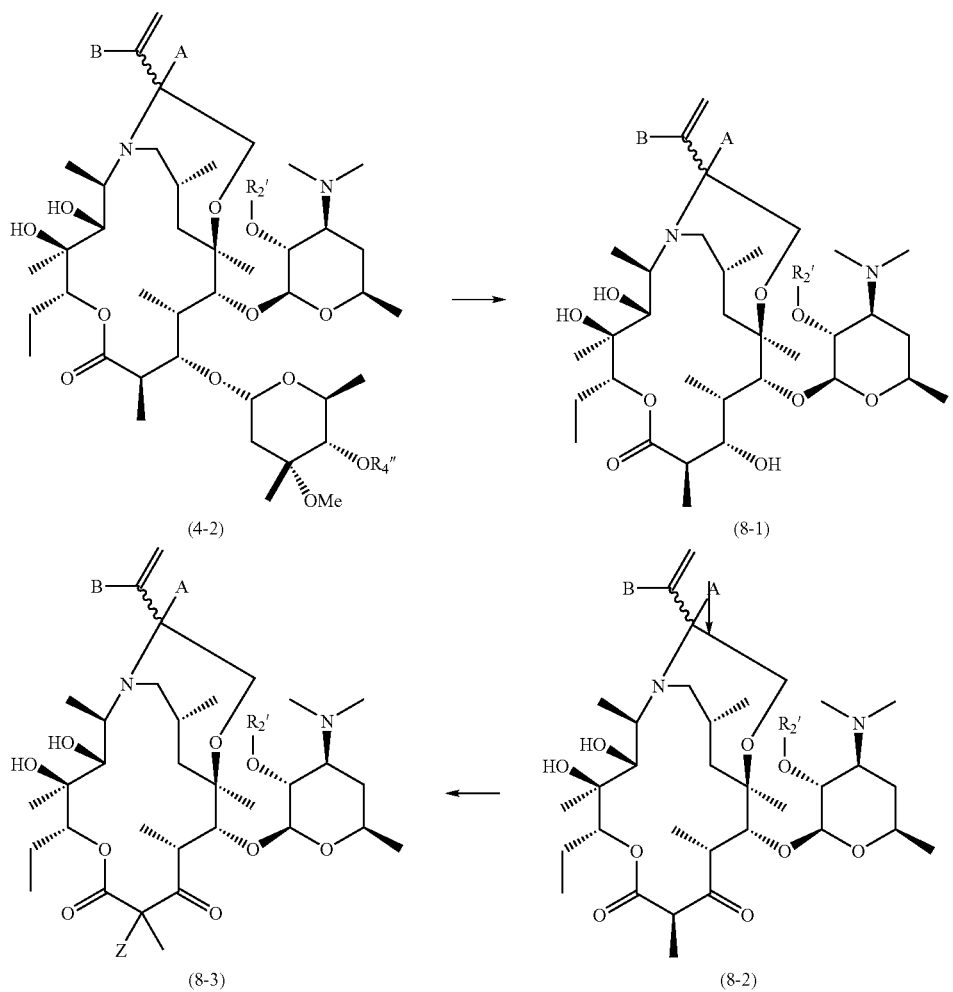
Compounds according to the formula (8-3) may be prepared by removal of the cladinose sugar from compounds of formula (4-2), as described in scheme 5. Followed by oxidizing compounds of formula (8-1), and subsequently substituting at the C-2 position of the compounds of formula (8-2) as previously described in Schemes 6 and 7 respectively.
Scheme 9
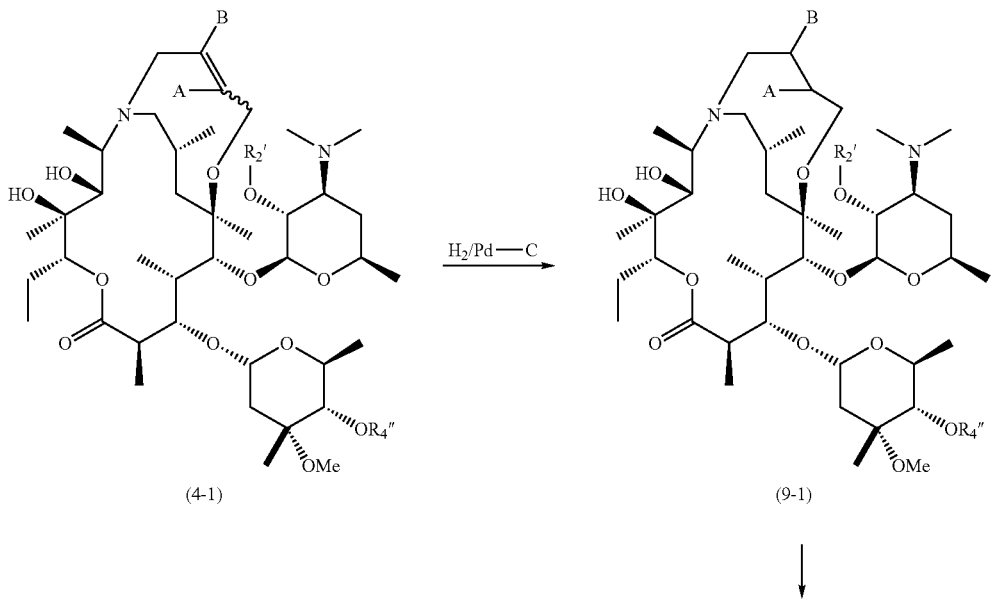

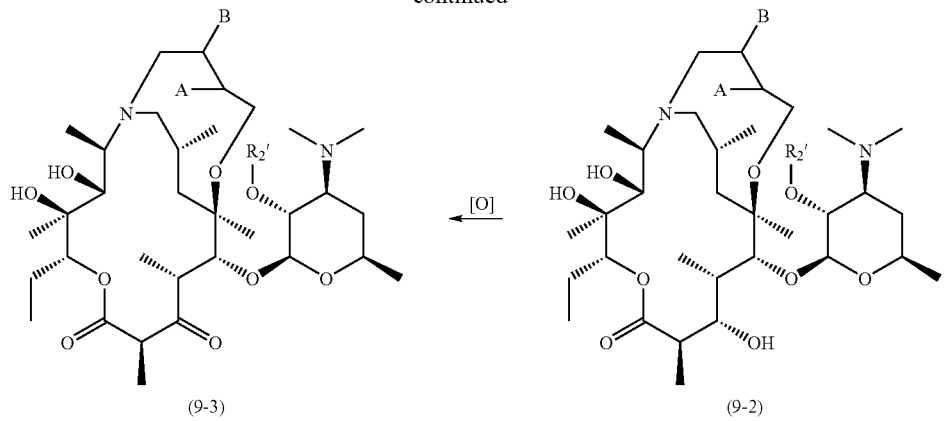

(9-3)          (9-2)

Compounds according to the formula (9-1) may be prepared from compounds of formula (4-1) by hydrogenation methods known in the art, for example, but not limited to, metal hydrides, such as, borane, or hydrogen, optionally in the presence of a catalyst, such as, palladium-on-charcoal, platinum metal or oxide, Wilkinson's catalyst and the like (see, Rylander, *Hydrogenation Methods*; Academic Press: New York, 1985; J. March, *Advanced Organic Chemistry* $4^{th}$ ed., Wiley & Son, Inc., 1992; and the references therein). Compounds according to the formula (2-3) may be prepared by removal of the cladinose sugar from compounds according to formula (2-1), as described in scheme 5, and subsequently oxidizing compounds according to formula (9-2), as previously described in scheme 6.

Scheme 10

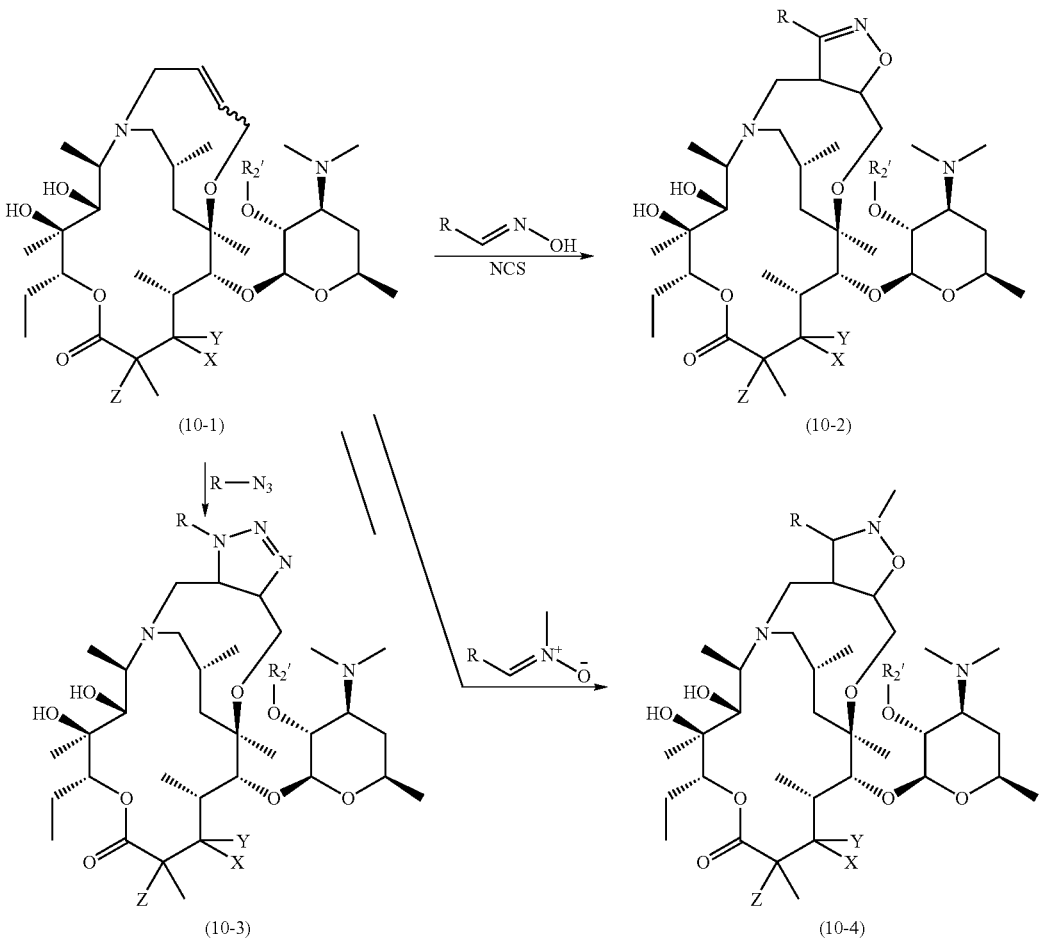

(10-1)          (10-2)

(10-3)          (10-4)

As described in scheme 10, compounds (10-2, 10-3 and 10-4, where R=R₃; wherein R₃, R₂', X, Y and Z are as previously defined) can be prepared by the well-established 1,3-dipolar cycloaddition reactions, such as, but not limited to, reaction of compound (10-1) and an oxime in the presence of NCS in an aprotic solvent such as ethyl acetate, methylene chloride, THF, or the like, to form compound (10-2) (see (a) Tufariello, Joseph J. *Nitrones* in 1,3 *[One, Three]-Dipolar Cycloaddit. Chem.* (1984), 2, 83-168. (b) Huisgen, Rolf. *1,3-Dipolar cycloaddition—introduction, survey, mechanism* in 1,3 *[One, Three]-Dipolar Cycloaddit. Chem.* (1984), 1, 1-176, and the references therein). Compounds (10-3) and (10-4) can be prepared similarly by reacting compound (10-1) with an azide or a nitrone respectively.

Other 1,3-Dipolar cycloaddition reactants useful in forming cycloaddition products with compounds of the present invention such as compound (10-1) include, but are not limited to, diazoalkane, nitrous oxide, nitrile imine, nitrile ylide, nitrile oxide, etc. (see, Padwa *1,3-Dipolar Cycloaddition Chemistry*, 2 vols.; Wiley: New York, 1984, and J. March, *Advanced Organic Chemistry*, 4$^{th}$ edition; Wiley: New York, 1992, and the references therein).

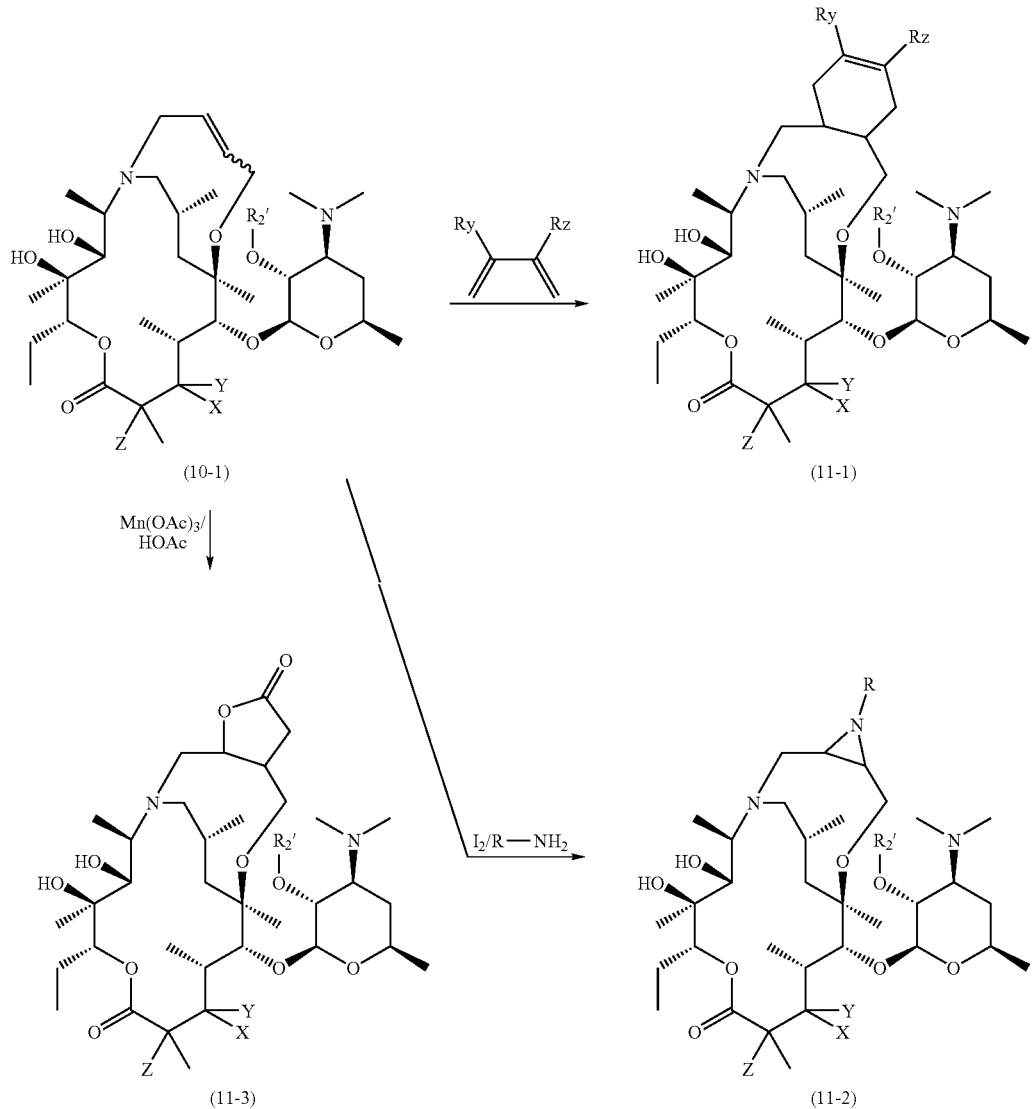

Scheme 11

Compound (11-1, wherein R₂', X, Y and Z are as previously defined) in scheme 11 is prepared by Diels-Alder reactions, where R$_y$ and R$_z$ are for example, but not limited to, CHO, COOH, COOR, COR, COAr, CN, NO₂, Ar, CH₂OH, CH₂Cl, CH₂NH₂, CH₂CN, CH₂COOH, halogen, —C≡C—, R and the like, R being R₃ as previously defined herein (see (a) Danishefsky, Samuel. *Cycloaddition and cyclocondensation reactions of highly functionalized dienes: applications to organic synthesis in Chemtracts: Org. Chem.* (1989), 2 (5), 273-97, (b) Larock *Comprehensive Organic Transformation*; VCH: New York, 1989, 263-272, and the references therein).

Aziridines such as compound (11-2) can be obtained from, for example, but not limited to, the reaction of compound (10-1) with iodine in the presence of a primary amine in an aprotic solvent such as methylene chloride, THF, and the like.

Lactones such as compound (11-3) can be obtained by a variety of reactions such as but not limited to, reaction with: manganese (III) acetate in the presence of acetic acid, lead tetraacetate, α-bromocarboxylic acids in the presence of benzoyl peroxide etc. (see, Larock *Comprehensive Organic Transformation*; VCH: New York, 1989; J. March, *Advanced Organic Chemistry*, 4<sup>th</sup> edition; Wiley: New York, 1992, and the references therein).

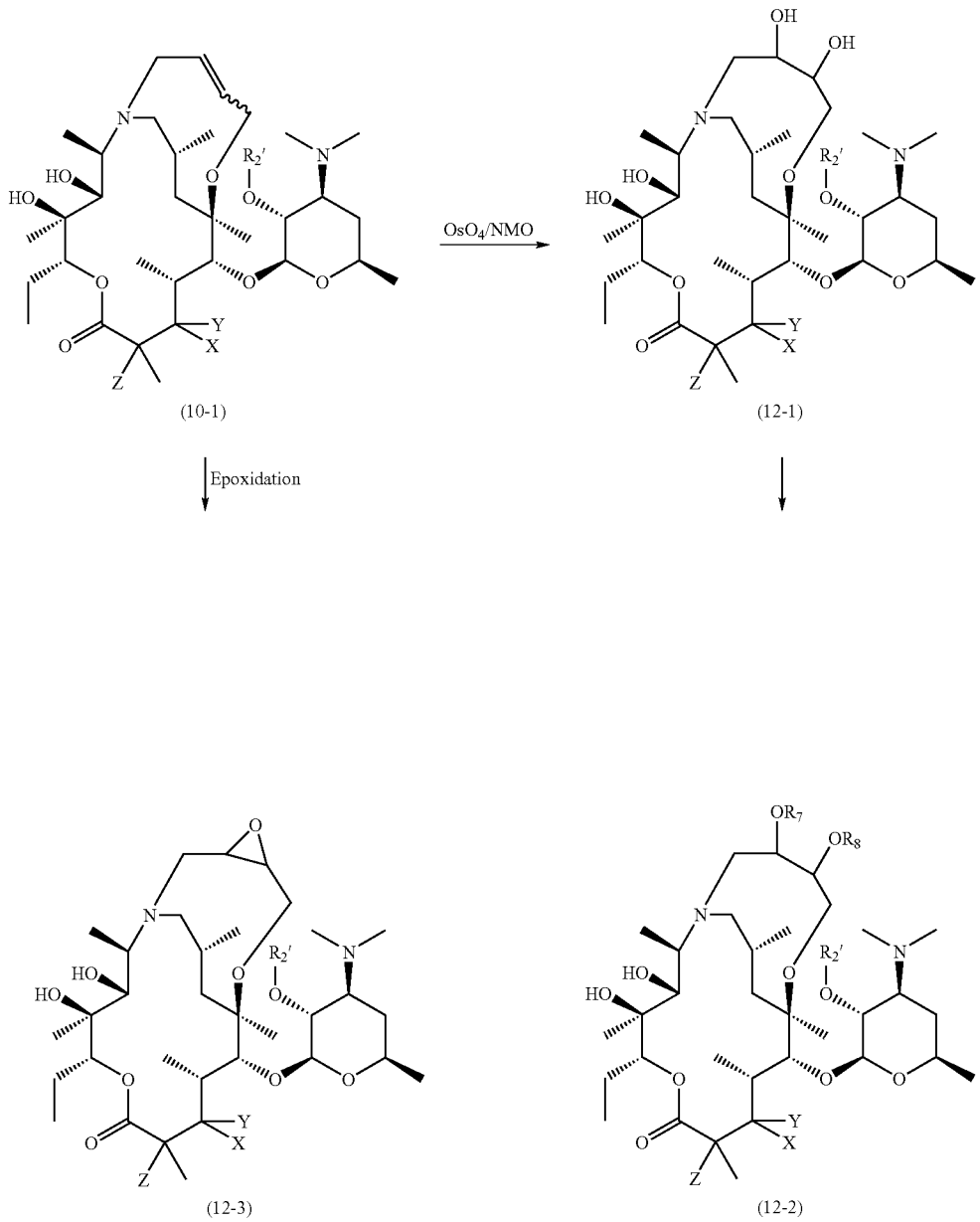

Compound (12-1, wherein $R_2'$, X, Y and Z are as previously defined) in scheme 12 is prepared by osmium tetraoxide ($OsO_4$) catalyzed dihydroxylation of the double bond. In a typical procedure, compound (10-1) is treated with about 1 to about 3 equivalents of NMO in a solvent like t-butanol or acetone, with or without water, in the presence of about 1 to about 10% of $OsO_4$. Compound (12-2) can then be obtained from compound (12-1) through standard acylation or alkylation of the diol, where $R_7$ and $R_8$ are independently selected from $R_3$ and where $R_3$ is as previously defined herein.

Compound (12-3) is prepared by epoxidation of the double bond with reagents such as, but not limited to, peracids, e.g. m-CPBA, hydrogen peroxide, t-BuOOH etc. (see (a) *Chem. Rev.* 1989, 89, 431; (b) *Chem. Rev.* 1992, 92, 873, and references therein).

ment with hydrogen peroxide and NaOH, to obtain compounds of formula (13-1).

Compounds of formula (13-1) may be oxidized to compounds of formula (13-2) with a suitable oxidizing agent as previously mentioned in scheme 5. Compounds of formula (13-2) can be reacted with appropriate substituted hydroxylamines of the general formula $RONH_2$ where R is preferably $R_3$, where $R_3$ is as previously defined, in a protic solvent under acidic or basic conditions to give compounds of the formula (13-3). Representative acids include, but are not limited to, hydrochloric acid, phosphoric acid, sulfuric acid, p-toluenesulfonic acid, etc. Representative bases include, for example, triethylamine, pyridine, diisopropylethyl amine, 2,6-lutidine, and the like. Appropriate solvents include, but Scheme 13

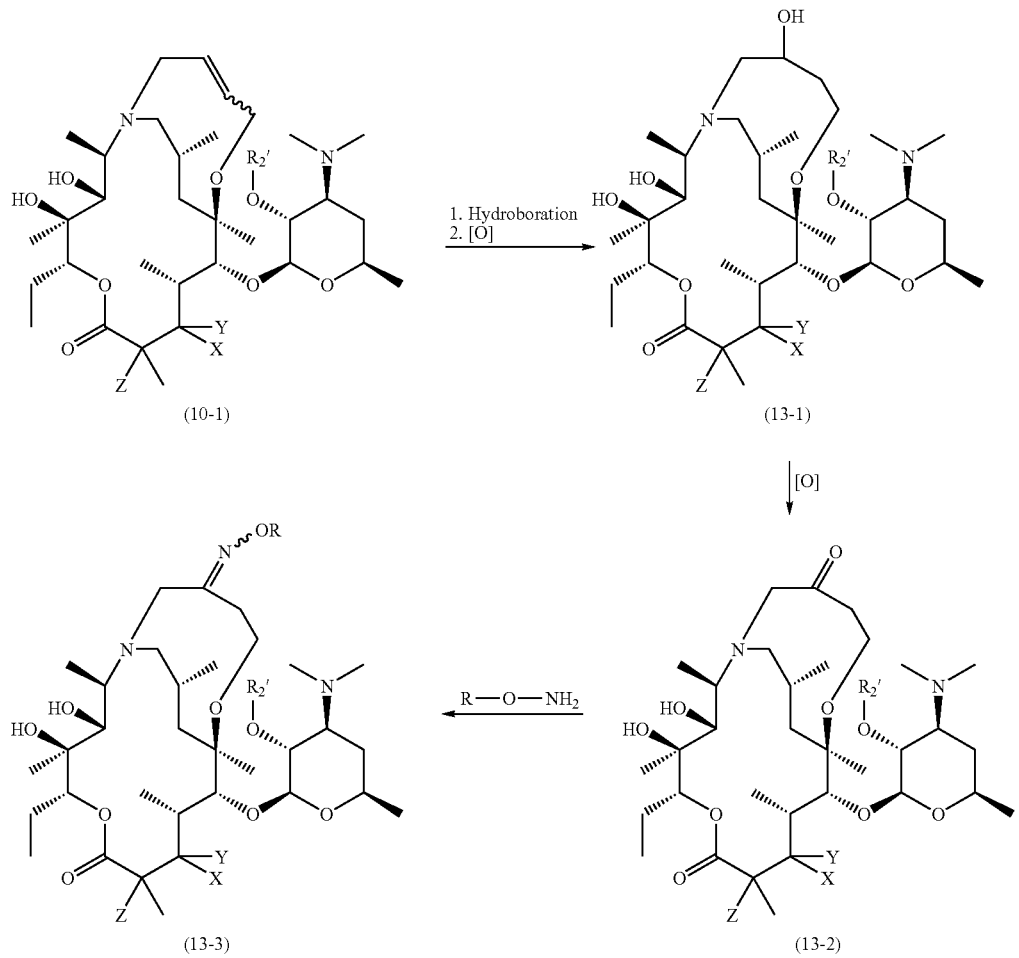

As outlined in scheme 13, compounds of formula (10-1, wherein $R_2'$, X, Y and Z are as previously defined) can be converted to compounds of formula (13-1) by, for example, but not limited to, hydroboration with a borane reagent, for example, $B_2H_6$-THF, 9-BBN (9-borabicyclo[3.3.1]nonane), and the like, (optionally complexed with THF, dimethylsulfide, phosphines, tertiary amines etc.) and followed by treatment are not limited to, methanol, ethanol, water, tetrahydrofuran, 1,2-dimethoxyethane and ethyl acetate.

Also, ketone compounds of the formula (13-2), where the ketone is on the 6,9a-4-carbon bridge, may be further derivatized, for example, but not limited to, conversion to the corresponding amines by reductive amination, reaction with hydrazines to form the corresponding hydrazones, conversion to substituted alkenes by Wittig reaction, alkylation with Grignard reagent etc., by standard methods known in the art and from references incorporated herein.

Alternately, the double bond in the 6,9a-4-carbon bridge in compounds of formula (6-1) may be further derivatized similarly by appropriate procedures known in the art and as disclosed herein, for example, but not limited to, Diels-Alder reactions, 1,3-dipolar cycloaddition reactions, hydrogenation, reaction with primary amines in the presence of iodine to form aziridines, hydroboration, etc.

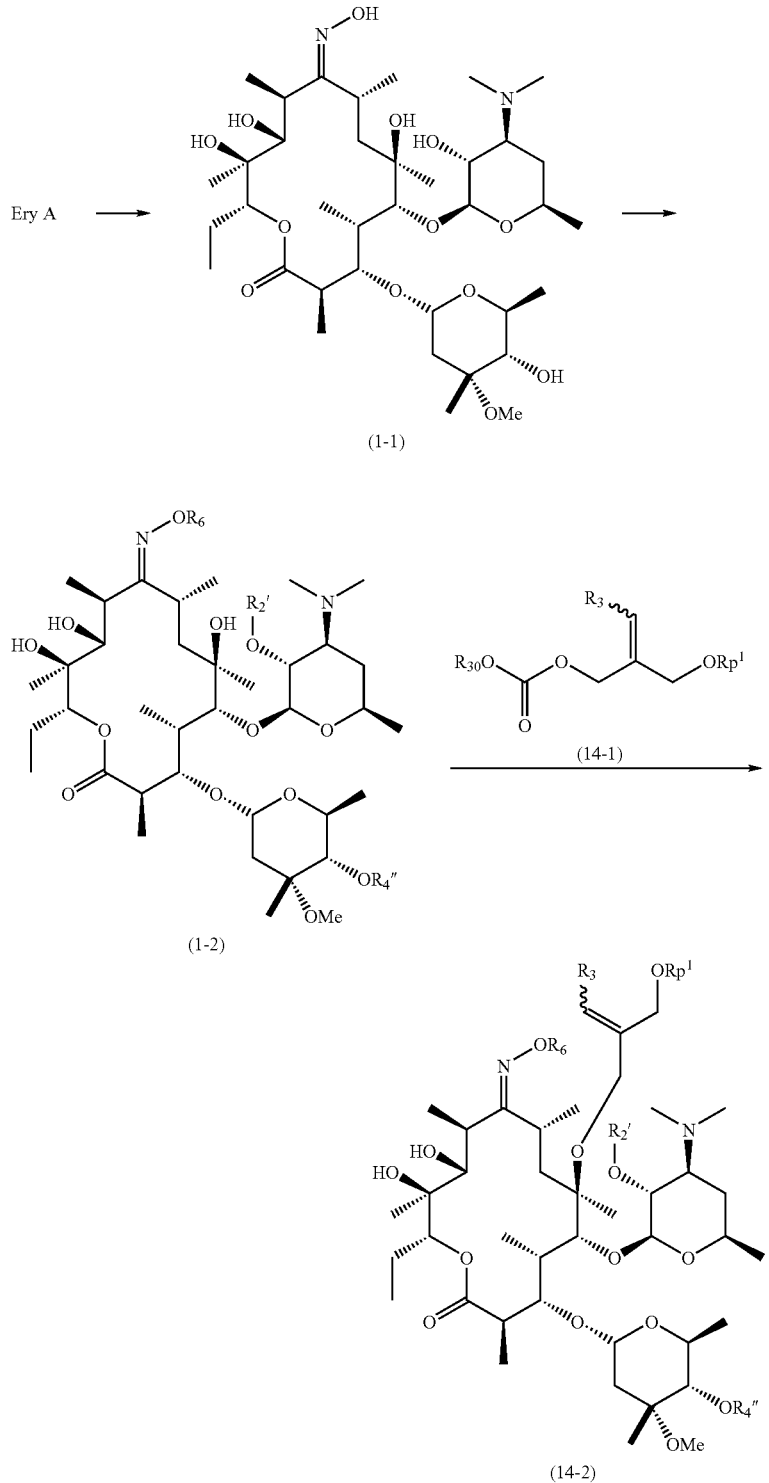

Compounds of formula (14-2) may be prepared similarly to compounds of formula (1-4) as described in Scheme 1 by using alkylating agents of formula (14-1):
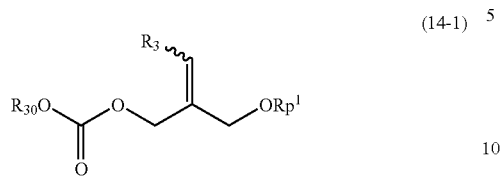
wherein $R_3$, $R_{30}$ and $R_p^1$ as previously defined.
Scheme 15
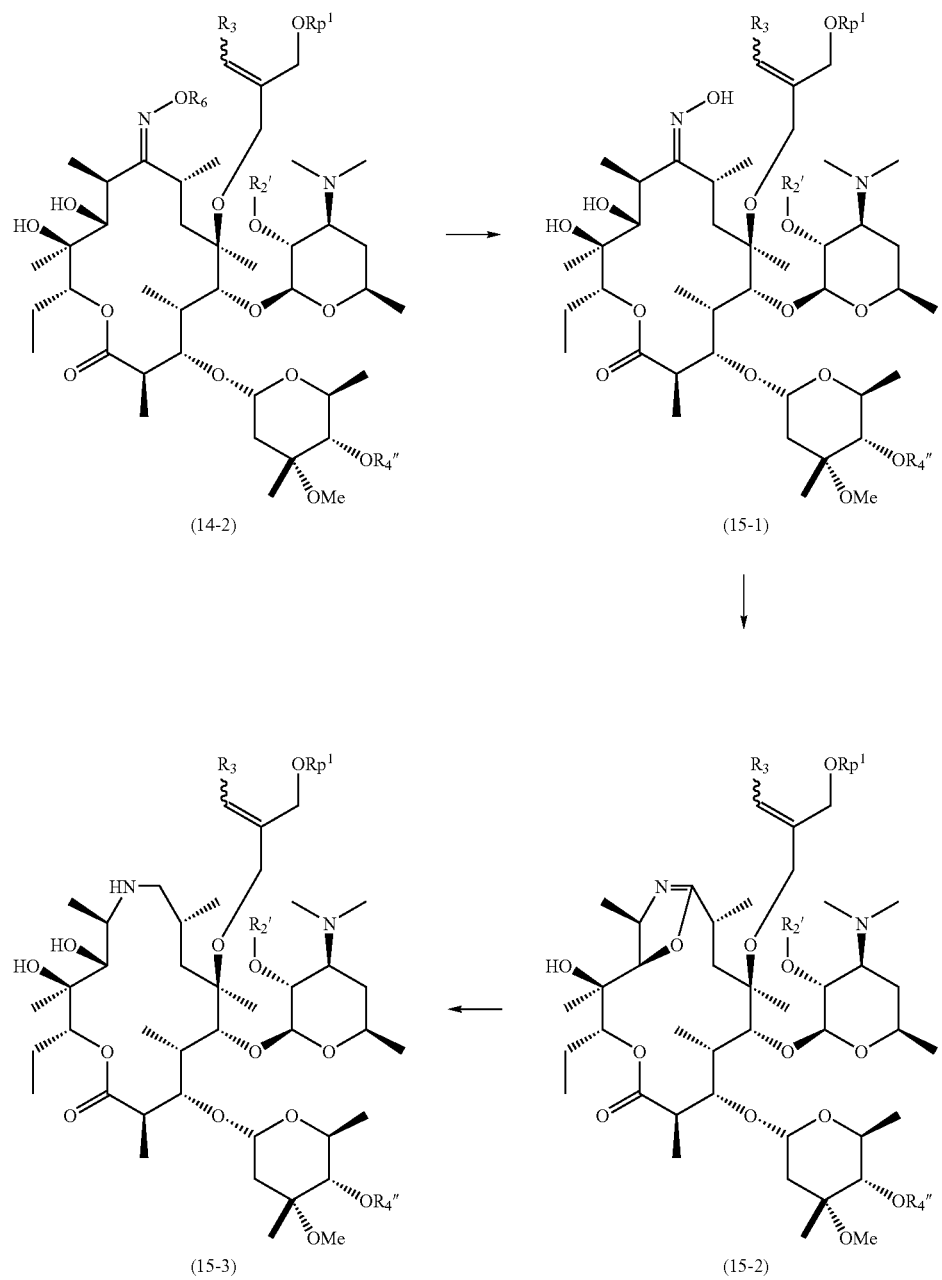

Compounds of formula (14-2) can be converted to compounds of formula (15-3) similarly as previously described in schemes 2 and 3 via manipulation of protection group of $R_p^1$, selective deprotection to give oximes (15-1), followed by Beckmann's rearrangement to form compounds of formula (15-2), and subsequently reduction of the iminoether moiety with sodium cyanoborohyride in the presence of acetic acid and acetonitrile as the preferred solvent at room temperature or by other appropriate procedures known in the art to provide compounds of formula (15-3).

Scheme 16

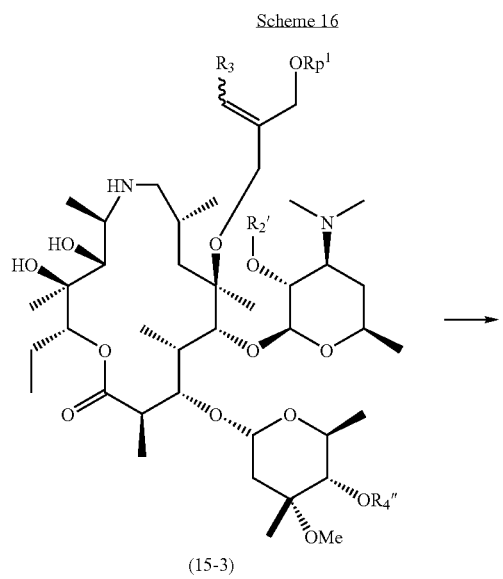

(15-3)

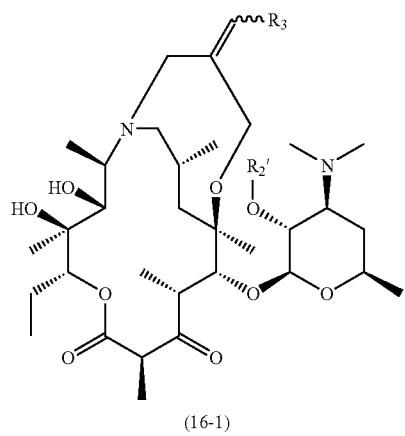

(16-1)

Compounds of formula (15-3) can be converted to the cyclized products (16-1) similarly as previously described in Scheme 4 to 6.

Scheme 17

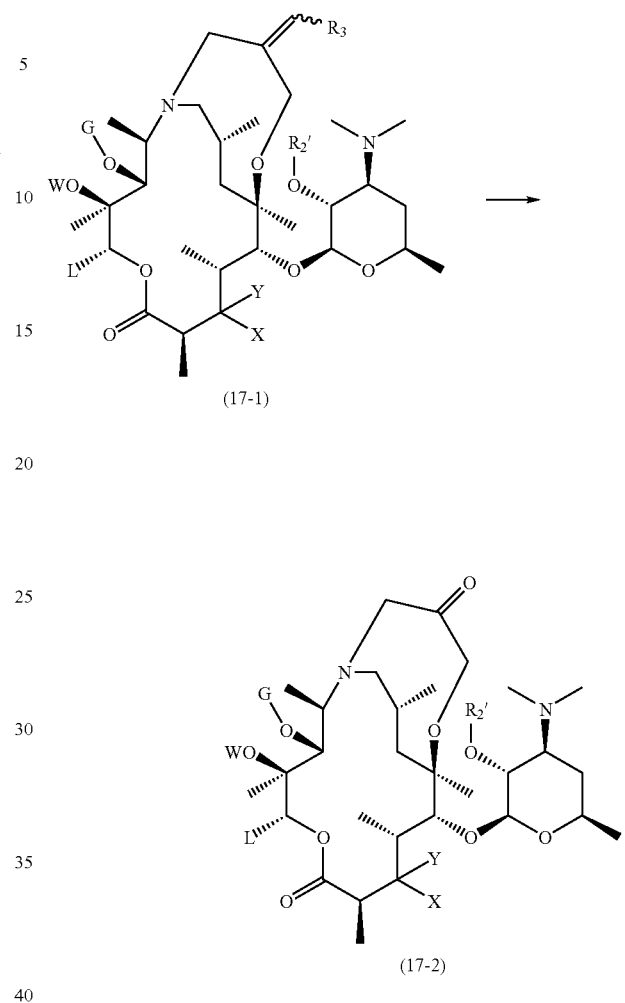

Scheme 17 illustrates another process of the invention by which to prepare compound of the present invention. Conversion of alkenes (17-1) into ketones (17-2) can be accomplished by ozonolysis followed by decomposition of the ozonide with the appropriate reducing agents. The reaction is typically carried out in an inert solvent such as, but not limited to, methanol, ethanol, ethyl acetate, glacial acetic acid, chloroform, methylene chloride or hexane or mixtures thereof, preferably methanol, preferably at −78° C. to −20° C. Representative reducing agents are, for example, triphenylphosphine, trimethylphosphite, thiourea, and dimethyl sulfide, preferably triphenylphosphine. A more thorough discussion of ozonolysis and conditions therefor may be found in J. March, *Advanced Organic Chemistry*, 4th ed., Wiley & Son, Inc, 1992. Alternatively, compounds of formula (17-2) can be prepared from compounds of formula (17-1) dihydroxydation with $OsO_4$ followed by $NaIO_4$ cleavage.

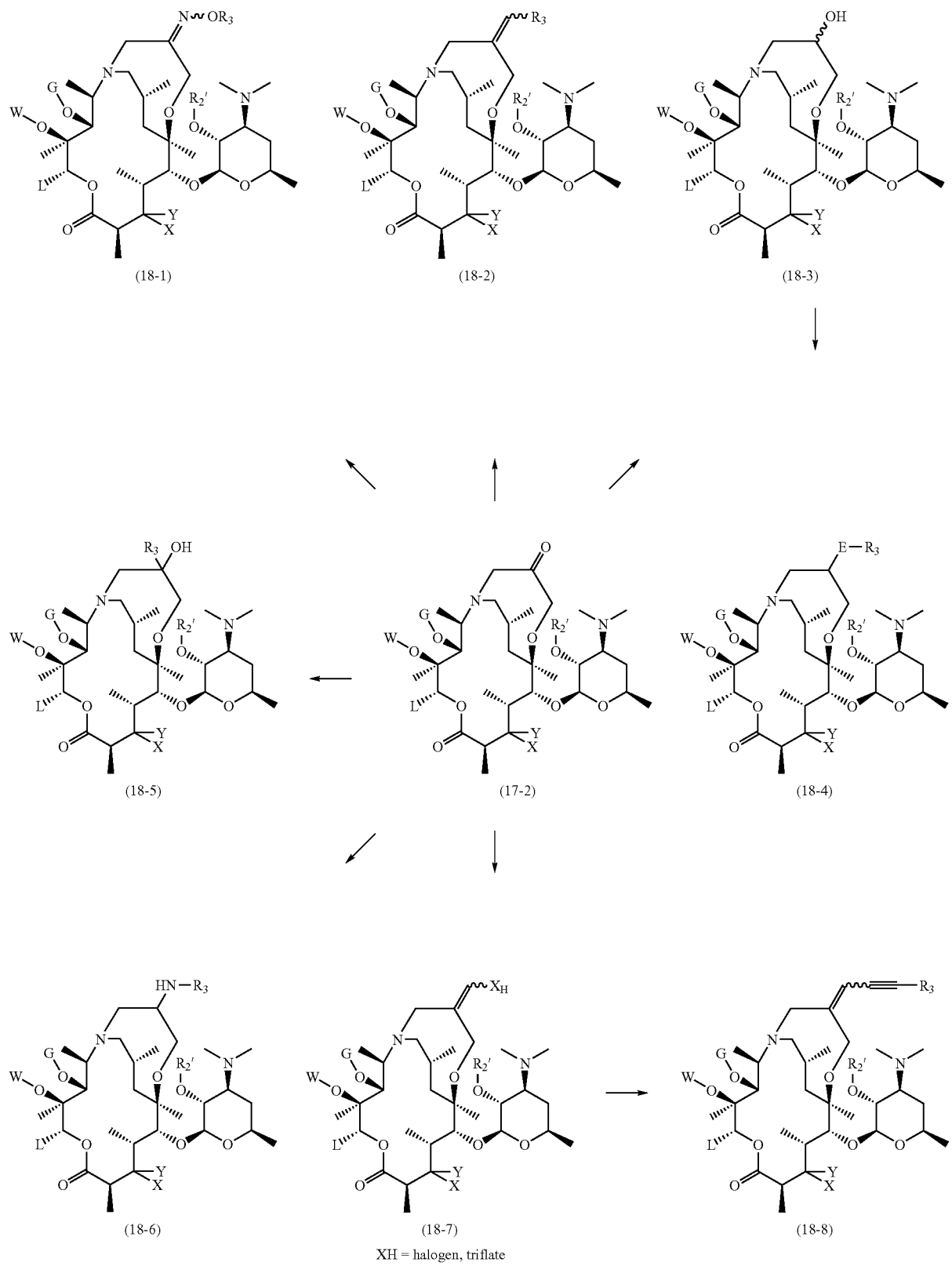
Scheme 18
XH = halogen, triflate

Compounds according to the invention of the formula (17-2) can be further functionalized in a variety of ways. Scheme 18 details a procedure for the conversion of the ketone of formula (17-2) into an oxime of formula (18-1). Oxime formation can be accomplished using the appropriate substituted hydroxylamine under either acidic or basic conditions in a variety of solvents. Representative acids include, but are not limited to, hydrochloric, phosphoric, sulfuric, p-toluenesulfonic, and pyridinium p-toluene sulfonate. Likewise, representative bases include, but are not limited to, triethylamine, pyridine, diisopropylethyl amine, 2,6-lutidine, and the like. Appropriate solvents include, but are not limited to, methanol, ethanol, water, tetrahydrofuran, 1,2-dimethoxyethane, and ethyl acetate. Preferably the reaction is carried out in ethanol using triethylamine as the base. The reaction temperature is generally 25° C. and reaction time is 1 to 12 hours.

It will be appreciated by one skilled in the art that ketones of formula (17-2) can be transformed into alkenes of formula (8-2) and (18-7) via Wittig reaction with the appropriate phosphonium salt in the presence of a base, see (a) Burke, *Tetrahedron Lett.*, 1987, 4143-4146, (b) Rathke and Nowak, *J. Org. Chem.*, 1985, 2624-2626, (c) Maryanoff and Reitz, *Chem. Rev.*, 1989, 863-927. Furthermore, vinyl halides of formula (18-7) can be functionalized by Sonogashira coupling with alkynes in the presence of a palladium catalyst, a copper halide and an amine base to give compounds of formula (8-8) (see (a) Sonogashira, *Comprehensive Organic Synthesis*, Volume 3, Chapters 2,4; (b) Sonogashira, *Synthesis* 1977, 777.). In a similar manner, alkenes of formula (18-2) can be obtained from vinyl halides (18-7) via Suzuki cross coupling with organoboron reagents in the presence of a palladium catalyst and a base, or via Stille cross coupling with organostananes in the presence of a palladium catalyst (see (a) Suzuki, *J. Organomet. Chem.* 1999, 576, 147-168, (b) Stille, *Angew. Chem. Int. Ed. Engl.*, 1986, 508-524 (c) Farina, *J. Am. Chem. Soc.*, 1991, 9585-9595).

Furthermore, alcohols of type (18-3) can be prepared by reduction of the corresponding ketone of formula (17-2) under a variety of conditions (see Hudlicky, M. *Reductions in Organic Chemistry*, Ellis Horwood Limited: Chichester, 1984). The alcohols thus derived can be further modified to give compounds of formula (18-4). A process to generate compounds of formula (18-4) includes, but is not limited to, alkylation of the alcohol with an electrophile or conversion of the alcohol into a leaving group, such as a triflate, tosylate, phosphonate, halide, or the like, followed by displacement with a heteroatom nucleophile (e.g. an amine, alkoxide, sulfide or the like).

Yet another means by which to functionalize ketones of formula (17-2) is via addition of Grignard reagents to form alcohols of formula (18-5). The requisite Grignard reagents are readily available via the reaction of a variety of alkyl or aryl halides with magnesium under standard conditions (see B. S. Furniss, A. J. Hannaford, P. W. G. Smith, A. R. Tatchell, *Vogel's Textbook of Practical Organic Chemistry*, 5$^{th}$ ed., Longman, 1989). The addition is performed in an inert solvent, generally at low temperatures. Suitable solvents include, but are not limited to, tetrahydrofuran, diethylether, 1,4-dioxane, 1,2-dimethoxyethane, and hexanes. Preferably the solvent is tetrahydrofuran or diethylether. Preferably the reaction is run at −78° C. to 0° C.

In a similar way, reaction with other organometallic reagents gives rise to alcohols of formula (18-5). Examples of useful organometallic reagents include, but are not limited to, organo-aluminum, organo-lithium, organo-cerium, organo-zinc, organo-thallium, and organo-boron reagents. A more thorough discussion of organometallic reagents can be found in B. S. Furniss, A. J. Hannaford, P. W. G Smith, A. R. Tatchell, *Vogel's Textbook of Practical Organic Chemistry*, 5$^{th}$ ed., Longman, 1989.

Ketone of formula (17-2) can be further utilized by conversion into amine of formula (18-6) via a reductive amination. Reductive amination is achieved by treating the ketone with an amine in the presence of a reducing agent to obtain the product amine (18-6). The reaction can be carried out either with or without added acid. Examples of acids that are commonly used include, but are not limited to, hydrochloric acid, phosphoric acid, sulfuric acid, acetic acid, and the like. Reducing agents that effect reductive amination include, but are not limited to, hydrogen and a catalyst, zinc and hydrochloric acid, sodium cyanoborohydride, sodium borohydride, iron pentacarbonyl, and alcoholic potassium hydroxide. Generally alcoholic solvents are used. The preferred conditions use sodium cyanoborohydride in methanol or acetonitrile with added acetic acid.

It will be appreciated by one skilled in the art, that the unsaturated compounds represented by compounds (18-2) and (18-8) can be reduced to form the corresponding saturated compound (see Hudlicky, M., *Reductions in Organic Chemistry*, Ellis Horwood Limited: Chichester, 1984).

Scheme 19

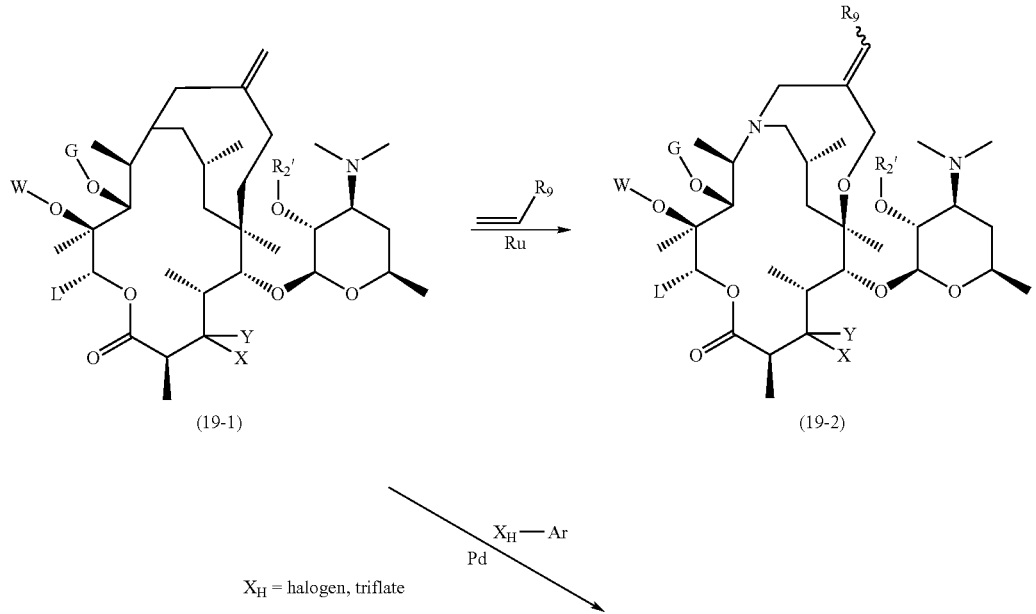

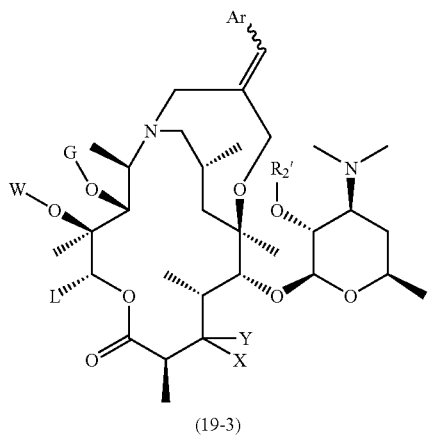

(19-3)

Compounds of the invention according to formula (19-1) are also capable of further functionalization to generate compounds of the present invention. Alkene (19-2) can be treated with an aryl halide or aryl triflate in the presence of a palladium catalyst [Pd(0) or Pd(II)] to provide compound (19-3): (See (a) Heck, *Palladium Reagents in Organic Synthesis*, Academic Press: New York, 1985, Chapter 1; (b) Sonogashira, *Comprehensive Organic Synthesis*, Volume 3, Chapters 2,4; (c) Sonogashira, *Synthesis* 1977, 777). Under the Heck coupling conditions, regioisomers and stereoisomers of the double bond are possible. Alternatively, compound (19-1) can undergo a cross metathesis reaction with vinylaromatic derivatives using ruthenium catalysts to give compounds of formula (19-2) (see (a) *J. Org. Chem.* 2000, 65, 2204-2207; (b) Reviews: *Synlett.* 1999, 2, 267; (c) Reviews: Ivin, K. J.; Mol, J. C., *Olefin Metathesis and Metathesis Polymerization*, $2^{nd}$ ed., Academic Press: New York, 1997; (d) *J. Org. Chem.* 1999, 64, 4798-4816; (e) *Angew. Chem., Int. Ed. Engl.* 1997, 36, 2036-2056; (f) *Tetrahedron* 1998, 54, 4413-4450).

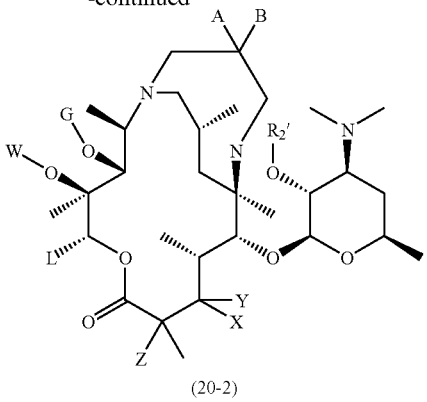

(20-2)

Scheme 20 illustrates compounds of formula (20-1), wherein A, B, G, L, W, X, Y and $R_2'$ are as previously defined, may be converted to compounds of formula (20-2), wherein A, B, G, L, W, X, Y, Z and $R_2'$ are as previously defined, with the same procedure as previously described in Scheme 7.

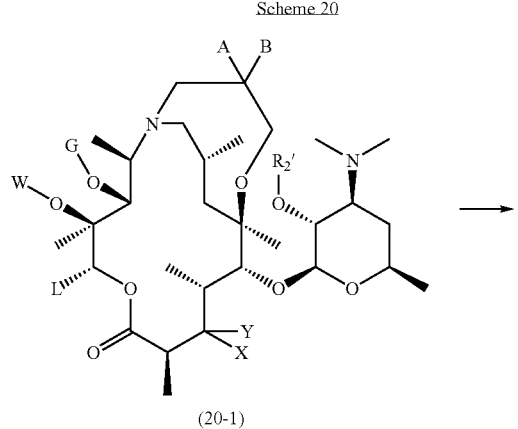

Scheme 20

(20-1)

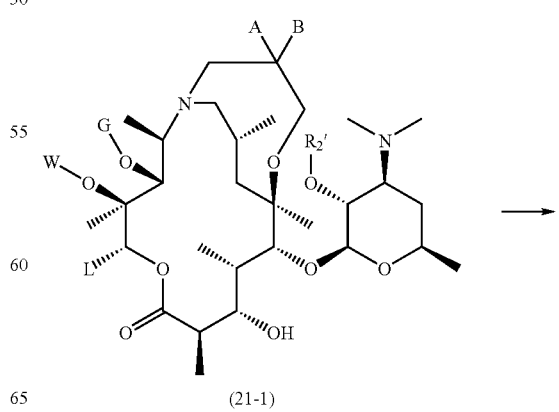

Scheme 21

(21-1)

Scheme 21 illustrates a procedure for the acylation of the C-3 hydroxyl of compounds of formula (21-1). The hydroxyl group is acylated under basic conditions using a suitable acylating agent in an aprotic solvent. Typical acylating agents include, but are not limited to, acid chlorides, acid anhydrides, and chloroformates.

Typical bases include, but are not limited to, pyridine, triethylamine, diisopropyl ethylamine, N-methyl morpholine, N-methyl pyrrolidine, 2,6-lutidine, 1,8-diazabicyclo[5.4.0]undec-7-ene. For a more extensive discourse on acylating conditions see for example, T. W. Greene and P. G. M. Wuts in "Protective Groups in Organic Synthesis" $3^{rd}$ ed., John Wiley & Son, Inc, 1999, referred to above herein.

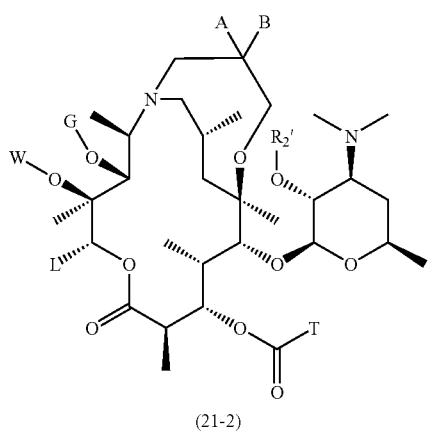

(21-2)

T = R, NHR, or $S(O)_nR$, where n and R are previously defined

Scheme 22

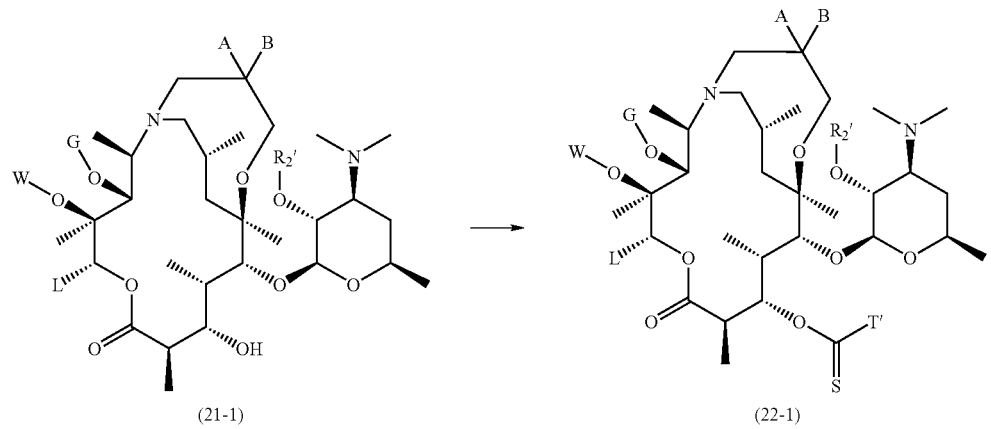

(21-1)  (22-1)

T' = SR or OR where R is as previously defined

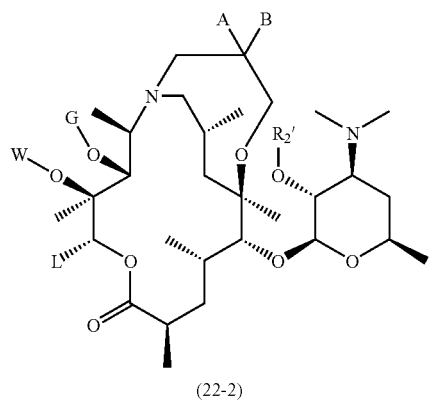

(22-2)

Another process of the invention, as illustrated in Scheme 22, involves the C-3 deoxygenation of the macrolide (21-1) which can be accomplished via the two step procedure shown therein. In the first step the xanthate or thiocarbonate is formed by the reaction of alkoxide of alcohol (21-1) with the appropriate thiocarbonyl. For instance, formation of the xanthate can be accomplished by reaction of the alkoxide with either carbondisulfide followed by methyliodide, or a dithiocarbonyl imidazole; whereas the thiocarbonate can be prepared by the reaction of the alkoxide with either thiocarbonyldimidazole followed by methanol, ethanol or the like, or a thiochloroformate. One skilled in the art will appreciate that other reagents and conditions exist to perform these transformations and that the examples above are for illustrative purposes only and do not limit the scope of this invention. These reactions are typically run in a polar aprotic solvent, preferably tetrahydrofuran, acetonitrile, or N,N dimethylformamide.

In the second step of Scheme 22, the thiocarbonate or xanthate is decomposed to give the alkane. Most typically this is done under radical conditions using, for example, a silyl hydride such as $(TMS)_3SiH$, $Ph_2SiH_2$ or the like, a tin hydride such as $Bu_3SnH$, $Ph_3SnH$ or the like, and a radical initiator such as AIBN or t-butyl peroxide. The preferred solvent is toluene.

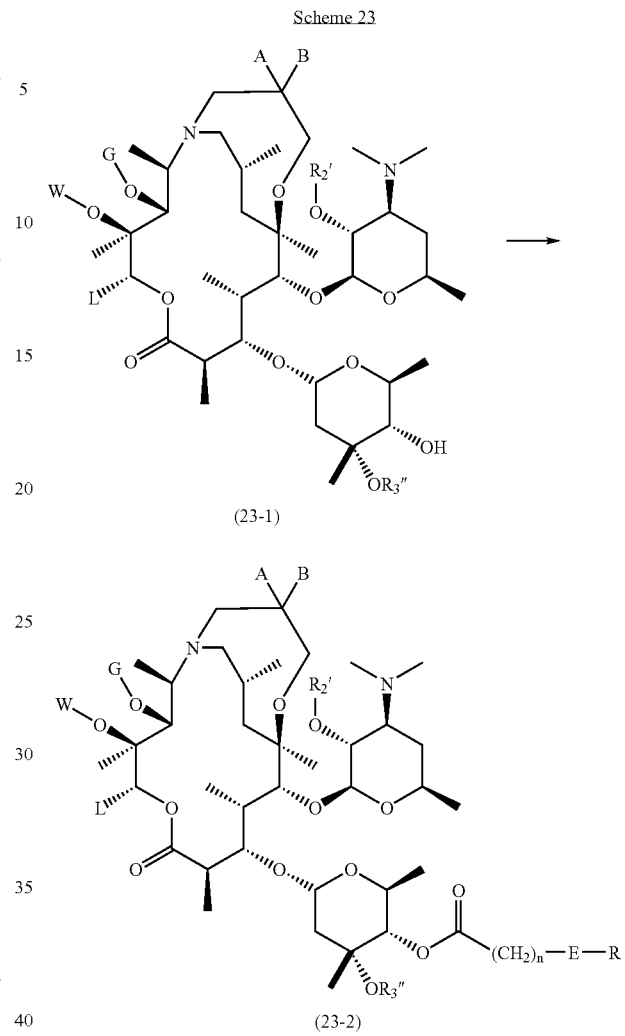

Scheme 23

Acylation of the 4"-hydroxy of the cladinose ring of compounds may be achieved via similar methods by acylation of the 3-position hydroxy delineated in Scheme 23 to form compounds of formula (23-2), where n, E and R are as previously defined. For further details concerning the acylation of the 4-hydroxy of the cladinose ring of compounds of formula (23-1), please see PCT Publication No. WO03/42228.

Scheme 24

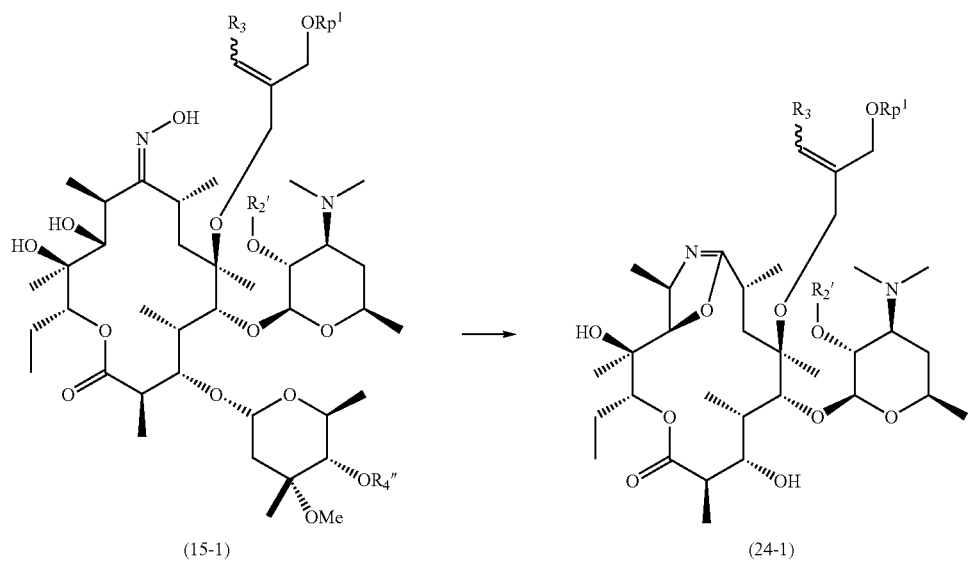

(15-1) (24-1)

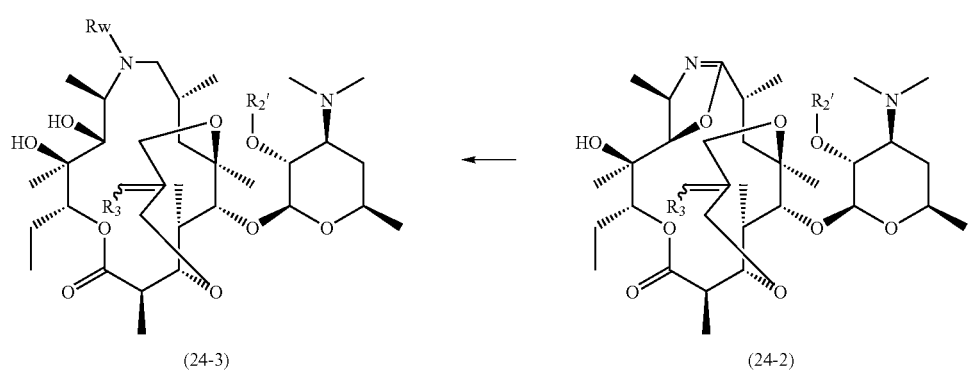

(24-3) (24-2)

Compounds of formula (15-1) can also be converted to the cyclized products (24-1) by removal of the cladinose sugar similarly as outlined in Scheme 5 followed by Beckmann rearrangement similarly as outlined in Scheme 3. The compounds of formula (24-1) can be cyclized intramolecularly with palladium to give the the compounds of formula (24-2) similarly as previously described in Scheme 4. The iminoether moiety can then be reduced to azalide (24-3, where Rw=H) similarly as previously described in Schemes 3 and 15 followed by reductive amination with appropriate aldehydes to form alkylated compounds of formula (24-3). Alternatively, compounds of formula (24-3) can also be made by reducing the iminoether moiety of (24-1) followed by reductive amination and subsequently cyclization with palladium.

Scheme 25

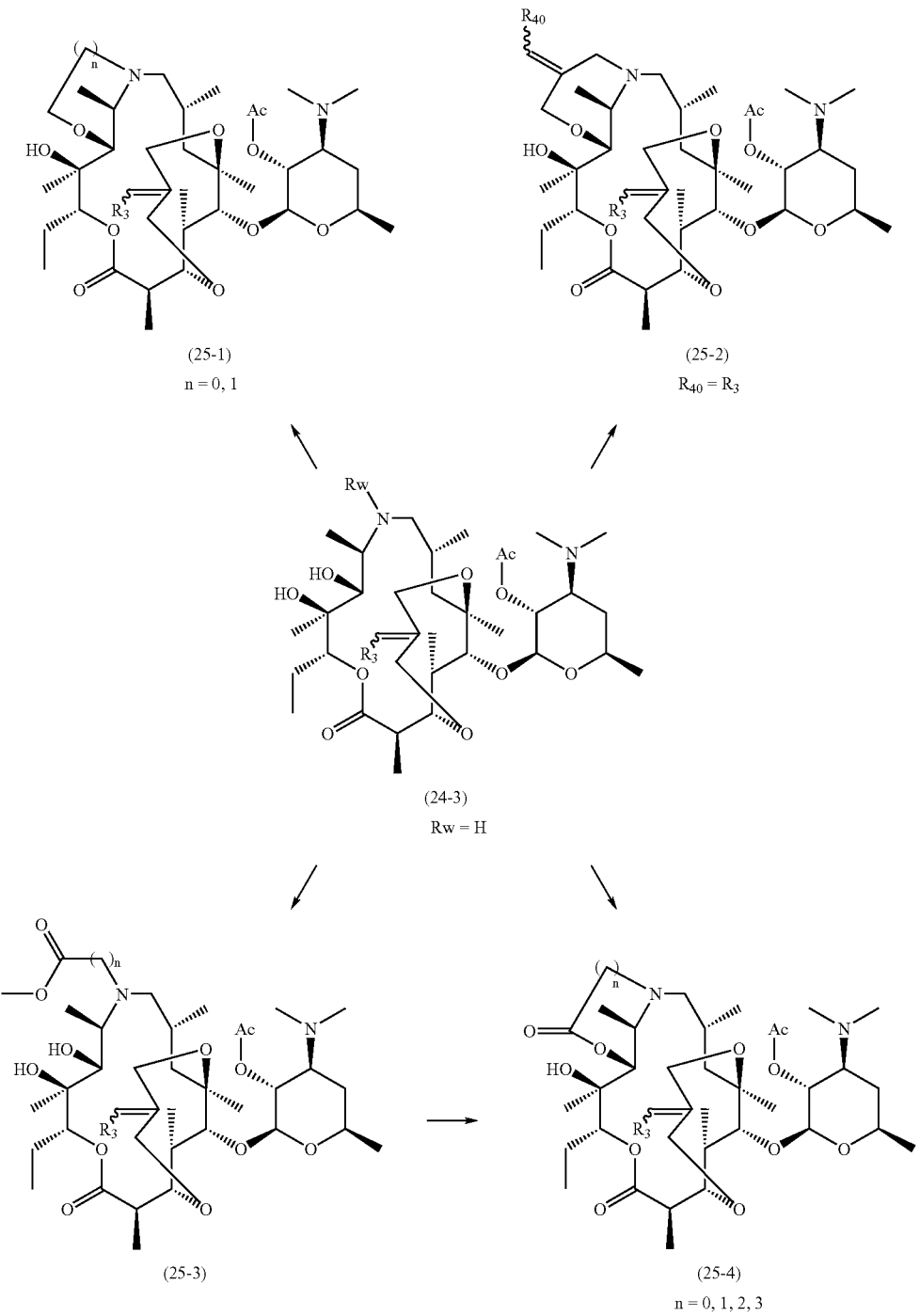

Compounds according to the invention of the formula (24-3, where Rw=H) can be further functionalized and cyclized in a variety of ways to provide compounds of formulae (25-1) to (25-4) by appropriate procedures known in the art. For example, as shown in Scheme 25, compounds of formula (25-1) where n=0 can be prepared by treating (24-3) with formaldehyde in methanol at room temperature. Compounds of formula (25-2) can be made from (24-3) and (14-1) via palladium chemistry as previously described in scheme 4. In addition, reductive amination of (24-3) first with functionalized aldehydes (25-3) followed by ester esterification yield compounds of formula (25-4). Compounds of formula (25-4) where n=0 can be made by treating (24-3) with CDI or any other phosgene equivalents known in the literature.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

Compound of Formula III, Wherein
A=B=G=W=Y=Z=hydrogen, L is —CH$_2$CH$_3$,
R$_2$'=Ac,

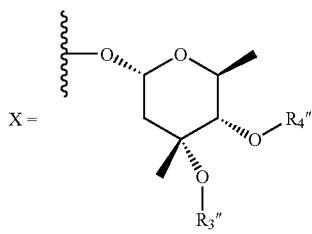

where R$_3$" is —CH$_3$ and R$_4$"=Ac.

Step 1a.

Acetic anhydride (35.9 mL, 0.38 mol), triethylamine (55.7 mL, 0.4 mol) and DMAP (3.7 g, 0.03 mol) were added to a solution of compound of Formula (1-1): (74.9 g, 0.1 mol) in 400 ml of THF at room temperature and the resulting mixture was stirred at room temperature for about 16 hours. The reaction mixture was concentrated to about 200 mL under reduced pressure, diluted with ethyl acetate (300 mL), washed with saturated NaHCO$_3$ (4×500 mL) and brine (500 mL). The organic phase was dried over sodium sulfate and the solvent was removed in vacuo. The solid residue was recrystallized from ethyl acetate to give the title compound (78 g).

MS (ESI) m/z: 875 (M+H)$^+$.

$^{13}$C-NMR(100 MHz, CDCl$_3$): δ 178.5, 175.4, 170.6, 170.2, 168.2, 100.2, 96.1, 83.3, 79.3, 78.7, 75.2, 74.5, 72.9, 70.0, 67.6, 63.4, 63.2, 60.6, 49.5, 44.7, 40.9, 35.4, 31.8, 28.5, 22.8, 21.7, 21.6, 21.5, 21.3, 21.2, 21.1, 19.9, 18.6, 18.4, 16.7, 14.9, 14.4, 14.3, 10.8, 9.2.

Step 1b.

Into a suspension of NaH (1.26 g, 50 mmol) in 40 ml of THF was added a solution of (Z)-2-butene-1,4-diol (4.4 g, 50 mmol) in THF (30 mL). The mixture was stirred at room temperature for 45 minutes and was added with a solution of tert-butyl dimethylsilyl chloride (7.54 g, 50 mmol) in THF (30 mL). The mixture was stirred at room temperature for 1 hour and quenched with saturated NaHCO$_3$ (200 mL). It was extracted with ether (2×150 mL) and the combined organics were dried over MgSO$_4$. The solvent was removed and the resulting oil was purified on silica chromatography (Hexane: ethyl acetate 10:1) to give the title compound (8.4 g).

Step 1c.

Into a solution of the compound from step 1b (8.1 g, 40 mmol) in CH$_2$Cl$_2$ (100 mL) was added Boc$_2$O (13.1 g, 60 mmol), tetrabutylammonium hydrogensulfate (1.2 g, 3.5 mmol) and aqueous NaOH (6 M, 30 mL). The mixture was stirred at room temperature for 16 hours. It was diluted with methylenechloride (100 mL) and washed with saturated NaHCO$_3$ (3×200 mL). The combined organics were dried over Na$_2$SO$_4$ and evaporated. The residue was purified on silica gel chromatography (Hexane:ethylacetate 96:4) to give the title compound (6.8 g).

Step 1d.

The compound from Step 1c (0.9 g, 3 mmol), 1,4-bis(diphenylphosphino)butane (170 mg, 0.4 mmol) and Pd$_2$(dba)$_3$ (183 mg, 0.2 mmol) were added into a solution of the compound from Step 1a (1.75 g, 2 mmol) in THF (10 ml) at room temperature. The reaction mixture was refluxed under nitrogen overnight, cooled to room temperature and the solvent was removed in vacuo. The residue was purified by silica gel chromatography (acetone:hexanes/1:3) to give the title compound (1.5 g).

MS (ESI) m/z: 1059 (M+H)$^+$.

$^{13}$C-NMR(100 MHz, CDCl$_3$): δ 181.2, 179.3, 175.9, 175.5, 173.5, 148.5, 116.5, 104.8, 102.0, 85.2, 84.3, 83.9, 83.6, 82.8, 82.2, 79.7, 78.1, 77.6, 75.6, 72.4, 70.4, 69.0, 68.6, 54.6, 49.9, 46.2, 43.2, 40.8, 36.5, 33.6, 31.4, 27.1, 27.0, 26.6, 26.3, 25.2, 25.1, 24.0, 23.7, 22.0, 20.4, 16.0, 15.2, 0.5, 0.0.

Step 1e.

A solution of the compound from Step 1d (10.594 g, 10 mmol) in THF (40 mL) and pyridine (10 mL) was treated with hydrogen fluoride-pyridine (1.0 mL) at room temperature for 48 hours when more pyridine (3 mL) and hydrogen fluoride-pyridine (1.0 mL) were charged and the mixture was stirred for another 64 hours. It was evaporated and the residue was partitioned (EtOAc and saturated NaHCO$_3$). The organic was washed (saturated NaHCO$_3$, water and brine), dried (Na$_2$SO$_4$) and evaporated. Chromatography (silica, hexane: acetone 85:15~2:3) gave the title compound (8.194 g). MS (ESI) m/z: 945 (M+H)$^+$.

Step 1f.

A solution of the compound from Step 1e (2.598 g, 2.75 mmol) in CH$_2$Cl$_2$ (20 mL) was treated with acetic anhydride (0.40 mL, 4.23 mmol) at room temperature for 20 hours before DMAP (5 mg) was charged and the mixture was stirred for another 20 hours. It was evaporated and the residue was partitioned (EtOAc and saturated NaHCO$_3$). The organic was washed (saturated NaHCO₃, water and brine), dried (Na₂SO₄) and evaporated. Chromatography (silica, hexane: acetone 85:15~1:1) gave the title compound (2.671 g).

MS (ESI) m/z: 987 (M+H)⁺.

Step 1g.

A solution of the compound from Step 1f (1.849 g, 1.87 mmol) in isopropanol (20 mL) was treated with ammonium hydroxide (28%, 10 mL) at room temperature for 3 hours before evaporation. The residue was chromatographed (silica, hexane:acetone 4:1~7:3) to give the title compound (1.471 g).

MS (ESI) m/z: 945 (M+H)⁺.

$^{13}$C-NMR(100 MHz, CDCl₃): δ 174.7, 171.5, 170.4, 170.0, 169.6, 132.7, 125.6, 99.4, 96.0, 79.2, 78.4, 78.2, 77.2, 77.0, 76.7, 76.5, 74.0, 72.6, 71.9, 70.1, 66.9, 65.0, 63.9, 63.1, 49.1, 44.3, 40.6, 37.8, 36.4, 35.1, 32.8, 30.9, 25.3, 21.54, 21.52, 21.4, 21.0, 20.9, 20.8, 18.8, 18.3, 16.3, 15.9, 15.0, 10.5, 9.2.

Step 1h.

A solution of the compound from Step 1g (521 mg, 0.55 mmol) in CH₂Cl₂ (5 mL) was treated with p-toluenesulfonyl anhydride (359 mg, 1.10 mmol) in the presence of Et₃N (0.38 mL, 2.75 mmol) at room temperature for 2 hours before evaporation. The residue was partitioned (EtOAc and 5% K₂CO₃). The organic was washed (water and brine), dried (Na₂SO₄) and evaporated. Chromatography (silica, hexane:acetone 9:1~3:2 containing 0.5% Et₃N) gave the title compound (481 mg).

MS (ESI) m/z: 927 (M+H)⁺ and 464 (M+2H)²⁺.

Step 1i.

A mixture of the compound from Step 1h (30 mg, 0.032 mmol), NaBH₃CN (5.2 mg, 0.083 mmol) in MeCN (4.5 mL), ethylene glycol (0.25 mL) and HOAc (0.5 mL) was stirred at room temperature for 15.5 hours before partition (EtOAc and 10% K₂CO₃). The organic was washed (water and brine), dried (Na₂SO₄) and evaporated. Chromatography (silica, hexane:acetone then CH₂Cl₂:2M NH₃/MeOH) gave the title compound (~10 mg).

MS (ESI) m/z: 931 (M+H)⁺ and 466 (M+2H)²⁺.

Step 1j.

A solution of the compound from Step 1i (~10 mg, ~0.01 mmol) and tetrakis(triphenylphosphine)palladium (4.7 mg, 0.004 mmol) in THF (3 ml) is heated at 65° C. under nitrogen for 14 hours before being cooled to room temperature and evaporated. The residue is purified by silica gel chromatography (acetone:hexanes 1:9~3:7) to give the title compound (13 mg).

MS (ESI) m/z: 871 (M+H)⁺ and 436 (M+2H)²⁺.

Example 2

Compound of Formula III, Wherein A=B=G=W=Y=Z=R₂'=Hydrogen L is —CH₂CH₃,

X = 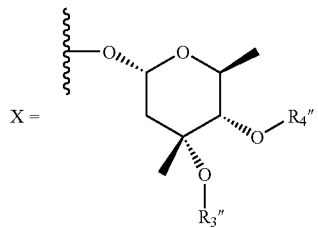

where R₃" is —CH₃ and R₄"=Ac.

A solution of the compound from Step 1j in MeOH is heated at 55° C. for 17 hours before being cooled to room temperature and evaporated. The residue is purified by silica gel chromatography to give the title compound.

Example 3

Compound of Formula III, Wherein A=B=G=W=Y=Z=R₂'=Hydrogen, L is —CH₂CH₃,

X = 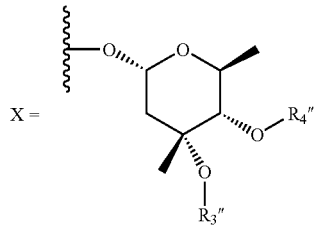

where R₃" is —CH₃ and R₄"=H.

A solution of the compound from Example 2 in THF-isopropanol (1:1, 5 mL) is treated with LiOH (1 M, 2.5 mL) at room temperature for 3 hours before partition (EtOAc/saturated NaHCO₃). The organic is washed (water and brine), dried (Na₂SO₄) and evaporated. The residue is purified by silica gel chromatography (CH₂Cl₂:2M NH₃/MeOH) to give the title compound.

Example 4

Compound of Formula III Wherein A=B=G=W=X=Y=Z=R₂'=hydrogen, L is —CH₂CH₃

To a solution of the title compound of Example 3 in ethanol (5 ml) is added 2N HCl (5 ml) at room temperature. The resulting reaction mixture is heated to 70° C. and stirred at that temperature for 1 hour. The reaction is then quenched with saturated $K_2CO_3$ extracted with ethyl acetate. The extract is dried over $Na_2SO_4$ and the solvent is removed in vacuo. The residue is purified via flash chromatography ($SiO_2$, 2M $NH_3$ in methanol/$CH_2Cl_2$=5/95) to give the title compound.

Example 5

Compound of Formula VIII, Wherein $R_{14}$ and $R_{15}$ Taken Together with the Carbon Atom to which They are Attached are CHCH=$CH_2$, G=W=Y=Z=Hydrogen, L is —$CH_2CH_3$, $R_2'$=Ac, X = 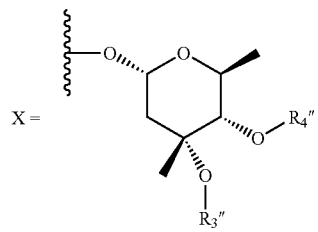

where $R_3''$ is —$CH_3$ and $R_4''$=Ac.

The title compound is prepared in conjunction with the title compound of example 1 by the procedure described in Step 1j of example 1.

Example 6

Compound of Formula VIII, Wherein $R_{14}$ and $R_{15}$ Taken Together with the Carbon Atom to which They are Attached are CHCH=CH, G=W=Y=Z=$R_2'$=hydrogen, L is —$CH_2CH_3$, X = 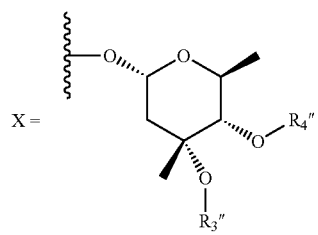

where $R_3''$ is —$CH_3$ and $R_4''$=Ac;

A solution of the compound from example 5 in MeOH is heated at 55° C. for 17 hours before being cooled to room temperature and evaporated. The residue is purified by silica gel chromatography to give the title compound.

Example 7

Compound of Formula VIII, Wherein $R_{14}$ and $R_{15}$ Taken Together with the Carbon Atom to which They are Attached are CHCH=$CH_2$, G=W=Y=Z=$R_2'$=hydrogen, L is —$CH_2CH_3$, X = 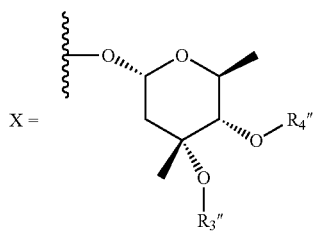

where $R_3''$ is —$CH_3$ and $R_4$=H.

A solution of the compound from Example 6 in THF-isopropanol (1:1, 5 mL) is treated with LiOH (1 M, 2.5 mL) at room temperature for 3 hours before partition (EtOAc/saturated $NaHCO_3$). The organic is washed (water and brine), dried ($Na_2SO_4$) and evaporated. The residue is purified by silica gel chromatography ($CH_2Cl_2$:2M $NH_3$/MeOH) to give the title compound.

Example 8

Compound of Formula IX, Wherein $R_{14}$ and $R_{15}$ Taken Together with the Carbon Atom to which They are Attached are C=$CH_2$, G=W=Y=Z=Hydrogen, L is —$CH_2CH_3$, $R_2'$=Ac, X = 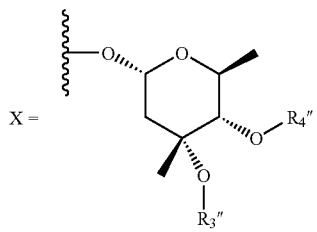

where $R_3''$ is —$CH_3$ and $R_4''$=Ac.

Step 8a.

A suspension of NaH (1.26 g, 50 mmol) in 40 ml of THF was added a solution of 2-methylene-1,3-propanediol (4.4 g, 50 mmol) in 30 ml of THF. The mixture was stirred at room temperature for 45 minutes and was added with a solution of tert-butyl dimethylsilyl chloride (7.54 g, 50 mmol) in 30 ml of THF. The mixture was stirred at room temperature for 1 hour and quenched with saturated $NaHCO_3$ (200 ml). Extracted with ether (150 ml×2) and the combined organic layers were dried over $MgSO_4$. The solvent was removed and the resulting oil was purified on silica chromatography (Hexane:ethyl acetate/10:1) to give the title compound (8.4 g).

Step 8b.

A solution of compound from step 8a (8.1 g, 40 mmol) in 100 ml of methylenechloride was added Boc$_2$O (13.1 g, 60 mmol), tetrabutylammoniahydrogensulfate (1.2 g, 3.5 mmol) and 30 ml of 6N NaOH. The mixture was stirred at room temperature for 16 hours. Diluted with 100 ml of methylenechloride and washed with saturated NaHCO$_3$ (200 mlX3). The organic layer was dried over Na$_2$SO$_4$. The solvent was removed and the residue was purified on silica gel chromatography (Hexane:ethylacetate/96:4) to give the title compound (6.8 g).

Step 8c.

The compound from Step 8b, tert-Butyl-OC(O)—OCH$_2$(C=CH$_2$)CH$_2$—O-tert-butyldimethylsilyl (0.9 g, 3 mmol) and 1,4-bis(diphenylphosphino)butane (170 mg, 0.4 mmol) and Pd$_2$(dba)$_3$ (183 mg, 0.2 mmol) were added into a solution of the compound from Step 1a of Example 1 (1.75 g, 2 mmol) in tetrahydrofuran (10 ml) at room temperature. The reaction mixture was refluxed under nitrogen overnight, cooled to room temperature and the solvent was removed in vacuo. The residue was purified by silica gel chromatography to give the title compound (acetone:hexanes/1:3) (1.5 g).

MS (ESI) m/z: 1059.65 (M+H).

$^{13}$C-NMR(100 MHz, CDCl$_3$): δ 181.2, 179.3, 175.9, 175.5, 173.5, 148.5, 116.5, 104.8, 102.0, 85.2, 84.3, 83.9, 83.6, 82.8, 82.2, 79.7, 78.1, 77.6, 75.6, 72.4, 70.4, 69.0, 68.6, 54.6, 49.9, 46.2, 43.2, 40.8, 36.5, 33.6, 31.4, 27.1, 27.0, 26.6, 26.3, 25.2, 25.1, 24.0, 23.7, 22.0, 20.4, 16.0, 15.2, 0.5, 0.0.

Step 8d.

A stock solution of HF-Pyridine in THF (7 ml, 8.5 mmol) was added to a solution of the compound from step 8c (2.65 g, 2.5 mmol) in 15 ml THF and 1.5 ml Pyridine. The mixture was stirred at room temperature for 2 days. Diluted with ethyl acetate (80 ml) and washed with saturated NaHCO$_3$ (100 ml×2). The solvent was removed in vacuo and the residue was purified by silica gel chromatography to give the title compound (acetone:hexanes/1:3).(2.1 g).

MS (ESI) m/z: 945.51 (M+H).

$^{13}$C-NMR(100 MHz, CDCl$_3$): δ 176.6, 175.3, 170.3, 168.7, 146.3, 113.3, 99.7, 96.6, 80.2, 78.6, 77.6, 74.5, 72.9, 72.3, 70.2, 67.3, 65.2, 63.6, 63.4, 63.0, 49.4, 44.8, 41.0, 37.9, 37.0, 35.6, 34.7, 31.3, 29.5, 28.4, 21.9, 21.8, 21.6, 21.5, 21.1, 20.1, 20.0, 18.7, 16.9, 16.6, 15.2, 10.7, 9.7.

Step 8e.

To a solution of the compound from step 8d (3.0 g, 3.2 mmol) in 20 ml anhydrous CH$_2$Cl$_2$ was added acetic anhydride (0.4 ml, 4.2 mmol), triethylamine (0.8 ml, 5.8 mmol) and DMAP (10 mg, cat.) at room temperature. After stirring for 12 h, the reaction was quenched by saturated NaHCO$_3$ aqueous solution (10 ml). The organic layer was then washed with 10 ml saturated NaHCO$_3$ aqueous solution, and 5 ml water. The organic layer was dried over Na$_2$SO$_4$ and filtered. The solvent was removed in vacuo to give the title compound (3.2 g).

MS (ESI) m/z: 987.2 (M+H).

$^{13}$C-NMR(100 MHz, CDCl$_3$): δ 176.4, 174.3, 171.1, 170.6, 170.0, 139.6, 114.6, 99.8, 96.8, 79.0, 78.7, 78.3, 77.1, 74.6, 72.9, 72.3, 70.3, 67.3, 65.4, 64.8, 63.5, 49.4, 46.2, 44.7, 41.0, 37.9, 36.9, 35.6, 34.7, 31.2, 28.4, 21.9, 21.8, 21.6, 21.5, 21.3, 21.1, 20.1, 20.0, 18.7, 16.9, 16.6, 15.2, 10.7, 9.8.

Step 8f.

The compound from Step 8e (2.1 g, 2.1 mmol) was dissolved in isopropanol (16 ml) and ammonia hydroxide (4 ml). After stirring for 2 hours at room temperature, the reaction mixture was diluted with ethyl acetate (200 m), washed with water (20 ml) and brine (30 ml ×2). The organic layer was dried over Na$_2$SO$_4$ and filtered. The solvent was removed in vacuo to give the title compound (1.9 g).

MS (ESI) m/z: 945.2 (M+H).

$^{13}$C-NMR(100 MHz, CDCl$_3$): δ 174.4, 172.1, 170.7, 170.5, 170.3, 141.2, 113.4, 99.7, 96.6, 80.4, 78.9, 78.7, 78.6, 77.1, 74.3, 72.9, 72.2, 71.0, 67.2, 65.7, 65.6, 63.5, 63.4, 49.4, 44.8, 41.0, 37.9, 36.8, 35.6, 34.5, 31.3, 25.5, 21.9, 21.8, 21.6, 21.4, 21.3, 21.2, 21.1, 20.1, 18.7, 16.7, 15.4, 10.7, 9.8.

Step 8g.

To a solution of the compound from Step 8f (0.1 g, 0.1 mmol) in 5 ml anhydrous CH$_3$CN was added toluenesufonic anhydride (41.5 mg, 0.12 mmol) and triethylamine (0.02 ml, 0.15 mmol) at −20° C. The reaction mixture was slowly warmed up to room temperature within 1 hour. NaBH$_3$CN (63 mg, 1.0 mmol), acetic acid (0.2 ml) was added into the reaction. The mixture was stirred for 10 hours and the reaction was quenched by saturated NaHCO$_3$ aqueous solution (50 ml). The mixture was extracted with CH$_2$Cl$_2$ (5 ml×5). The organic layer was dried over Na$_2$SO$_4$ and filtered. The solvent was removed and the residue was purified on silica gel chromatography (Hexane:acetone/1:1) to give the title compound (30 mg).

MS (ESI) m/z: 931.2 (M+H), 466.3 (M+2H).

Step 8h.

To a solution of the compound from Step 8g (10 mg, 0.01 mmol) in 2 ml anhydrous THF was added Pd$_2$(dba)$_3$ (2.0 mg, 0.002 mmol) and dppb (2.0 mg, 0.004 mmol). The mixture was briefly degassed and was heated to 65° C. for 4 hours under nitrogen. The solvent was removed and the residue was purified on silica gel chromatography (3% 2M NH$_3$/MeOH in CH$_2$Cl$_2$) to give the title compound (5.0 mg).

MS (ESI) m/z: 871.5 (M+H), 436.4 (M+2H).

Example 9

Compound of Formula IX, Wherein $R_{14}$ and $R_{15}$ Taken Together with the Carbon Atom to which They are Attached are $C=CH_2$, $G=W=Y=Z=R_2'=$Hydrogen, L is $-CH_2CH_3$,

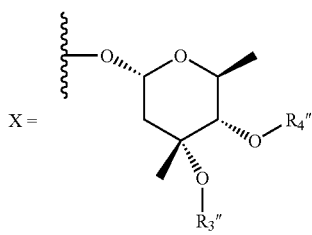

where $R_3''$ is $-CH_3$ and $R_4''=Ac$.

The compound from Step 8h of Example 8 (3 mg, 0.0035 mmol) in 3 ml MeOH was heated at 55° C. for 10 hours. The solvent was removed and the residue was filtered through a short pad of silica gel (5% 2M NH3/MeOH in $CH_2Cl_2$) to give the title compound (2.2 mg).

MS (ESI) m/z: 829.4 (M+H), 415.4 (M+2H).

Example 10

Compound of Formula X, Wherein $R_{14}$ and $R_{15}$ Taken Together with the Carbon Atom to which They are Attached are $C=CH_2$, $G=W=$hydrogen, $R_2'=Ac$, L is $-CH_2CH_3$, D is $-NHCH_2-$ Step 10a.

A solution of the compound from Step 8c of Example 8 (3.2 g, 3 mmol) in isopropanol (40 mL) was treated with HCl (2 M, 20 mL) at 70° C. for 2 hours before being cooled to room temperature. It was neutralized with $K_2CO_3$ and extracted with EtOAc. The organics were dried ($Na_2SO_4$) and evaporated. The residue was chromatographed (silica, hexanes-acetone) to give the title compound (1.6 g, 76%).

MS (ESI) m/z: 703 (M+H)$^+$.

$^{13}$C-NMR(125 MHz, CDCl$_3$): δ 175.4, 170.5, 170.3, 146.4, 114.0, 99.6, 80.1, 79.8, 77.8, 77.2, 74.3, 71.0, 68.8, 63.9, 63.7, 63.5, 44.4, 40.7, 37.1, 36.6, 33.6, 31.4, 25.7, 21.9, 21.8, 21.4, 20.6, 19.6, 16.8, 15.6, 15.5, 10.7, 8.4.

Step 10b.

A solution of the compound from Step 10a (1.92 g, 2.74 mmol) in $CH_2Cl_2$ (15 mL) was treated with acetic anhydride (0.81 mL, 9.6 mmol) at room temperature for 71 hours in the presence of triethylamine (2.0 mL, 14.6 mmol) before evaporation. The residue was chromatographed (silica, hexane: acetone) to give the title compound (1.90 g, 88%).

MS (ESI) m/z: 787 (M+H)$^+$.

$^{13}$C-NMR(125 MHz, CDCl$_3$): δ 176.6, 174.5, 171.0, 170.3, 168.8, 139.8, 117.0, 99.7, 80.2, 80.0, 77.5, 77.4, 74.5, 71.5, 70.3, 69.0, 65.2, 63.4, 63.3, 44.4, 40.8, 37.1, 36.3, 34.9, 31.3, 28.4, 22.1, 21.8, 21.4, 21.1, 20.5, 20.0, 16.9, 15.7, 15.4, 10.7, 8.4.

Step 10c.

A solution of the compound from Step 10b (1.90 g, 2.4 mmol) in isopropanol (20 mL) was treated with ammonium hydroxide (28%, 5 mL) at room temperature for 130 minutes before evaporation. The residue was chromatographed (silica, hexane:acetone) to give the title compound (1.64 g, 91%).

MS (ESI) m/z: 745 (M+H)$^+$.

$^{13}$C-NMR(125 MHz, CDCl$_3$): δ 174.6, 171.9, 170.2, 170.1, 140.6, 114.6, 99.7, 80.4, 80.3, 77.7, 77.4, 74.3, 71.5, 71.1, 68.9, 65.6, 64.1, 63.3, 44.5, 40.7, 37.0, 36.2, 33.6, 31.3, 25.4, 22.9, 22.0, 21.7, 21.4, 21.3, 20.4, 19.6, 16.8, 15.7, 15.5, 10.7, 8.4.

Step 10d.

A solution of the compound from Step 10c (521 mg, 0.55 mmol) in $CH_2Cl_2$ (7 mL) was treated with p-toluenesulfonic anhydride (326 mg, 1.0 mmol) in the presence of $Et_3N$ (0.49 mL, 3.5 mmol) at room temperature for 14.5 hours before evaporation. The residue was partitioned (EtOAc and 5% $K_2CO_3$). The organic was washed (water and brine), dried ($Na_2SO_4$) and evaporated. Chromatography (silica, hexane: acetone containing 0.5% $Et_3N$) gave the title compound (327 mg).

MS (ESI) m/z: 727 (M+H)$^+$ and 364 (M+2H)$^{2+}$.

Step 10e.

A mixture of the compound from Step 10d (72.3 mg, 0.1 mmol), $Pd_2(dba)_3$ (18.3 mg, 0.02 mmol) and dppb (17.0 mg, 0.04 mmol) in THF (5 ml) was heated at 75° C. (bath) under nitrogen for 14 hours before being cooled to room temperature and evaporated. The residue was purified by silica gel chromatography (acetone:hexanes containing 0.5% $Et_3N$) to give the title compound (32 mg).

MS (ESI) m/z: 667 (M+H)$^+$ and 334 (M+2H)$^{2+}$

Step 10f.

A mixture of the compound from Step 10e (30 mg, 0.032 mmol), NaBH$_3$CN (5.2 mg, 0.083 mmol) in MeCN (4.5 mL), ethylene glycol (0.25 mL) and HOAc (0.5 mL) is stirred at room temperature for 15.5 hours before partition (EtOAc and 10% $K_2CO_3$). The organic is washed (water and brine), dried ($Na_2SO_4$) and evaporated. Chromatography (silica, hexane: acetone then $CH_2Cl_2$:2M NH$_3$/MeOH) give the title compound.

Example 11

Compound of Formula X, Wherein $R_{14}$ and $R_{15}$ Taken Together with the Carbon Atom to which They are Attached are $C=CH_2$, $G=W=$hydrogen, $R_2'=Ac$, L is $-CH_2CH_3$, D=-N(CH$_3$)CH$_2-$ Step 11a.

A mixture of the compound from Step 10d of Example 10 (100 mg, 0.14 mmol), NaBH$_3$CN (25.9 mg, 0.41 mmol) in MeCN (5 mL), ethylene glycol (0.46 mL) and HOAc (0.47 mL) was stirred at room temperature for 15 hours before partition (EtOAc and 10% $K_2CO_3$). The organic was washed (water and brine), dried ($Na_2SO_4$) and evaporated. Chromatography (silica, hexane:acetone then $CH_2Cl_2$:2M NH$_3$/MeOH) gave the title compound (46 mg).

MS (ESI) m/z: 731 (M+H)$^+$ and 366 (M+2H)$^{2+}$.

Step 11b.

A mixture of the compound from Step 11a (46 mg, 0.063 mmol), NaBH$_3$CN (5.4 mg, 0.086 mmol) and 37% aqueous formaldehyde (0.1 mL) in MeCN (3 mL) and HOAc (0.15 mL) was stirred at room temperature for 35 minutes before partition (EtOAc and 10% K$_2$CO$_3$). The organic was washed (water and brine), dried (Na$_2$SO$_4$) and evaporated. Chromatography (silica, hexane:acetone then CH$_2$Cl$_2$:2M NH$_3$/MeOH) gave the title compound (10 mg).

MS (ESI) m/z: 745 (M+H)$^+$ and 373 (M+2H)$^{2+}$.

Step 11c.

A mixture of the compound from Step 11b (10 mg, 0.01 mmol), Pd$_2$(dba)$_3$ (6.1 mg, 0.007 mmol) and dppb (5.7 mg, 0.013 mmol) in THF (5 ml) was heated at 75° C. (bath) under nitrogen for 18 hours before being cooled to room temperature and evaporated. The residue was purified by silica gel chromatography (acetone:hexanes) to give the title compound (5 mg).

MS (ESI) m/z: 685 (M+H)$^+$ and 343 (M+2H)$^{2+}$.

Example 12

Compound of Formula X Wherein R$_{14}$ and R$_{15}$ Taken Together with the Carbon Atom to which They are Attached are C=CH$_2$, G=W=R$_2$'=hydrogen, L is —CH$_2$CH$_3$, D=-N(CH$_3$)CH$_2$—

The compound from Step 11c of Example 11 (4.6 mg) in MeOH (2 mL) was heated at 65° C. for 3.5 hours. The solvent is removed and the residue was filtered through a short pad of silica gel (2M NH$_3$/MeOH—CH$_2$Cl$_2$) to give the title compound (3.0 mg). MS (ESI) m/z: 643 (M+H)$^+$ and 322 (M+2H)$^{2+}$.

Example 13

Compound of Formula X, Wherein R$_{14}$ and R$_{15}$ Taken Together with the Carbon Atom to which They are Attached are C=CH-[5-(2-(2-pyridyl)thiophene)], G=W=R$_2$'=hydrogen, L is —CH$_2$CH$_3$, D=-N(CH$_3$)CH$_2$—

To a solution of the compound from Example 12 (0.7 mmol) in 8 ml anhydrous DMF, 2-(5-bromo-thiophen-2-yl)-pyridine (1.2 mmol) (prepared according to patent WO 03/097659 A1) and K$_2$CO$_3$ (1.5 mmol) are added at room temperature. The mixture is degassed briefly and a catalytic amount of POPd is added. The reaction mixture is heated to 100° C. in a sealed tube for 48 hours. Ethyl acetate (50 mL) is added and the solution is washed 3 times with aqueous NaHCO$_3$. The organic layer is dried over anhydrous Na$_2$SO$_4$. The solvent is evaporated under vacuum and the residue is purified by flash chromatography (SiO$_2$, acetone:hexanes/1:1) to provide the title compound.

Example 14

Compound of Formula X, Wherein R$_{14}$ and R$_{15}$ Taken Together with the Carbon Atom to which They are Attached are C=O, G=W=R$_2$'=hydrogen, L is —CH$_2$CH$_3$, D=-N(CH$_3$)CH$_2$—

Step 14a.

The compound from step 10e (1.725 g, 2.6 mmol) in acetone (10 mL), ethanol (10 mL), and water (10 mL) was treated with NaIO$_4$ (1.66 g, 7.76 mmol) in the presence of OsO$_4$ (4 wt % in H$_2$O, 2.0 mL, ~0.33 mmol) at room temperature for 2.5 hours before partition (EtOAc and saturated NaHCO$_3$ and 10% Na$_2$S$_2$O$_3$). The organics were washed (water and brine) and dried (Na$_2$SO$_4$). Chromatography (silica, acetone: hexanes) gave the title compound (1.268 g, 73%).

MS (ESI) m/z: 669 (M+H)$^+$ and 335 (M+2H)$^{2+}$.

Step 14b.

The compound from step 14a (586 mg, 0.88 mmol) in THF (7 mL) was treated with LiAlH(OBu$^t$)$_3$ (1 M in THF, 2.0 mL, 2.0 mmol) at room temperature for 4 hours before partition (EtOAc and 5% NaOH). The organics were washed (water and brine) and dried (Na$_2$SO$_4$). Evaporation gave the crude title compound (576 mg, 98%).

MS (ESI) m/z: 671 (M+H)$^+$ and 336 (M+2H)$^{2+}$.

Step 14c.

The compound from step 14b (550 mg, 0.82 mmol) in HOAc (6 mL) was hydrogenated (60 psi) at room temperature for 72 hours in the presence of platinum oxide (51 mg) before filtration. The filtrate was evaporated and the residue was dissolved in EtOAc. It was washed (water and brine) and dried (Na$_2$SO$_4$). Chromatography (silica, CH$_2$Cl$_2$:2M ammonia in methanol) gave the title compound (458 mg, 83%).

MS (ESI) m/z: 675 (M+H)$^+$ and 338 (M+2H)$^{2+}$.

Step 14d.

The compound from step 14c (288 mg, 0.43 mmol) in CHCl$_3$ (8 mL) was treated with formaldehyde (37% aqueous, 0.057 mL, 0.76 mmol) and formic acid (0.04 mL, 1.06 mmol) at 70° C. for 3 hours in the presence of platinum oxide (51 mg) before partition (EtOAc and 10% K$_2$CO$_3$). The organics were washed (water and brine) and dried (Na$_2$SO$_4$). Chromatography (silica, CH$_2$Cl$_2$:2M ammonia in methanol) gave the title compound (240 mg, 82%).

MS (ESI) m/z: 689 (M+H)$^+$ and 345 (M+2H)$^{2+}$.

Step 14e.

The compound from step 14d (33 mg, 0.048 mmol) in CH$_2$Cl$_2$ (3 mL) was treated with Dess-Martin Periodinane (43.8 mg, 0.10 mmol) at 0° C. for 3 hours before partition (EtOAc and 5% NaOH). The organics were washed (water and brine) and dried (Na$_2$SO$_4$). Chromatography (silica, CH$_2$Cl$_2$:2M ammonia in methanol) gave the title compound (28 mg, 85%).

MS (ESI) m/z: 687 (M+H)$^+$ and 344 (M+2H)$^{2+}$.

Step 14f.

The compound from step 14e (9 mg) in methanol (1 mL) was stood at room temperature for 25 hours before evaporation. Chromatography (silica, $CH_2Cl_2$:2M ammonia in methanol) gave the title compound (5 mg).

MS (ESI) m/z: 645 $(M+H)^+$ and 323 $(M+2H)^{2+}$.

Example 15

Compound of Formula X, Wherein $R_{14}$ and $R_{15}$ Taken Together with the Carbon Atom to which They are Attached are C=N—O—$CH_2$-[5-(2-(1-pyrazolyl)pyridine)], G=W=$R_2'$=hydrogen, L is —$CH_2CH_3$, D=-N($CH_3$)$CH_2$—

Step 15a.

A solution of the compound from step 14e of Example 14 (20.9 mg, 0.03 mmol) and o-(6-pyrazol-1-yl-pyridin-3-ylmethyl)-hydroxylamine (prepared according to patent WO 03/097659 A1) (25.3 mg, 0.13 mmol) in ethanol (3 mL) and aqueous HCl (1 M, 0.5 mL) was stirred at 0° C. for 75 minutes before acetone was charged. It was partitioned (EtOAc and 10% $K_2CO_3$). The organics were washed (water and brine) and dried ($Na_2SO_4$). Evaporation gave the crude title compound used directly for next step.

MS (ESI) m/z: 859 $(M+H)^+$ and 430 (M+2H)2+.

Step 15b.

The crude compound from step 15a (9 mg) in methanol (1 mL) was stood at room temperature for 21 hours before evaporation. Chromatography (silica, $CH_2Cl_2$:2M ammonia in methanol) gave the title compound (18.9 mg) as a 2.4:1 mixture.

MS (ESI) m/z: 817 $(M+H)^+$ and 409 $(M+2H)^{2+}$.

Example 16

Compound of Formula X, Wherein $R_{14}$ and $R_{15}$ Taken Together with the Carbon Atom to which They are Attached are CH—OH, G=W=$R_2'$=hydrogen. L is —$CH_2CH_3$, D=-N($CH_3$)$CH_2$—

To a solution of compound from step 14d of Example 14 (11 mg) in MeOH (2 mL) was heated at 50° C. for 19 hours before evaporation. Chromatography (silica, $CH_2Cl_2$:2M ammonia in methanol) gave the title compound (7.5 mg, 73%).

MS (ESI) m/z: 647 $(M+H)^+$ and 324 $(M+2H)^{2+}$.

Example 17

Compound of Formula X, Wherein $R_{14}$ and $R_{15}$ Taken Together with the Carbon Atom to which They are Attached are —CH—O—$CH_2$C≡CH, G=W=$R_2'$=hydrogen, L is —$CH_2CH_3$, D=-N($CH_3$)$CH_2$—

To a solution of compound from Example 16 in DMSO and THF mixture (1:2) is added a propargyl bromide and then immediately potassium tert-butoxide at 0° C. The mixture is allowed to stir at 0° C. for 6 hours, then is quenched with sodium bicarbonate and is extracted with ethyl acetate, dried and concentrated under vacuum. The residue is purified by flash chromatography to give the title compound.

Example 18

Compound of Formula X, Wherein $R_{14}$ and $R_{15}$ Taken Together with the Carbon Atom to which They are Attached are CH—O—$CH_2$C≡C-[5-(2-(2-pyridyl)thiophene)], G=W=$R_2'$=hydrogen, L is —$CH_2CH_3$, D=-N($CH_3$)$CH_2$—

To a solution of the compound from Example 17 in 8 ml anhydrous acetonitrile, 2-(5-bromo-thiophen-2-yl)-pyridine (prepared according to patent WO 03/097659 A1) and triethyl are added at room temperature. The mixture is degassed briefly and a catalytic amount of Pd(PPh$_3$)$_4$ and copper(I) iodide are added. The reaction mixture is heated to 80° C. in a sealed tube for 24 hours. Ethyl acetate is added and the solution is washed 3 times with aqueous NaHCO$_3$. The organic layer is dried over anhydrous Na$_2$SO$_4$. The solvent is evaporated under vacuum and the residue is purified by flash chromatography (SiO$_2$, acetone:hexanes/1:1) to provide the title compound.

Example 19

Compound of Formula X Wherein $R_{14}$ and $R_{15}$ Taken Together with the Carbon Atom to which They are Attached are CH—O—$CH_2$CH=CH-[5-(2-(2-pyridyl)thiophene)], G=W=$R_2'$=hydrogen, L is —$CH_2CH_3$, D=-N($CH_3$)$CH_2$—

A solution of compound from Example 18 in methanol is kept under H$_2$ in the presence of Pd/C for 18 hours. The reaction mixture is filtered through Celite and the solvent is removed in vacuo to give the title compound.

Example 20

Compound of Formula XI, Wherein $R_{14}$ and $R_{15}$ Taken Together with the Carbon Atom to which They are Attached are C=$CH_2$, W=hydrogen. $R_2'$=Ac. L is —$CH_2CH_3$, P=$CH_2$ A compound from Step 10f of Example 10 is stirred in a mixture of aqueous formaldehyde and methanol at room temperature for 18 hours. The mixture is concentrated under vacuo to half of its volume and is then extracted with ethyl acetate, washed with brine, dried (Na2SO4), filtered and concentrated under vacuum. The residue is purified by flash chromatography (SiO$_2$, acetone:hexanes/1:1) to provide the title compound.

Example 21

Compound of Formula XI, Wherein $R_{14}$ and $R_{15}$ Taken Together with the Carbon Atom to which They are Attached are C=O, W=$R_2'$=hydrogen, L is —$CH_2CH_3$, P=$CH_2$ The title compound is prepared with the title compound of Example 20 via the same conditions described in Example 12 and Example 14.

Example 22

Compound of Formula XI, Wherein $R_{14}$ and $R_{15}$ Taken Together with the Carbon Atom to which They are Attached are C=CH-[5-(2-(2-pyridyl)thiophene)], W=$R_2$'=hydrogen, L is —CH$_2$CH$_3$, P=CH$_2$ The title compound is prepared with the title compound of Example 20 via the same conditions described in Example 13.

Example 23

Compound of Formula XI, Wherein $R_{14}$ and $R_{15}$ Taken Together with the Carbon Atom to which They are Attached are C=N—O—CH$_2$-[5-(2-(1-pyrazolyl)pyridine)], W=$R_2$'=hydrogen, L is —CH$_2$CH$_3$, P=CH$_2$ The title compound is prepared with the title compound of Example 21 via the same conditions described in Example 15.

Example 24

Compound of Formula XI, Wherein $R_{14}$ and $R_{15}$ Taken Together with the Carbon Atom to which They are Attached are C—O—CH$_2$C≡CH, W=$R_2$'=hydrogen L is —CH$_2$CH$_3$, P=CH$_2$ The title compound is prepared with the title compound of Example 21 via the same conditions described in Example 16 and Example 17.

Example 25

Compound of Formula XI, Wherein $R_{14}$ and $R_{15}$ Taken Together with the Carbon Atom to which They are Attached are CH—O—CH$_2$C=C-[5-(2-(2-pyridyl)thiophene)], W=$R_2$'=hydrogen, L is —CH$_2$CH$_3$, P=CH$_2$ The title compound is prepared with the title compound of Example 24 via the same conditions described in Example 18.

Example 26

Compound of Formula XI, Wherein $R_{14}$ and $R_{15}$ Taken Together with the Carbon Atom to which They are Attached are CH—O—CH$_2$CH=CH-[5-(2-(2-pyridyl)thiophene)], W=$R_2$'=hydrogen, L is —CH$_2$CH$_3$, P=CH$_2$ The title compound is prepared with the title compound of Example 25 via the same conditions described in Example 19.

Example 27

Compound of Formula X, Wherein $R_{14}$ and $R_{15}$ Taken Together with the Carbon Atom to which They are Attached are CH—O—CH$_2$CH=CH-(3-quinoline), G=W=$R_2$'=hydrogen, L is —CH$_2$CH$_3$, D=-N(CH$_3$)CH$_2$—

Step 27a.

A mixture of the compound from Step 14d (40 mg, 0.058 mmol), tert-Butyl-OC(O)—OCH$_2$CH=CH-(3-quinoline) (33.1 mg, 0.12 mmol) and 1,4-bis(diphenylphosphino)butane (12.4 mg, 0.029 mmol) and Pd$_2$(dba)$_3$ (13.3 mg, 0.014 mmol) in tetrahydrofuran (5 ml) was refluxed under nitrogen for 15.5 hours, cooled to room temperature and the solvent was removed in vacuo. The residue was purified by silica gel chromatography to give the title compound (18.7 mg).

MS (ESI) m/z: 856.1 (M+H) and 428.7 (M+2H)$^{2+}$.

Step 27b.

To a solution of compound from step 27a (18.7 mg) in MeOH (2 mL) was stood at room temperature for 23.5 hours before evaporation. Chromatography (silica, CH$_2$Cl$_2$:2M ammonia in methanol) gave the title compound (13.4 mg).

MS (ESI) m/z: 814.1 (M+H)$^+$ and 407.7 (M+2H)$^{2+}$.

Example 28

Compound of Formula XI, Wherein $R_{14}$ and $R_{15}$ Taken Together with the Carbon Atom to which They are Attached are CH—OH, W=$R_2$'=hydrogen, L is —CH$_2$CH$_3$, P=CH$_2$C(=CH$_2$)CH$_2$ Step 28a.

A mixture of 2-methylene-1,3-propanediol (10.0 g, 0.12 mol), pyridine (30.0 mL, 0.38 mol) and acetic anhydride (30.0 mL, 0.32 mol) in methylene chloride (30 mL) was stirred at room temperature for 16 hours before DMAP (50 mg) was charged. It was stirred for another 24 h before evaporation. The residue was partitioned (hexanes and water). The aqueous layer was extracted with ether. The combined organics were washed (4 M HCl, saturated NaHCO$_3$) and dried (Na$_2$SO$_4$). Evaporation gave the title compound (16.7 g, 85%)

Step 28b.

A mixture of the compound from Step 14d (50 mg, 0.074 mmol), the compound of step 28a (25.5 mg, 0.15 mmol) and 1,4-bis(diphenylphosphino)butane (15.8 mg, 0.037 mmol) and Pd$_2$(dba)$_3$ (16.9 mg, 0.018 mmol) in tetrahydrofuran (4 ml) was refluxed under nitrogen for 3 hours, cooled to room temperature and the solvent was removed in vacuo. The residue was purified by silica gel chromatography to give the title compound (50 mg).

MS (ESI) m/z: 727 (M+H) and 364 (M+2H)$^{2+}$.

Step 28c.

To a solution of compound from step 28b (50 mg) in MeOH (3 mL) was stood at room temperature for 25 hours before evaporation. Chromatography (silica, CH$_2$Cl$_2$:2M ammonia in methanol) gave the title compound (41 mg).

MS (ESI) m/z: 685 (M+H)$^+$ and 343 (M+2H)$^{2+}$.

Example 29

Compound of Formula XI, Wherein R$_{14}$ and R$_{15}$ Taken Together with the Carbon Atom to which They are Attached are CH—OH, W═R$_2$'═hydrogen L is —CH$_2$CH$_3$, P═CH(CH═CH$_2$)CH$_2$ Step 29a.

A mixture of the compound from Step 14d (49.3 mg, 0.073 mmol), AcOCH$_2$CH═CHCH$_2$OAc (25.1 mg, 0.15 mmol) and 1,4-bis(diphenylphosphino)butane (15.8 mg, 0.037 mmol) and Pd$_2$(dba)$_3$ (16.9 mg, 0.018 mmol) in tetrahydrofuran (4 ml) was refluxed under nitrogen for 1 hour, cooled to room temperature and the solvent was removed in vacuo. The residue was purified by silica gel chromatography to give the title compound (50 mg) as a 2.4:1 mixture.

MS (ESI) m/z: 727.6 (M+H) and 364.4 (M+2H)$^{2+}$.

Step 29b.

To a solution of compound from step 29a (50 mg) in MeOH (3 mL) was stood at room temperature for 27 hours before evaporation. Chromatography (silica, CH$_2$Cl$_2$:2M ammonia in methanol) gave the title compound (40 mg).

MS (ESI) m/z: 685.6 (M+H)$^+$ and 343.4 (M+2H)$^{2+}$.

Although the invention has been described with respect to various preferred embodiments, it is not intended to be limited thereto, but rather those skilled in the art will recognize that variations and modifications may be made therein which are within the spirit of the invention and the scope of the appended claims.

What is claimed:

1. A compound represented by formula (I) or (II):

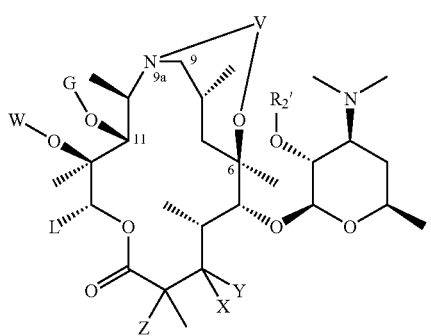

(I)

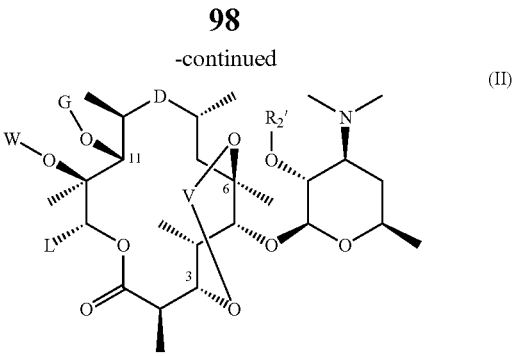

(II)

as well as the pharmaceutically acceptable salts, and esters thereof, wherein V is selected from the group consisting of:

(a) —CH$_2$—C(A)═C(B)-CH$_2$—;
wherein,
A and B are independently selected from the group consisting of:
  (i) hydrogen;
  (ii) deuterium;
  (iii) halogen;
  (iv) R$_1$, wherein R$_1$ is dependently selected from C$_1$-C$_6$ alkyl, C$_2$-C$_6$ alkenyl, or C$_2$-C$_6$ alkynyl, containing 0, 1, 2 or 3 heteroatoms selected from O, S or N, optionally substituted with one or more substituents selected from the group consisting of: halogen, aryl, substituted aryl, heteroaryl, and substituted heteroaryl;
  (v) R$_2$, wherein R$_2$ is independently selected from the group consisting of:
    a. aryl;
    b. heteroaryl;
    c. substituted aryl; and
    d. substituted heteroaryl;
  (vi) —(C$_1$-C$_3$-alkyl)-M-(C$_1$-C$_3$-alkyl)-R$_2$, wherein M═—O—, —NH—, —N(CH$_3$)—, —NHC(O)— or —S(O)$_n$—, wherein n =0, 1 or 2, and R$_2$ is as previously defined;
  (vii) —(C$_1$-C$_3$-alkyl)-M-R$_2$, wherein M and R$_2$ are as previously defined;
  (viii) —C(O)-J-R$_3$, wherein J is absent, O or S, and R$_3$ is H, R$_1$ or R$_2$; where R$_1$ and R$_2$ are as previously defined, and
  (ix) —C(O)—NR$_4$R$_5$, wherein R$_4$ and R$_5$ are each independently selected from the group consisting of:
    a. hydrogen;
    b. R$_1$, wherein R$_1$ is as previously defined;
    c. R$_2$, wherein R$_2$ is as previously defined; and
    d. R$_4$ and R$_5$ taken together with the nitrogen atom to which they are connected form a 3- to 7-membered ring which may optionally contain one or more heterofunctions selected from the group consisting of: —O—, —NH—, —N(R1)—, —N(R$_2$)—, —S(O)$_n$—, wherein n, R$_1$ and R$_2$ are as previously defined;

(b) —CH$_2$—CH(A)-C(B)═CH—, wherein A and B are as previously defined;

(c) —CH═C(A)-CH(B)-CH$_2$—, wherein A and B are as previously defined;

(d) —CH$_2$—CH(A')-CH(B')-CH$_2$—;
wherein A' and B' are independently selected from the group consisting of:

(i) A, wherein A is as previously defined;
(ii) —OH;
(iii) —OR$_p$, wherein R$_p$ is a hydroxy protecting group;
(iv) —O—R$_9$, wherein R$_9$ is R$_1$ or R$_2$, and wherein R$_1$ and R$_2$ are as previously defined;
(v) —S(O)$_n$R$_9$, wherein n and R$_9$ are as previously defined;
(vi) —NHC(O)R$_3$, wherein R$_3$ is as previously defined;
(vii) —NHC(O)NR$_4$R$_5$, wherein R$_4$ and R$_5$ are as previously defined;
(viii) —NHS(O)$_2$R$_9$, wherein R$_9$ is as previously defined;
(ix) —NHR$_{13}$, wherein R$_{13}$ is an amino protecting group; and
(x) —NR$_4$R$_5$, wherein R$_4$ and R$_5$ are as previously defined;

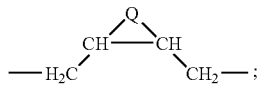 (e)

wherein:
(i) -Q- is selected from the group consisting of:
—O—;  —O—C(O)—CH(R$_7$)—;  —N(R$_7$)—;
—O—C(O)—N(R$_7$)—;  —O—C(O)—O—;
—N(R$_7$)—N=N—;  —C(R$_7$)=N—O—; and
—CH(R$_7$)—N(R$_8$)—O—; wherein R$_7$ and R$_8$ are independently selected from R$_3$, wherein R$_3$ is as previously defined; or
(ii) -Q- taken together with the two carbon atoms it is attached to is selected from the group consisting of:
a. cycloalkylene;
b. cycloalkenylene; and
c. heterocycloalkylene; and
(f) —CH$_2$—C(R$_{11}$)(R$_{12}$)—CH$_2$—CH$_2$—;
wherein R$_{11}$ and R$_{12}$ taken together with the carbon atom to which they are attached are selected from the group consisting of:
(i) C=O;
(ii) C(OR$_{1a}$)(OR$_{2a}$), where R$_{1a}$ and R$_{2a}$ are independently R$_1$ or taken together are —(CH$_2$)$_m$—, and where m is 2 or 3;
(iii) C(SR$_{1a}$)(SR$_{2a}$), where R$_{1a}$ and R$_{2a}$ are as previously defined;
(iv) C=CHR$_3$, where R$_3$ is as previously defined;
(v) C=N—O—R$_3$, where R$_3$ is as previously defined;
(vi) C=NNHR$_3$, where R$_3$ is as previously defined;
(vii) C=NNHC(O)R$_3$, where R$_3$ is as previously defined;
(viii) C=NNHC(O)NR$_4$R$_5$, where R$_4$ and R$_5$ are as previously defined;
(ix) C=NNHS(O)$_2$R$_9$, where R$_9$ is as previously defined;
(x) C=NNHR$_{13}$, where R$_{13}$ is as previously defined; and
(xi) C=NR$_9$, where R$_9$ is as previously defined;
(g) —C(R$_{14}$)(R$_{15}$)—CH$_2$—;
wherein R$_{14}$ is:
(i) —OR$_p$, where R$_p$ is previously defined;
(ii) —R$_1$, where R$_1$ is as previously described;
(iii) —R$_2$, where R$_2$ is as previously described;
(iv) —OR$_1$, where R$_1$ is as previously defined;
(v) —OR$_2$, where R$_2$ is previously defined;
(vi) —S(O)$_n$R$_9$, where n and R$_9$ are as previously defined;
(vii) —NHC(O)R$_9$, where R$_9$ is as previously defined;
(viii) —NHC(O)NHR$_9$, where R$_9$ is as previously defined;
(ix) —NHS(O)$_2$R$_9$, where R$_9$ is as previously defined;
(x) —NR$_4$R$_5$, where R$_4$ and R$_5$ are as previously defined;
(xi) —NHR$_{13}$, where R$_{13}$ is previously defined; and
R$_{15}$ is:
(i) deuterium;
(ii) halogen;
(iii) —OH;
(iv) —R$_1$, where R$_1$ is as previously defined;
(v) —R$_2$, where R$_2$ is as previously defined; or
(vi) —OR$_p$, where R$_p$ is as previously defined, provided that when R$_{15}$ is halogen, —OH or OR$_p$, R$_{14}$ is R$_1$ or R$_2$, where R$_1$ and R$_2$ are previously defined;
or, alternatively, R$_{14}$ and R$_{15}$ taken together with the carbon atom to which they are attached are:
(i) C=O;
(ii) C(OR$_{1a}$)(OR$_{2a}$), where R$_{1a}$ and R$_{2a}$ are independently R$_1$ or taken together are —(CH$_2$)$_m$—, and where m is 2 or 3;
(iii) C(SR$_{1a}$)(SR$_{2a}$), where R$_{1a}$ and R$_{2a}$ are as previously defined;
(iv) C=CHR$_9$, where R$_9$ is as previously defined;
(v) C=N—O—R$_9$, where R$_9$ is as previously defined;
(vi) C=NNHR$_9$, where R$_9$ is as previously defined;
(vii) C=NNHC(O)R$_9$, where R$_9$ is as previously defined;
(viii) C=NNHC(O)NHR$_9$, where R$_9$ is as previously defined;
(ix) C∇NNHS(O)$_2$R$_9$, where R$_9$ is as previously defined;
(x) C=NNHR$_9$, where R$_9$ is as previously defined; or
(xi) C=NR$_9$, where R$_9$ is as previously defined;
(h) —CH$_2$—C(R$_{14}$)(R$_{15}$)—CH$_2$—; wherein R$_{14}$ and R$_{15}$ as previously defined;
G and W are independently selected from:
(a) hydrogen;
(b) R$_{10}$, where R$_{10}$ is C$_1$-C$_6$-alkyl, C$_2$-C$_6$-alkenyl or C$_2$-C$_6$-alkynyl, containing 0, 1, 2, or 3 heteroatoms, optionally substituted with one or more substituents selected from:
(1) halogen;
(2) aryl;
(3) substituted-aryl;
(4) heteroaryl;
(5) substituted-heteroaryl;
(6) —O—C$_1$-C$_6$-alkyl-R$_9$, where R$_9$ is as previously defined; and
(7) —N(R$_1$R$_5$), where R$_4$ and R$_5$ are as previously defined;
(c) —C(O)R$_9$, where R$_9$ is as previously defined;
(d) —C(O)O—R$_9$, where R$_9$ is as previously defined; and
(e) —C(O)N(R$_4$R$_5$), where R$_4$ and R$_5$ are as previously defined;
Or, alternatively, G and W are taken together to form either a carbonyl or a methylene group,
L is:
(a) —CH$_2$CH$_3$;
(b) —CH(OH)CH$_3$;
(c) -R$_1$, where R$_1$ is as previously defined,
D is —N(R$_{19}$)CH$_2$—, —N(R$_{20}$)C(O)—, or —N=C(OR$_{20}$)—, wherein R$_{20}$ is R$_9$ where R$_9$ is as previously defined;

$R_{19}$ is
(a) hydrogen;
(b) —$C_1$-$C_{12}$-alkyl, $C_2C_{12}$-alkenyl, or $C_2C_{12}$alkynyl, containing 0, 1, 2, or 3 heteroatoms, all optionally substituted with one or more substituents independently selected from:
  i) halogen;
  ii) —$OR_1$, wherein $R_1$ is as previously defined;
  iii) —$OR_2$, wherein $R_2$ is as previously defined;
  iv) —$NR_4R_5$, where $R_4$ and $R_5$ as previously defined or alternatively $R_4$ and $R_5$, together with the atom to which they are attached, form a heterocycloalkyl or substituted heterocycloalkyl moiety;
  v) =N—O—$R_9$, where $R_9$ is as previously defined;
  vi) —$R_1$, where $R_1$ is as previously defined;
  vii) —$C_3$-$C_8$-cycloalkyl;
  viii) substituted —$C_3$-$C_8$-cycloalkyl;
  ix) heterocycloalkyl;
  x) substituted heterocycloalkyl;
  xi) —$NHC(O)R_9$, where $R_9$ is as previously defined;
  xii) —$NHC(O)OR_9$, where $R_9$ is as previously defined;
  xiii) —$NHC(O)NR_4R_5$, where $R_4$ and $R_5$ are as previously defined;
  xiv) —$OC(O)NR_4R_5$, where $R_4$ and $R_5$ are as previously defined;
  xv) —$OC(O)R_9$, where $R_9$ is as previously defined;
  xvi) —$OC(O)OR_9$, where $R_9$ is as previously defined;
  xvii) —$OC(O)NR_4R_5$, where $R_4$ and $R_5$ are as previously defined,
  xviii) —$C(O)R_9$, where $R_9$ is as previously defined,
  xix) —$CO_2R_9$, where $R_9$ is as previously defined, or
  xx) —$C(O)NR_4R_5$, where $R_4$ and $R_5$ are as previously defined;
Alternatively, D when taken together with G to form a moiety of the following structure:

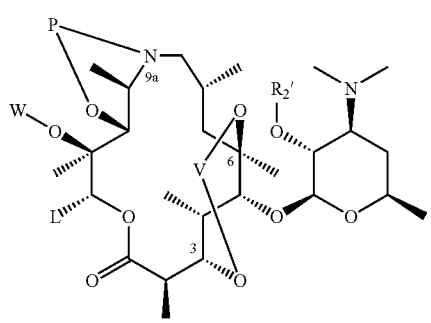

(IIa)

wherein L, V, W and $R_2'$ are as previously defined and P is C1-C6 alkyl optionally substituted with one or more substituents selected from the group consisting of:
  a) $R_1$, where $R_1$ is as previously defined;
  b) $R_2$, where $R_2$ is as previously defined;
  c) heterocycloalkyl,
  d) hydroxyl,
  e) C1-C6-alkoxy,
  f) Halogen, and
  g) $NR_4R_5$ where $R_4$ and $R_5$ are as previously defined,
X is hydrogen;
Y is
  (a) hydrogen;
  (b) —OH;
  (c) —$OR_p$, where $R_p$ is as previously defined;
  (d) —$OR_9$, where $R_9$ is as previously defined;
  (e) —$OC(O)R_9$, where $R_9$ is as previously defined;
  (f) —$OC(O)NHR_9$, where $R_9$ is as previously defined;
  (g) —$S(O)_nR_9$, where n and $R_9$ are as previously defined;

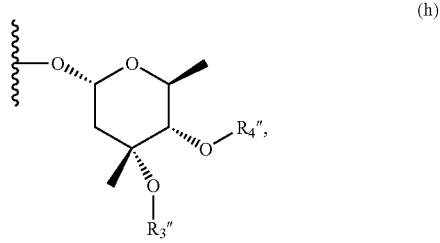

(h)

where $R_3''$ is selected from hydrogen or methyl and $R_4''$ is selected from:
  (1) hydrogen;
  (2) $R_p$, where $R_p$ is as previously defined; or
  (3) —$C(O)(CH_2)_r$-E-$R_9$, wherein $R_9$ is as previously defined, r =1-6 and E is absent or -$U(CH_2)_qU'$-, where q =an integer from 2 to 8, and U and U' are independently selected from:
    i) —$N(R_9)$—, where $R_9$ is as previously defined;
    ii) —O—;
    iii) —$S(O)_n$—, where n =0, 1, or 2;
    iv) —$N(R_9)C(O)$—, where $R_9$ is as previously defined;
    v) —$C(O)N(R_9)$—, where $R_9$ is as previously defined; or
    vi) —$N[C(O)R_9]$—, where $R_9$ is as previously defined; and
Alternatively, X and Y taken together are oxo;
Z is
  (a) hydrogen;
  (b) methyl; or
  (c) halogen; and
$R_2'$ is hydrogen or $R_p$, where $R_p$, is as previously defined.

2. A compound according to claim 1 represented by formula III:

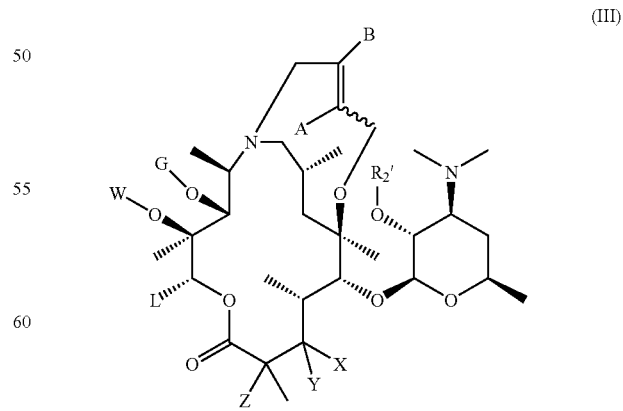

(III)

wherein A, B, G, L, W, X, Y, Z and $R_2'$ are as previously defined in claim 1.

3. A compound according to claim 1 represented by formulae IVa and IVb:

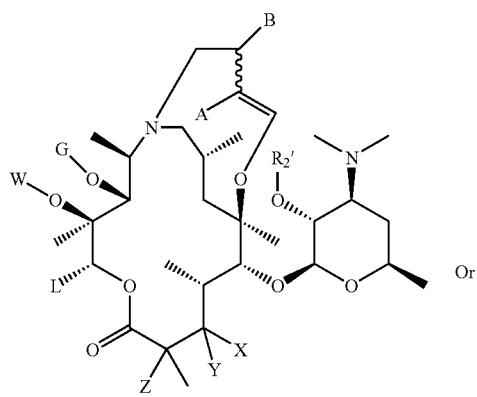

(IVa)

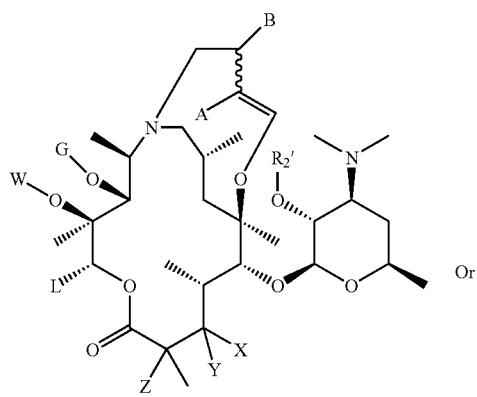

(IVb)

wherein A, B, G, L, W, X, Y, Z and $R_2'$ are as previously defined in claim 1.

4. A compound according to claim 1 represented by formula V:

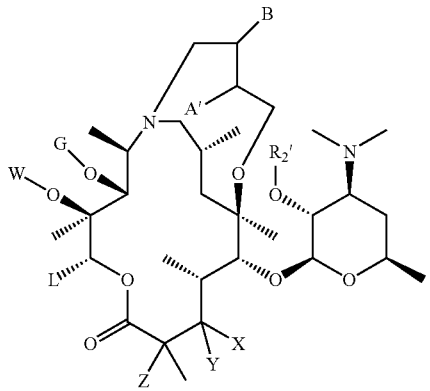

(V)

wherein A', B', G, L, W, X, Y, Z, and $R_2'$ are as previously defined in claim 1.

5. A compound according to claim 1 represented by formula VI:

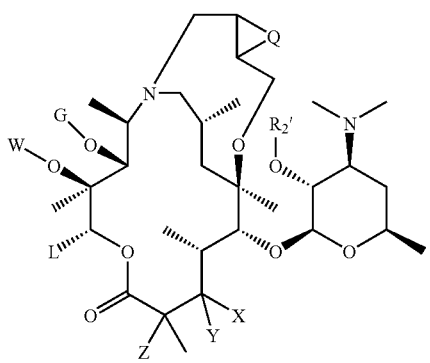

(VI)

wherein G, L, Q, W, X, Y, Z, and $R_2'$ are as previously defined in claim 1.

6. A compound according to claim 1 represented by formulae VIIa and VIIb:

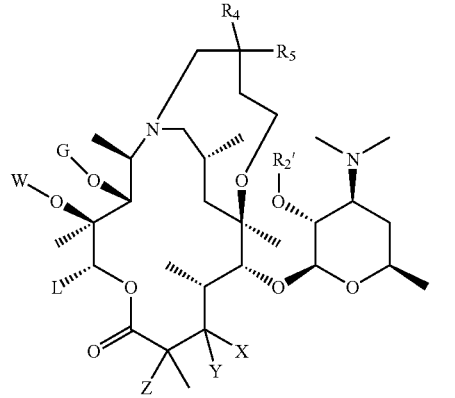

(VIIa)

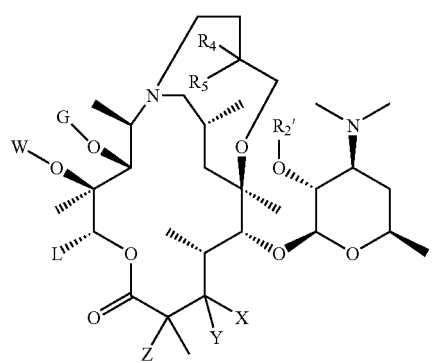

(VIIb)

wherein G, L, W, X, Y, Z, $R_2'$, R4 and R5 are as previously defined in claim 1.

7. A compound according to claim 1 represented by formula VIII:

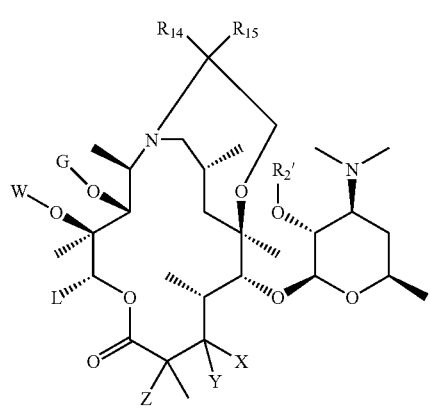

(VIII)

wherein G, L, W, X, Y, Z, $R_{14}$, $R_{15}$ and $R_2'$ are as previously defined in claim 1.

8. A compound according to claim 1 represented by formula IX:

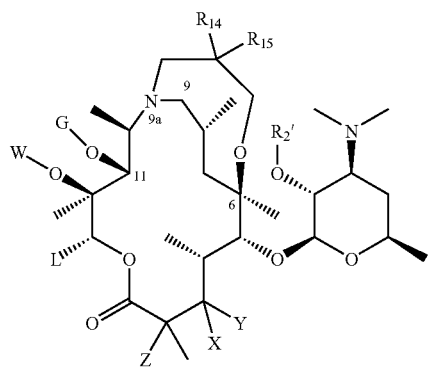

(IX)

wherein G, L, W, X, Y, Z, $R_{14}$, $R_{15}$ and $R_2'$ are as previously defined in claim 1.

9. A compound according to claim 1 represented by formula X:

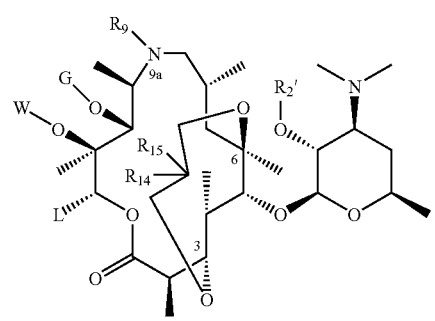

(X)

wherein G, L, W, X, Y, Z, $R_{14}$, $R_{15}$ and $R_2'$ are as previously defined in claim 1.

10. A compound according to claim 1 represented by formula XI:

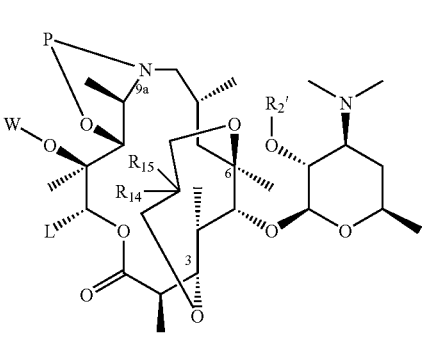

(XI)

wherein G, L, P, W, X, Y, Z, $R_{14}$, $R_{15}$ and $R_2'$ are as previously defined in claim 1.

11. A compound according to claim 1 represented by formula XII:

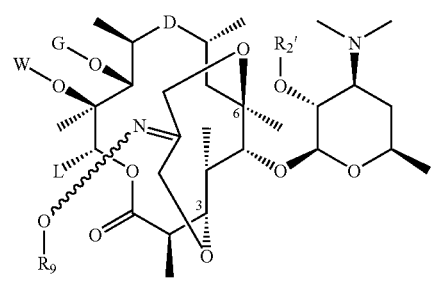

(XII)

where L, P, W, $R_9$ and $R_2'$ are as previously defined.

12. A compound according to claim 1 represented by formula XIII:

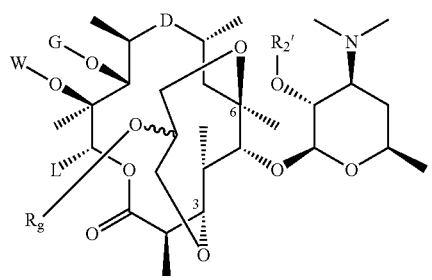

(XIII)

where D, L, P, W, $R_9$ and $R_2'$ are as previously defined.

13. A compound according to claim 1 selected from:

(a) Compound of formula III, wherein A=B=G=W=Y=Z=hydrogen, L is —CH$_2$CH$_3$, R$_2$'=Ac, X=

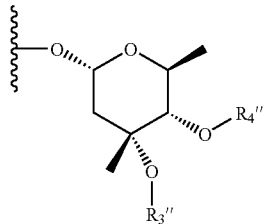

where R$_3$" is —CH$_3$ and R$_4$"=Ac;

(b) Compound of formula III, wherein A=B=G=W=Y=Z=R$_2$'=hydrogen, L is —CH$_2$CH$_3$, X=

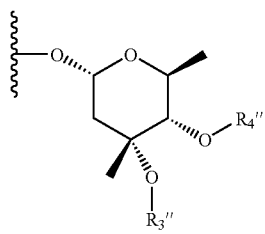

where R$_3$' is —CH$_3$ and R$_4$"=Ac;

(c) Compound of formula III, wherein A=B=G=W=Y=Z=R$_2$'=hydrogen, L is —CH$_2$CH$_3$, X=

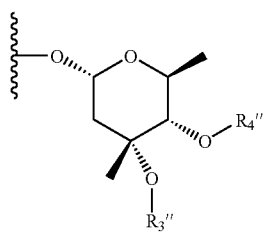

where R$_3$' is —CH$_3$ and R$_4$"=H;

(d) Compound of formula III, wherein A=B=G=W=X=Y=Z=R$_2$'=hydrogen, L is —CH$_2$CH$_3$;

(e) Compound of formula VIII, wherein R$_{14}$ and R$_{15}$ taken together with the carbon atom to which they are attached are CHCH=CH$_2$, G=W=Y=Z=hydrogen, L is —CH$_2$CH$_3$, $_{R2}$'=Ac, X=

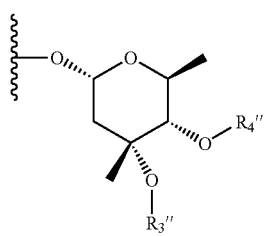

where R$_3$" is —CH$_3$ and R$_4$"=Ac;

(f) Compound of formula VIII, wherein R$_{14}$ and R$_{15}$ taken together with the carbon atom to which they are attached are CHCH=CH$_2$, G=W=Y=Z=R$_2$'=hydrogen, L is CH$_2$CH$_3$, X=

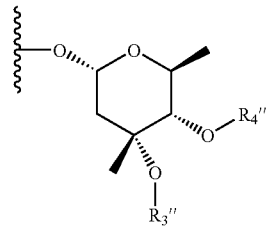

where R$_3$Δ is —CH$_3$ and R$_4$"=Ac;

(g) Compound of formula VIII, wherein R$_{14}$ and R$_{15}$ taken together with the carbon atom to which they are attached are CHCH=CH$_2$, R$_{15}$=G=W=Y=Z=R$_2$'=hydrogen, L is —CH$_2$CH$_3$, X=

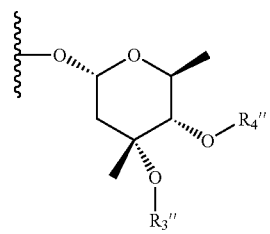

where R$_3$" is —CH$_3$ and R$_4$"=H;

(h) Compound of formula IX, wherein R$_{14}$ and R$_{15}$ taken together with the carbon atom to which they are attached are C=CH$_2$, G=W=Y=Z=hydrogen, L is —CH$_2$CH$_3$, R$_2$'=Ac, X=

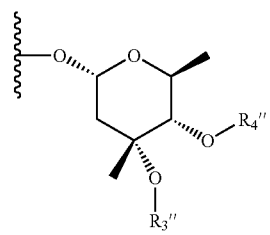

where R$_3$" is —CH$_3$ and R$_4$"=Ac;

(i) Compound of formula IX, wherein R$_{14}$ and R$_{15}$ taken together with the carbon atom to which they are aftached are C=CH$_2$, G=W=Y=Z=R$_2$'=hydrogen, L is —CH$_2$CH$_3$, X=

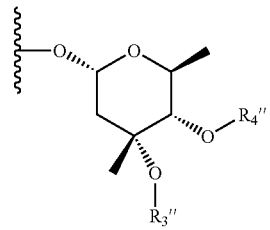

where R$_3$" is —CH$_3$ and R$_4$"=Ac;

(j) Compound of formula X, wherein $R_{14}$ and $R_{15}$ taken together with the carbon atom to which they are attached are C=$CH_2$, G=W=hydrogen, $R_2'$=Ac, L is —$CH_2CH_3$, D=—$NHCH_2$—;

(k) Compound of formula X, wherein $R_{14}$ and $R_{15}$ taken together with the carbon atom to which they are attached are C=$CH_2$, G=W=hydrogen, $R_2'$=Ac, L is —$CH_2CH_3$, D=—$N(CH_3)CH_2$—;

(l) Compound of formula X, wherein $R_{14}$ and $R_{15}$ taken together with the carbon atom to which they are attached are C=$CH_2$, G=W=$R_2'$=hydrogen, L is —$CH_2CH_3$, D=—$N(CH_3)CH_2$—;

(m) Compound of formula X, wherein $R_{14}$ and $R_{15}$ taken together with the carbon atom to which they are attached are C=CH-[5-(2-(2-pyridyl)thiophene)], G=W=$R_2'$=hydrogen, L is —$CH_2CH_3$, D=—$N(CH_3)CH_2$—;

(n) Compound of formula X, wherein $R_{14}$ and $R_{15}$ taken together with the carbon atom to which they are attached are C=O, G=W=$R_2'$=hydrogen, L is —$CH_2CH_3$, D=—$N(CH_3)CH_2$—;

(o) Compound of formula X, wherein $R_{14}$ and $R_{15}$ taken together with the carbon atom to which they are attached are C=N—O—$CH_2$—[5-(2-(1-pyrazolyl)pyridine)], G=W=$R_2'$=hydrogen, L is —$CH_2CH_3$, D=—$N(CH_3)CH_2$—;

(p) Compound of formula X, wherein $R_{14}$ and $R_{15}$ taken together with the carbon atom to which they are attached are CH—OH, G=W=$R_2'$=hydrogen, L is —$CH_2CH_3$, D=—$N(CH_3)CH_2$—;

(q) Compound of formula X, wherein $R_{14}$ and $R_{15}$ taken together with the carbon atom to which they are attached are CH—O—$CH_2$C≡CH G=W=$R_2'$=hydrogen, L is —$CH_2CH_3$, D=—$N(CH_3)CH_2$—;

(r) Compound of formula X, wherein $R_{14}$ and $R_{15}$ taken together with the carbon atom to which they are attached are CH—O—$CH_2$C≡C-[5-(2-(2-pyridyl)thiophene)], G=W=$R_2'$=hydrogen, L is —$CH_2CH_3$, D=—$N(CH_3)CH_2$—;

(s) Compound of formula X, wherein $R_{14}$ and $R_{15}$ taken together with the carbon atom to which they are attached are CH—O—$CH_2$CH=CH-[5-(2-(2-pyridyl)thiophene)], G=W=$R_2'$=hydrogen, L is —$CH_2CH_3$, D=—$N(CH_3)CH_2$—;

(t) Compound of formula XI, wherein $R_{14}$ and $R_{15}$ taken together with the carbon atom to which they are attached are C=$CH_2$, G=W=hydrogen, $R_2'$=Ac, L is —$CH_2CH_3$, P=$CH_2$;

(u) Compound of formula XI, wherein $R_{14}$ and $R_{15}$ taken together with the carbon atom to which they are attached are C=O, G=W=$R_2'$=hydrogen, L is —$CH_2CH_3$, P=$CH_2$.

(v) Compound of formula XI, wherein $R_{14}$ and $R_{15}$ taken together with the carbon atom to which they are attached are C=CH-[5-(2-(2-pyridyl)thiophene)], G=W=$R_2'$=hydrogen, L is —$CH_2CH_3$, P=$CH_2$;

(w) Compound of formula XI, wherein $R_{14}$ and $R_{15}$ taken together with the carbon atom to which they are attached are C=N—O—$CH_2$-[5-(2-(1-pyrazolyl)pyridine)], G=W=$R_2'$=hydrogen, L is —$CH_2CH_3$, P=$CH_2$;

(x) Compound of formula XI, wherein $R_{14}$ and $R_{15}$ taken together with the carbon atom to which they are attached are CH—O—$CH_2$CCH, G=W=$R_2'$=hydrogen, L is —$CH_2CH_3$, P=$CH_2$;

(y) Compound of formula XI, wherein $R_{14}$ and $R_{15}$ taken together with the carbon atom to which they are attached are CH—O—$CH_2$C≡C-[5-(2-(2-pyridyl)thiophene)], G=W=$R_2'$=hydrogen, L is —$CH_2CH_3$, P=$CH_2$;

(z) Compound of formula XI, wherein $R_{14}$ and $R_{15}$ taken together with the carbon atom to which they are attached are CH—O—$CH_2$CH=CH-[5-(2-(2-pyridyl)thiophene)], G=W=$R_2'$=hydrogen, L is —$CH_2CH_3$, P=$CH_2$;

(aa) Compound of formula X, wherein $R_{14}$ and $R_{15}$ taken together with the carbon atom to which they are attached are CH—O—$CH_2$CH=CH-(3-quinoline), G=W=$R_2'$=hydrogen, L is —$CH_2CH_3$, D=—$N(CH_3)CH_2$—;

(bb) Compound of formula XI, wherein $R_{14}$ and $R_{15}$ taken together with the carbon atom to which they are attached are CH—OH, W=$R_2'$=hydrogen, L is —$CH_2CH_3$, P=$CH_2$C(=$CH_2$)$CH_2$;

(cc) Compound of formula XI, wherein $R_{14}$ and $R_{15}$ taken together with the carbon atom to which they are attached are CH—OH, W=$R_2'$=hydrogen, L is —$CH_2CH_3$, P=CH(CH=$CH_2$)$CH_2$.

14. A method for treating a bacterial infection in a subject in need of such treatment, comprising administering to said subject a therapeutically effective amount of a compound according to claim 1.

15. A pharmaceutical composition comprising a therapeutically effective amount of a compound of claim 1 or a pharmaceutically acceptable salt, ester or prodrug thereof, in combination with a pharmaceutically acceptable carrier.

16. A method for controlling a bacterial infection in a subject, comprising administering to said subject a therapeutically effective amount of a pharmaceutical composition according to claim 15.

17. The method according to claim 14 wherein the infection is a protozoa infection or bacterial infection and disorders related to such infections.

18. The method according to claim 17 wherein the infection or disorder is selected from the group consisting of pneumonia, otitis media, sinusitus, bronchitis, tonsillitis, and mastoiditis related to infection by *Streptococcus pneumoniae, Haemophilus influenzae, Moraxella catarrhalis, Staphylococcus aureus,* or *Peptostreptococcus* spp. *Pseudomonas* spp.; pharynigitis, rheumatic fever, and glomerulonephritis related to infection by *Streptococcus pyogenes*, Groups C and G *streptococci, Clostridium diptheriae,* or *Actinobacillus haemolyticum*; respiratory tract infections related to infection by *Mycoplasma pneumoniae, Legionella pneumophila, Streptococcus pneumoniae, Haemophilus influenzae,* or *Chlamydia pneumoniae*; uncomplicated skin and soft tissue infections, abscesses and osteomyelitis, and puerperal fever related to infection by *Staphylococcus aureus,* coagulase-positive *staphylococci* (i.e., *S. epidermidis, S. helolyticus,* etc.), *S. pyogenes, S. agalactiae,* Streptococcal groups C-F (minute-colony *streptococci*), *viridans streptococci, Corynebacterium* spp., *Clostridium* spp., or *Bartonella henselae*; uncomplicated acute urinary tract infections related to infection by *S. saprophyticus* or *Enterococcus* spp.; *urethritis* and *cervicitis;* and sexually transmitted diseases related to infection by *Chalmydia trachomatis, Haemophilus ducreyi, Treponema pallidum, Ureaplasma urealyticum,* or *Nesseria gonorrheae;* toxin diseases related to infection by *S. aureus,* or Groups A, S. and C *streptococci;* ulcers related to infection by Helicobacter pylori; systemic febrile syndromes related to infection by *Borrelia recurrentis;* Lyme disease related to infection by *Borrelia burgdorferi*, conjunctivitis, keratitis, and dacrocystitis related to infection by *C. trachomatis, N. gonnorrhoeae, S. aureus, S. pneumoniae, S. pyrogenes, H. influenzae,* or *Listeria* spp.; disseminated *Mycobacterium avium* complexx (MAX) disease related to infection by *Mycobacterium avium,* or *Mycobacterium intracellulare;* gastroenteritis related to infection by *Campylobacter jejuni;* intestinal protozoa related to infection by *Cryptosporidium* spp. odontogenic infection related to infection by *viridans streptococci;* persistent cough related to infection by *Bordetella pertussis;* gas gangrene related to infection by *Clostridium perfringens* or *Bacteroides* spp.; Skin infection by *S. aureus,* Propionibacterium acne; atherosclerosis related to infection by *Helicobacter pylori* and *Chlamydia pneumoniae.*

19. A process for producing compounds of the following formulae according to claim 1:

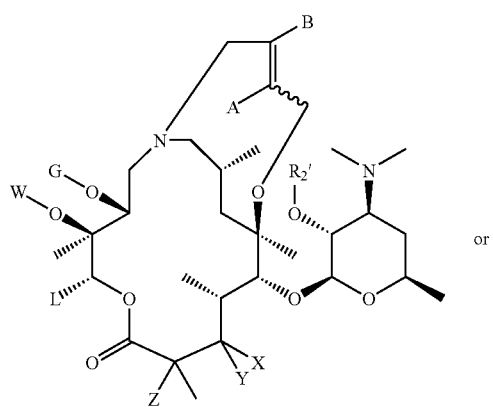

wherein A, B, G, L, W, X, Y, Z and $R_2'$ are as defined in claim 1, comprising the steps of:

(1) reacting compounds of the formula Ia:

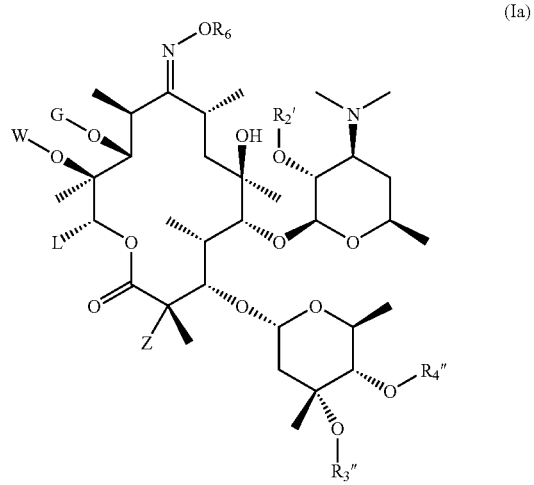

wherein:
(1) $R_3''$ and $R_4''$ are as defined in claim 1; and
(2) G, L, W, Z, $R_6$ and $R_2'$ are as defined in claim 1, with,

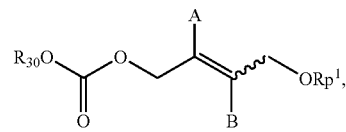

wherein A, B, and $R_p^1$ are as defined in claim 1, and $R_{30}$ is $C_1$-$C_{12}$-alkyl, in the presence of a phosphine ligand and Pd(0) catalyst in an aprotic solvent at room to reflux temperature to prepare compounds of the formula:

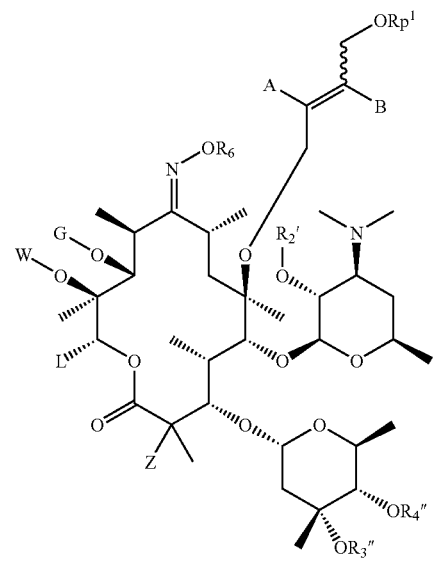

where A, B, G, L, W, Z, $R_6$, $R_p^1$, $R_2'$, $R_3''$ and $R_4''$ are as defined in claim 1, (2) reacting the compounds prepared in step (1) with an oxime activating agent, followed by reduction with a hydride reducing reagent to prepare compounds of the formula:

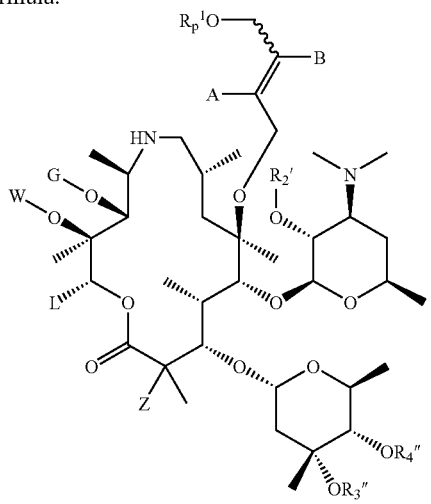

where A, B, G, L, W, Z, $R_p^1$, $R_2'$, $R_3''$ and $R_4''$ are as defined in claim 1, (3) reacting the compounds prepared in step (2) in the presence of a phosphine ligand and Pd(0) catalyst under reflux conditions to yield compounds of the following formulae:

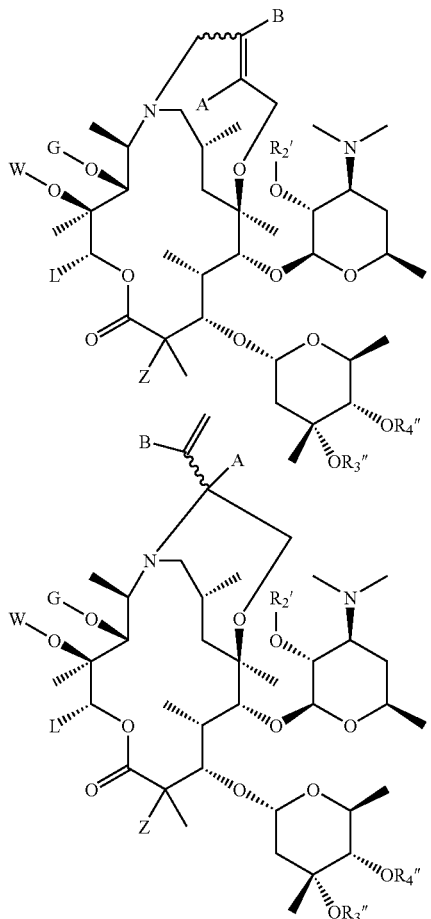

where A, B, G, L, W, Z, $R_2'$, $R_3''$ and $R_4''$ are as defined in claim 1, (4) reacting the compounds prepared in step (3) with a mild acid, followed by oxidizing the hydroxyl in the C3 position with an oxidant such as Dess-Martin periodinane, Corey-Kim oxidation, or a Moffat type oxidation, chromium or manganese reagents to produce compounds of the following formulae:

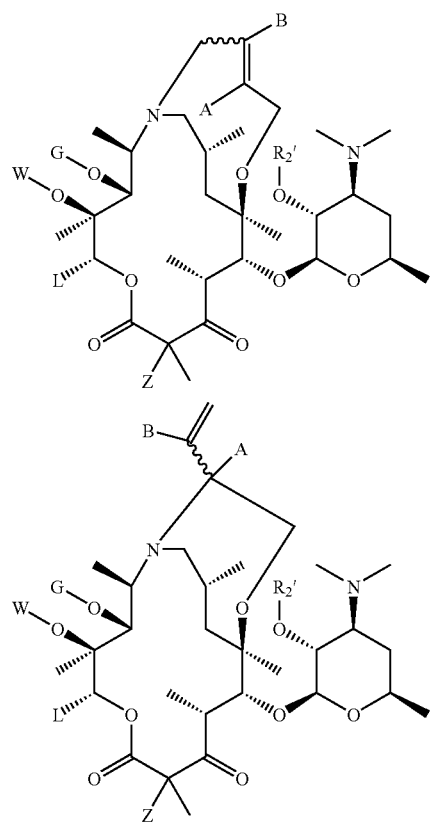

where A, B, G, L, W, Z, and $R_2'$ are as defined in claim 1.

20. A process for producing compounds of the following formula according to claim 1:

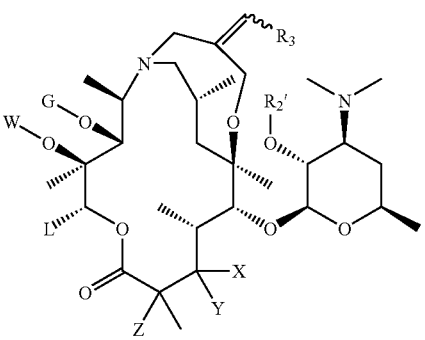

wherein G, L, W, X, Y, Z, $R_3$ and $R_2'$ are as defined in claim 1, comprising the steps of:

(1) reacting compounds of the formula Ia:

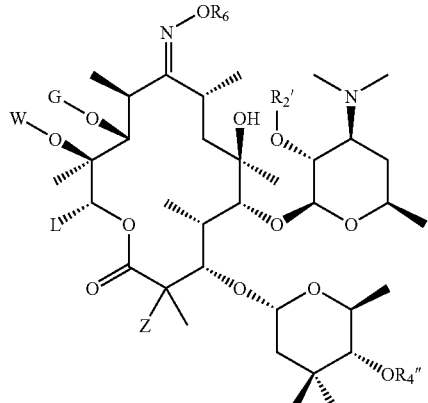

wherein:
 (1) $R_3''$ and $R_4''$ are as defined in claim 1; and
 (2) G, L, W, Z, $R_6$ and $R_2'$ are as defined in claim 1, with,

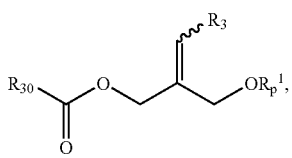

wherein $R_3$ and $R_p^1$ are as defined in claim 1, $R_{30}$ is $C_1$-$C_{12}$-alkyl, in the presence of a phosphine ligand and Pd(0) catalyst in an aprotic solvent at room to reflux temperature to prepare compounds of the formula:

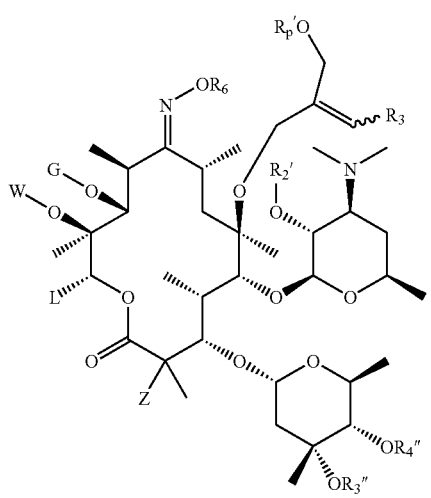

wherein G, L, W, Z, $R_6$, $R_p^1$, $R_3$, $R_3''$, $R_2''$ and $R_2'$ are as defined in claim 1

(2) reacting the compounds prepared in step (1) with an oxime activating agent to prepare compounds of the formula:

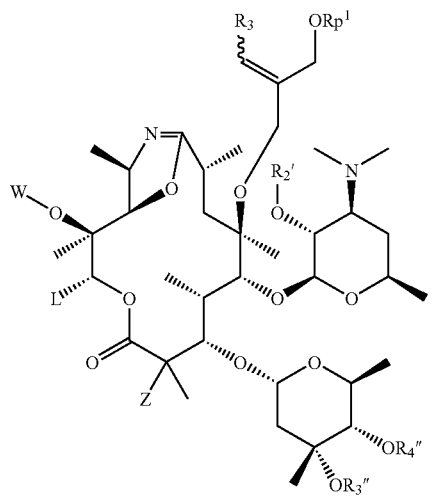

wherein L, W, Z, $R_p^1$, $R_3$, $R_3''$, $R_4''$ and $R_2'$ are as defined in claim 1

(3) reacting the compounds prepared in step (2) with a hydride reducing reagent, subsequently in the presence of a phosphine ligand and Pd(0) catalyst under reflux conditions to yield compounds of the following formula:

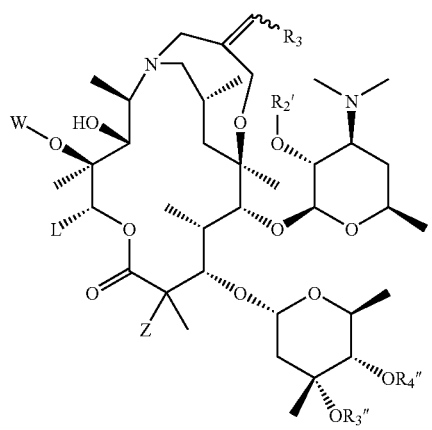

wherein L, W, Z, $R_3$, $R_3''$, $R_4''$ and $R_2'$ are as defined in claim 1

(4) reacting the compounds prepared in step (3) with a mild acid, followed by oxidizing the hydroxyl in the C3-position with an oxidant such as Dess-Martin periodinane, Corey-Kim oxidation, or a Moffat type oxidation, chromium or manganese reagents to produce compounds of the following formula:

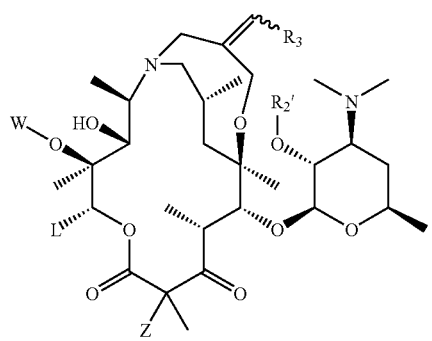

wherein L, W, Z, $R_3$ and $R_2'$ are as defined in claim 1.

21. A process for producing compounds of the formula according to claim 1:

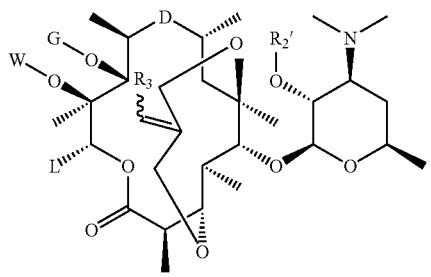

wherein D, G, L, W, $R_3$ and $R_2'$ are as defined in claim 1, comprising the steps of:

(1) reacting compounds of the following formula:

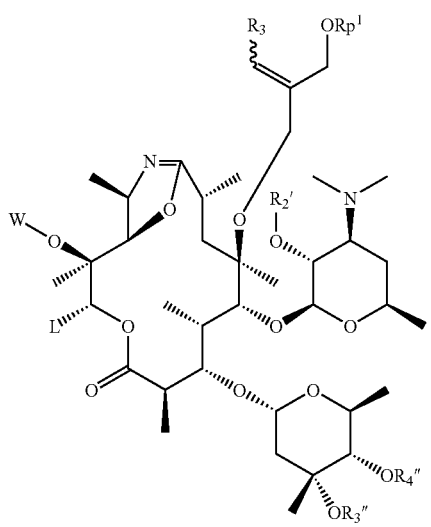

wherein L, W, $R_p^1$, $R_3$, $R_3''$, $R_4''$ and $R_2'$ are as defined in claim 1 with a mild acid to give compounds of the formula:

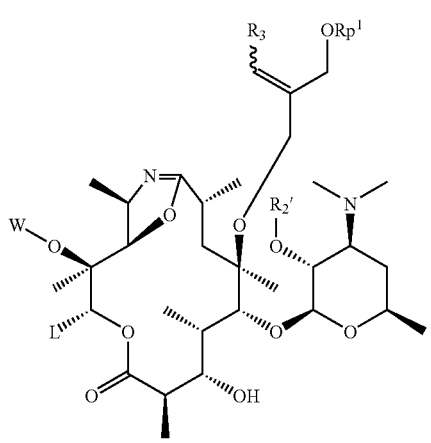

wherein L, W, $R_p^1$, $R_3$ and $R_2'$ are as defined in claim 1

(2) reacting the compounds prepared in step (1) with a hydride reducing reagent such as but not limited to sodium cyanoborohydride, followed by reductive amination with aldehyde to yield compounds of the following formula:

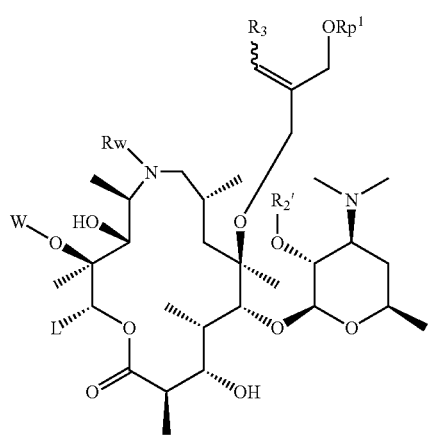

wherein L, W, $R_3$ and $R_2'$ are as defined in claim 1 and Rw is $C_1$-$C_6$ alkyl, optionally substituted with one or more substituents selected from the group consisting of: halogen, aryl, substituted aryl, heteroaryl, and substituted heteroaryl, (3) reacting the compounds prepared in step (2) in the presence of a phosphine ligand and Pd(0) catalyst under reflux conditions to yield compounds of the following formula:

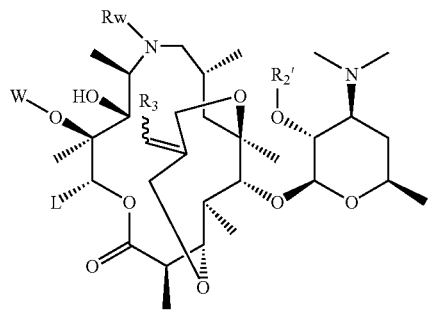

wherein L, W, Rw, $R_3$ and $R_2'$ are as previously defined.

22. A process for producing compounds of the following formula according to claim 1:

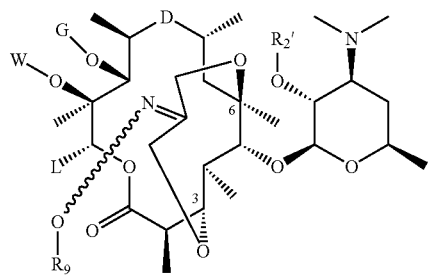

wherein D, G, L, W, $R_9$ and $R_2'$ are as defined in claim 1, comprising the steps of:

(1) oxidative cleavage of the compounds with the following formula:

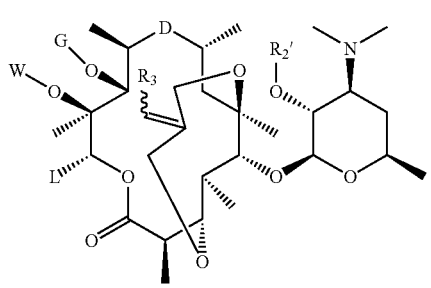

wherein D, G, L, W, $R_3$ and $R_2'$ are as defined in claim 1, with oxidizing reagents such as, but not limited to, Jones, osmium tetroxide, or Lemieux-von Rudloff reagents or via ozonolysis to give compounds of the following formula:

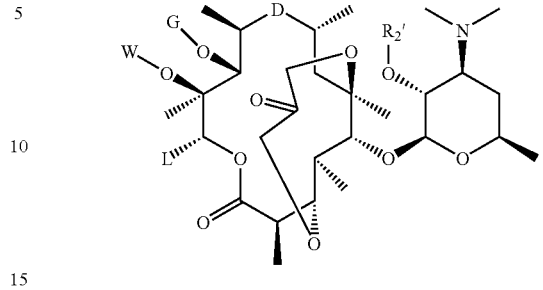

(2) reacting the compounds prepared in step (1) with $R_9ONH_2$ in a presence of a mild acid.

* * * * *

UNITED STATES PATENT AND TRADEMARK OFFICE
CERTIFICATE OF CORRECTION

PATENT NO. : 7,402,568 B2  Page 1 of 1
APPLICATION NO. : 11/236043
DATED : July 22, 2008
INVENTOR(S) : Yat Sun Or et al.

It is certified that error appears in the above-identified patent and that said Letters Patent is hereby corrected as shown below:

Column 103 Claim 4, Delete Formula (V) and replace with Formula (V) shown below.

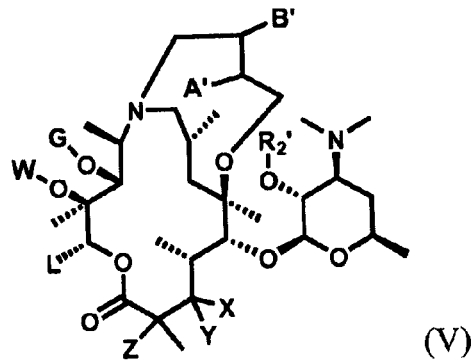

(V)

Column 106 Claim 12, Delete Formula (XII) and replace with Formula (XII) shown below.

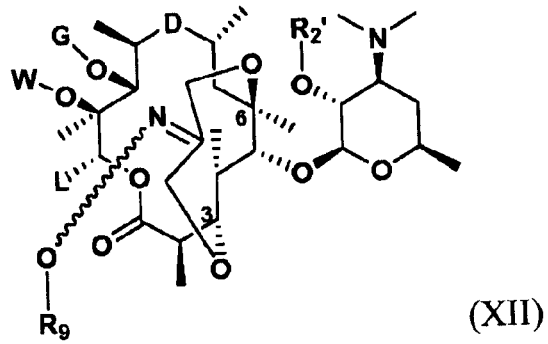

(XII)

Signed and Sealed this

Seventeenth Day of March, 2009

JOHN DOLL
*Acting Director of the United States Patent and Trademark Office*